US012790341B2

(12) United States Patent
Jia et al.

(10) Patent No.: US 12,790,341 B2
(45) Date of Patent: Nov. 10, 2026

(54) sGC STIMULATORS

(71) Applicant: Tisento Therapeutics Inc., Cambridge, MA (US)

(72) Inventors: Lei Jia, San Diego, CA (US); Ara Mermerian, Waltham, MA (US); Timothy Claude Barden, Gibsonia, PA (US); Thomas Wai-Ho Lee, Lexington, MA (US); Karthik Iyer, Cambridge, MA (US); Glen Robert Rennie, Somerville, MA (US); Rajesh R. Iyengar, West Newton, MA (US); Joon Jung, Newton, MA (US); Paul Allan Renhowe, Sudbury, MA (US)

(73) Assignee: Tisento Therapeutics Inc., Cambridge, MA (US)

( * ) Notice: Subject to any disclaimer, the term of this patent is extended or adjusted under 35 U.S.C. 154(b) by 375 days.

(21) Appl. No.: 18/287,612

(22) PCT Filed: Apr. 19, 2022

(86) PCT No.: PCT/US2022/025310

§ 371 (c)(1),
(2) Date: Oct. 19, 2023

(87) PCT Pub. No.: WO2022/225903

PCT Pub. Date: Oct. 27, 2022

(65) Prior Publication Data

US 2024/0208979 A1 Jun. 27, 2024

Related U.S. Application Data

(60) Provisional application No. 63/229,248, filed on Aug. 4, 2021, provisional application No. 63/177,020, filed on Apr. 20, 2021.

(51) Int. Cl.
*C07D 487/04* (2006.01)
*A61K 31/506* (2006.01)

(52) U.S. Cl.
CPC .......... *C07D 487/04* (2013.01); *A61K 31/506* (2013.01)

(58) Field of Classification Search
CPC ............................ C07D 487/04; A61K 31/506
USPC .......................................................... 514/249
See application file for complete search history.

(56) References Cited

U.S. PATENT DOCUMENTS

| | | | |
|---|---|---|---|
| 2019/0282579 | A1 | 9/2019 | Berger et al. |
| 2024/0207265 | A1 | 6/2024 | Jia et al. |

FOREIGN PATENT DOCUMENTS

| | | | |
|---|---|---|---|
| CN | 117915917 | A | 4/2024 |
| CN | 120112293 | A | 6/2025 |
| CN | 120225524 | A | 6/2025 |
| WO | 2014/013338 | A2 | 1/2014 |
| WO | 2015/106268 | A1 | 7/2015 |
| WO | 2016/081668 | A1 | 5/2016 |
| WO | 2016/191335 | A1 | 12/2016 |
| WO | 2017/197555 | A1 | 11/2017 |
| WO | 2018/045276 | A1 | 3/2018 |
| WO | 2018/089328 | A1 | 5/2018 |
| WO | 2019/126354 | A1 | 6/2019 |
| WO | 2019/173551 | A1 | 9/2019 |
| WO | 2019/211081 | A1 | 11/2019 |

OTHER PUBLICATIONS

Sandner et al., Soluble guanylate cyclase stimulators and their potential use: a patent review. Expert Opin Ther Pat. Mar. 2021;31(3):203-222.
International Search Report and Written Opinion for Application No. PCT/US2022/025310, dated Jul. 4, 2022, 9 pages.
International Preliminary Report on Patentability for Application No. PCT/US2022/025310, dated Nov. 2, 2023, 8 pages.
International Search Report and Written Opinion for Application No. PCT/US2022/025308, dated Jul. 21, 2022, 10 pages.
International Preliminary Report on Patentability for Application No. PCT/US2022/025308, dated Nov. 2, 2023, 9 pages.
U.S. Appl. No. 18/287,616, filed Oct. 19, 2023, Pending.

*Primary Examiner* — Kristin A Vajda
(74) *Attorney, Agent, or Firm* — McCarter & English, LLP; Xin Zhang; James M. Alburger

(57) ABSTRACT

The present disclosure relates to stimulators of soluble guanylate cyclase (sGC), pharmaceutically acceptable salts thereof and pharmaceutical formulations comprising them and their uses thereof, alone or in combination with one or more additional agents, for treating various diseases, wherein an increase in the concentration of nitric oxide (NO) and/or an increase in the concentration of cyclic Guanosine Monophosphate (cGMP), or both, or an upregulation of the NO pathway is desirable. In some embodiments, the compounds are those of Table I or a pharmaceutically acceptable salt thereof.

17 Claims, 2 Drawing Sheets sGC STIMULATORS

RELATED APPLICATIONS

This application is a 35 U.S.C. § 371 national stage filing of International Application No. PCT/US2022/025310, filed on Apr. 19, 2022, which in turn claims the benefit of priority to U.S. Provisional Application No. 63/177,020, filed on Apr. 20, 2021, and U.S. Provisional Application No. 63/229,248, filed on Aug. 4, 2021. The entire contents of each of the above-referenced applications are incorporated herein by reference.

FIELD OF THE INVENTION

The present disclosure relates to compounds that are stimulators of soluble guanylate cyclase (sGC) and pharmaceutically acceptable salts thereof. It also relates to pharmaceutical formulations and dosage forms comprising them and their uses thereof, alone or in combination with one or more additional agents, for treating various diseases. These are diseases that would benefit from sGC stimulation or from an increase in the concentration of nitric oxide (NO) and/or cyclic guanosine monophosphate (cGMP).

BACKGROUND OF THE INVENTION sGC is the primary receptor for NO in vivo. Upon binding to sGC, NO activates its catalytic domain and results in the conversion of guanosine-5'-triphosphate (GTP) into the secondary messenger cGMP. The increased level of cGMP, in turn, modulates the activity of downstream effectors including protein kinases, phosphodiesterases (PDEs) and ion channels. In the body, NO is synthesized from arginine and oxygen by various nitric oxide synthase (NOS) enzymes and by sequential reduction of inorganic nitrate. Experimental and clinical evidence indicates that reduced NO concentrations, reduced NO bioavailability and/or reduced responsiveness to endogenously produced NO contributes to the development of numerous diseases. sGC stimulators are heme-dependent agonists of the sGC enzyme that work synergistically with varying amounts of NO to increase its enzymatic conversion of GTP to cGMP. sGC stimulators are clearly differentiated from and structurally unrelated to another class of NO-independent, heme-independent agonists of sGC known as sGC activators.

Therapies that improve or restore the function of sGC offer considerable advantages over current alternative therapies that either target the pathway or otherwise benefit from the upregulation of the NO-sGC-cGMP pathway. There is an urgent need to develop new and safe therapies for patients with dysfunctional NO-sGC-cGMP pathway.

SUMMARY OF THE INVENTION

The present invention is based on the discovery that the compounds disclosed herein are sGC stimulators. Compounds with related structural features, particularly, with a 4-OH substituent on the pyrimidine ring, were previously known only as synthetic intermediates that could be used for the preparation for sGC stimulators having 4-amino substituents on the pyrimidine ring. It was unexpectedly found that the compounds of the present disclosure have potent sGC stimulatory activities. In a first aspect, the present invention is directed to sGC stimulator compounds of Table I or of Formula I and their pharmaceutically acceptable salts thereof.

TABLE I

| Exemplary sGC stimulators the invention. |
|---|
| 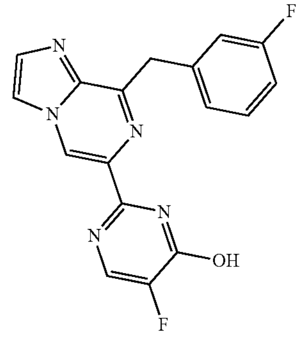 [SMILES: Oc1nc(-c2cn3ccnc3c(Cc3cccc(F)c3)n2)ncc1F] |
| I-1 |
| 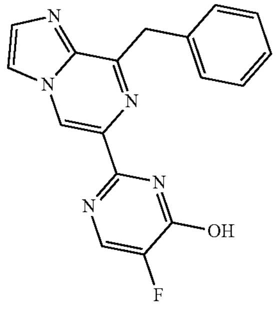 [SMILES: Oc1nc(-c2cn3ccnc3c(Cc3ccccc3)n2)ncc1F] |
| I-2 |
| 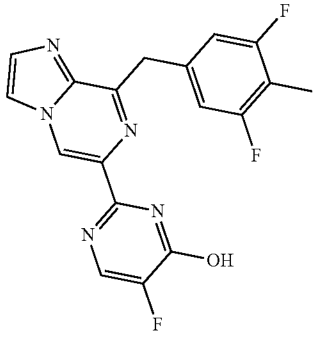 [SMILES: Cc1c(F)cc(Cc2nc(-c3ncc(F)c(O)n3)cn3ccnc23)cc1F] |
| I-3 |
| 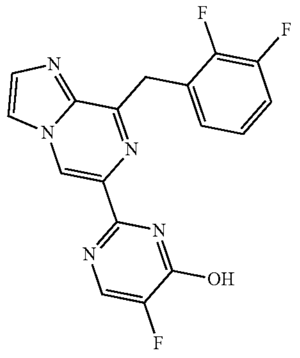 [SMILES: Oc1nc(-c2cn3ccnc3c(Cc3cccc(F)c3F)n2)ncc1F] |
| I-4 |

TABLE I-continued
Exemplary sGC stimulators the invention.
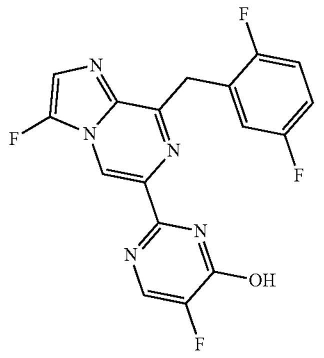 [SMILES: Oc1nc(-c2cn3c(F)cnc3c(Cc3cc(F)ccc3F)n2)ncc1F]
I-5
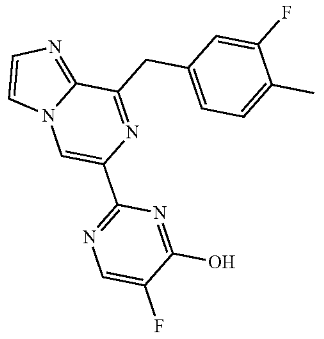 [SMILES: Cc1ccc(Cc2nc(-c3ncc(F)c(O)n3)cn3ccnc23)cc1F]
I-6
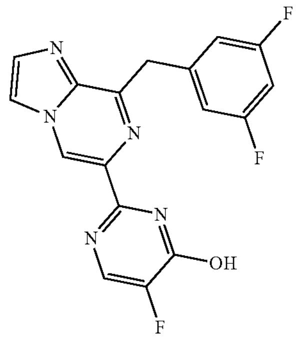 [SMILES: Oc1nc(-c2cn3ccnc3c(Cc3cc(F)cc(F)c3)n2)ncc1F]
I-7
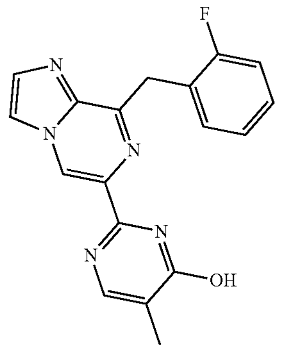 [SMILES: Cc1cnc(-c2cn3ccnc3c(Cc3ccccc3F)n2)nc1O]
I-8
TABLE I-continued
Exemplary sGC stimulators the invention.
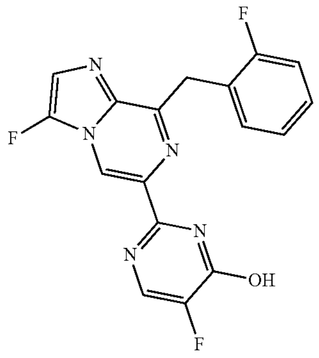 [SMILES: Oc1nc(-c2cn3c(F)cnc3c(Cc3ccccc3F)n2)ncc1F]
I-9
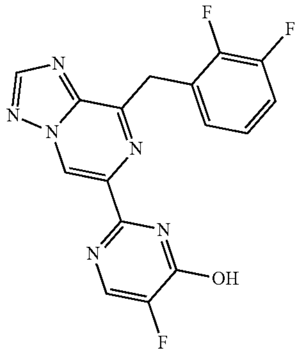 [SMILES: Oc1nc(-c2cn3ncnc3c(Cc3cccc(F)c3F)n2)ncc1F]
I-10
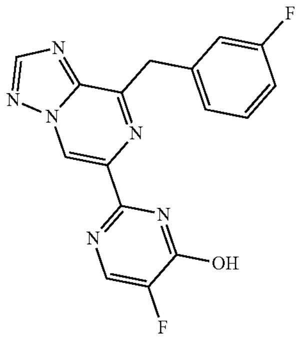 [SMILES: Oc1nc(-c2cn3ncnc3c(Cc3cccc(F)c3)n2)ncc1F]
I-11
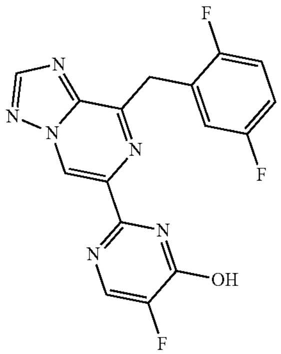 [SMILES: Oc1nc(-c2cn3ncnc3c(Cc3cc(F)ccc3F)n2)ncc1F]
I-12

TABLE I-continued
Exemplary sGC stimulators the invention.
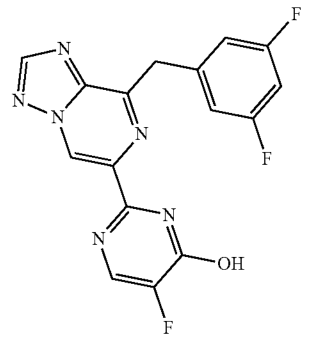 [SMILES: Oc1nc(-c2cn3ncnc3c(Cc3cc(F)cc(F)c3)n2)ncc1F]
I-13
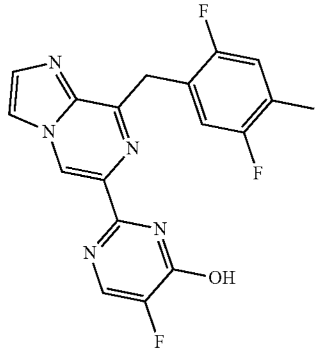 [SMILES: Cc1cc(F)c(Cc2nc(-c3ncc(F)c(O)n3)cn3ccnc23)cc1F]
I-14
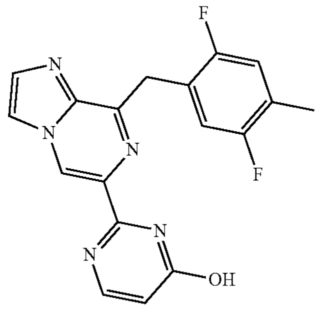 [SMILES: Cc1cc(F)c(Cc2nc(-c3nccc(O)n3)cn3ccnc23)cc1F]
I-15
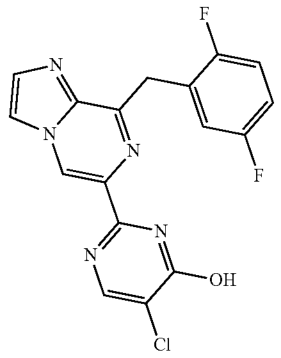 [SMILES: Oc1nc(-c2cn3ccnc3c(Cc3cc(F)ccc3F)n2)ncc1Cl]
I-16
TABLE I-continued
Exemplary sGC stimulators the invention.
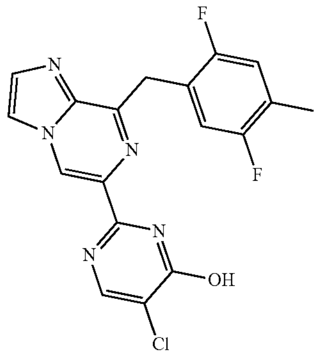 [SMILES: Cc1cc(F)c(Cc2nc(-c3ncc(Cl)c(O)n3)cn3ccnc23)cc1F]
I-17
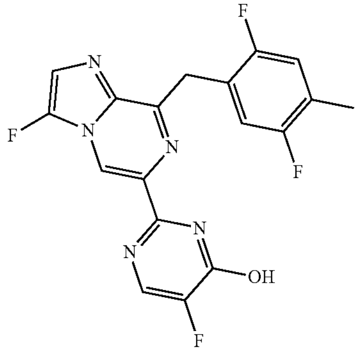 [SMILES: Cc1cc(F)c(Cc2nc(-c3ncc(F)c(O)n3)cn3c(F)cnc23)cc1F]
I-18
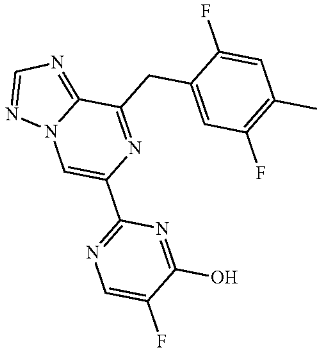 [SMILES: Cc1cc(F)c(Cc2nc(-c3ncc(F)c(O)n3)cn3ncnc23)cc1F]
I-19
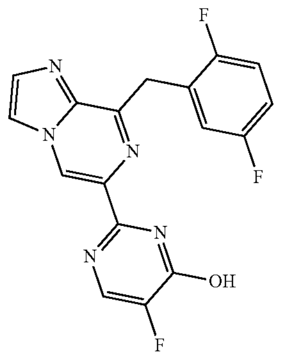 [SMILES: Oc1nc(-c2cn3ccnc3c(Cc3cc(F)ccc3F)n2)ncc1F]
I-20

In a second aspect, the invention relates to pharmaceutical compositions comprising a compound of Table I, Formula I, or a pharmaceutically acceptable salt thereof and at least one pharmaceutically acceptable excipient or carrier.

In a third aspect, the invention relates to a method of treating a disease in a subject in need thereof, comprising administering, alone or in combination therapy, a therapeutically effective amount of a compound of Table I, Formula I, or a pharmaceutically acceptable salt thereof, or a pharmaceutical composition thereof, to the subject; wherein the disease is one that would benefit from sGC stimulation or from an increase in the concentration of NO and/or cGMP. Also provided is the use of a compound of Table I, Formula I, or a pharmaceutically acceptable salt thereof, or a pharmaceutical composition thereof, for the manufacture of a medicament for treating a disease in a subject in need thereof, wherein the disease is one that would benefit from sGC stimulation or from an increase in the concentration of NO and/or cGMP. In certain embodiments, the invention relates to a compound of Table I, or a pharmaceutically acceptable salt thereof, or a pharmaceutical composition thereof, for use in treating a disease in a subject in need thereof, wherein the disease is one that would benefit from sGC stimulation or from an increase in the concentration of NO and/or cGMP.

DETAILED DESCRIPTION OF THE INVENTION

Figure 1:
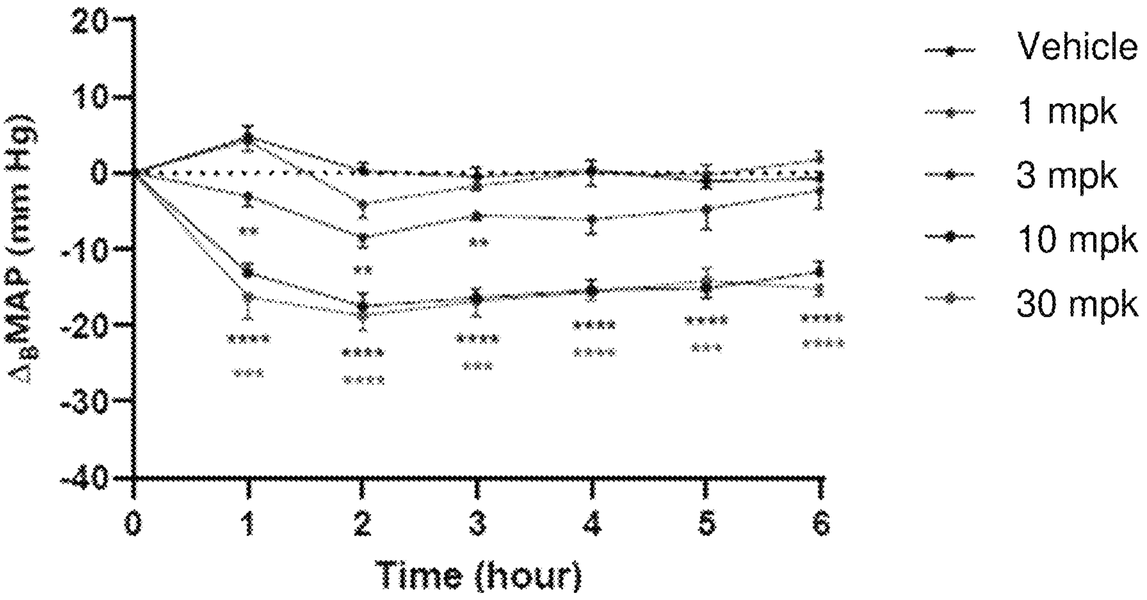
FIG. 1 shows the effect of compound I-14 on change from baseline in MAP ($\Delta_B$MAP) in male, normotensive rats.

Reference will now be made in detail to certain embodiments of the invention, examples of which are illustrated in the accompanying structures and formulae. While the invention will be described in conjunction with the enumerated embodiments, it will be understood that they are not intended to limit the invention to those embodiments. Rather, the invention is intended to cover all alternatives, modifications and equivalents that may be included within the scope of the present invention as defined by the claims. The present invention is not limited to the methods and materials described herein but include any methods and materials similar or equivalent to those described herein that could be used in the practice of the present invention. In the event that one or more of the incorporated literature references, patents or similar materials differ from or contradict this application, including but not limited to defined terms, term usage, described techniques or the like, this application controls.

Definitions and General Terminology

For purposes of this disclosure, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry", Thomas Sorrell, University Science Books, Sausalito: 1999, and "March's Advanced Organic Chemistry", 5$^{th}$ Ed., Smith, M. B. and March, J., eds. John Wiley & Sons, New York: 2001, which are herein incorporated by reference in their entirety.

Unless otherwise stated, all tautomeric forms of the compounds of the present disclosure are also within the scope of the invention.

In one embodiment, the present disclosure may include replacement of hydrogen with deuterium (i.e., $^2$H), which may afford certain therapeutic advantages resulting from greater metabolic stability (e.g., increased in vivo half-life or reduced dosage requirements) and hence may be preferred in some circumstances. Deuterium labeled compounds of the present invention can generally be prepared by following procedures analogous to those disclosed in the Schemes and/or in the Examples herein below, by substituting a deuterated reagent for a non-deuterated reagent.

As used herein, the terms "halogen" or "halo" mean any of F (Fluoro), Cl (Chloro), Br (Bromo), or I (Iodo).

The term "hydroxyl" or "hydroxy" refers to —OH.

The term "alkyl", as used herein, refers to a saturated unbranched (e.g., linear) or branched monovalent hydrocarbon radical. A $C_x$ alkyl is an alkyl chain containing x carbon atoms, wherein x is an integer different from 0. A "$C_{x-y}$ alkyl", wherein x and y are two different integers, both different from 0, is an alkyl chain containing between x and y number of carbon atoms, inclusive. For example, a $C_{1-6}$ alkyl is an alkyl as defined above containing any number between 1 and 6 carbon atoms. Examples of alkyl groups include, but are not limited to, methyl (i.e., $C_1$ alkyl), ethyl (i.e., $C_2$ alkyl), n-propyl (a $C_3$ alkyl), isopropyl (a different $C_3$ alkyl), n-butyl, isobutyl, s-butyl, t-butyl, pentyl, hexyl, heptyl, octyl and the like.

The term "fluoroalkyl", as used herein, refers to an alkyl group as defined above in which one or more of the hydrogen atoms attached to the chain carbon atoms has been replaced by fluoro at any one or more carbon atoms of the alkyl group. For example, a fluoroalkyl substituted with 1 to 3 fluoro atoms is an alkyl group in which 1 to 3 hydrogen atoms have been replaced with fluoro atoms at any position, either on the same carbon atom or different carbon atoms of the alkyl chain.

The compounds of the invention are defined herein by their chemical structures and/or chemical names. Where a compound is referred to by both a chemical structure and a chemical name, and the chemical structure and chemical name conflict, the chemical structure is determinative of the compound's identity.

Compound/Composition Embodiments

A first embodiment of the invention is a compound of Table I or a pharmaceutically acceptable salt thereof.

A second embodiment of the invention is a compound of Table II or a pharmaceutically acceptable salt thereof.

TABLE II

| Exemplary sGC stimulators of the invention. |
| --- |
| 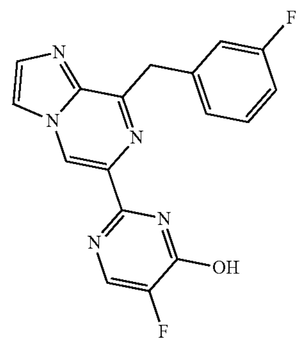 [SMILES: Oc1nc(-c2cn3ccnc3c(Cc3cccc(F)c3)n2)ncc1F] |

TABLE II-continued
| Exemplary sGC stimulators of the invention. |
| --- |
I-1
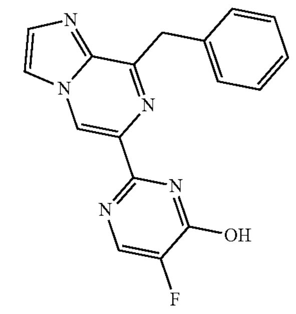 [SMILES: Oc1nc(-c2cn3ccnc3c(Cc3ccccc3)n2)ncc1F]
I-2
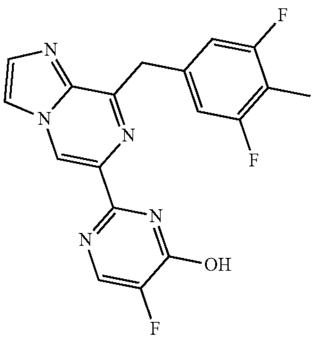 [SMILES: Cc1c(F)cc(Cc2nc(-c3ncc(F)c(O)n3)cn3ccnc23)cc1F]
I-3
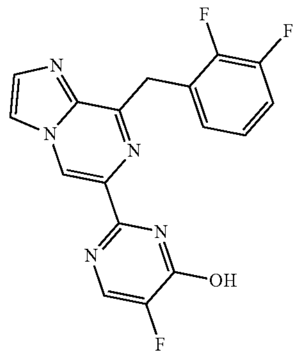 [SMILES: Oc1nc(-c2cn3ccnc3c(Cc3cccc(F)c3F)n2)ncc1F]
I-4
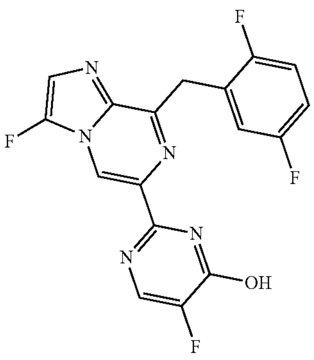 [SMILES: Oc1nc(-c2cn3c(F)cnc3c(Cc3cc(F)ccc3F)n2)ncc1F]
I-5
TABLE II-continued
| Exemplary sGC stimulators of the invention. |
| --- |
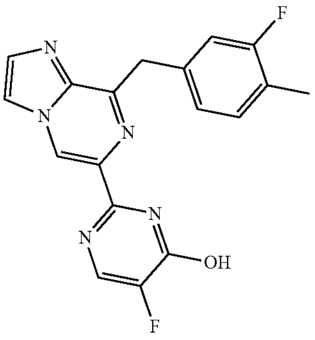 [SMILES: Cc1ccc(Cc2nc(-c3ncc(F)c(O)n3)cn3ccnc23)cc1F]
I-6
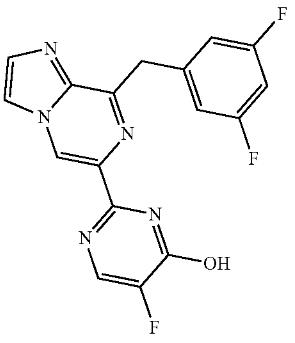 [SMILES: Oc1nc(-c2cn3ccnc3c(Cc3cc(F)cc(F)c3)n2)ncc1F]
I-7
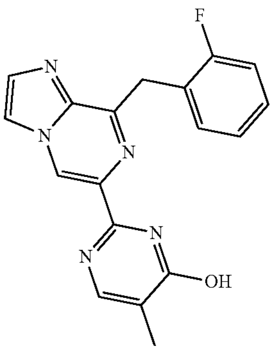 [SMILES: Cc1cnc(-c2cn3ccnc3c(Cc3ccccc3F)n2)nc1O]
I-8
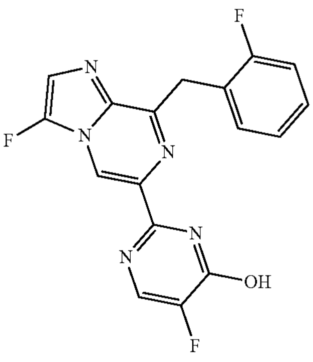 [SMILES: Oc1nc(-c2cn3c(F)cnc3c(Cc3ccccc3F)n2)ncc1F]
I-9

TABLE II-continued
| Exemplary sGC stimulators of the invention. |
|---|
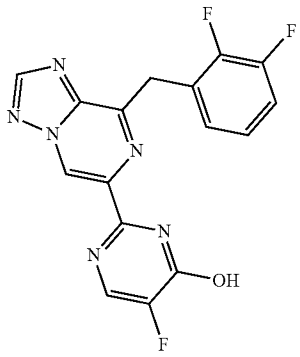 [SMILES: Oc1nc(-c2cn3ncnc3c(Cc3cccc(F)c3F)n2)ncc1F]
I-10
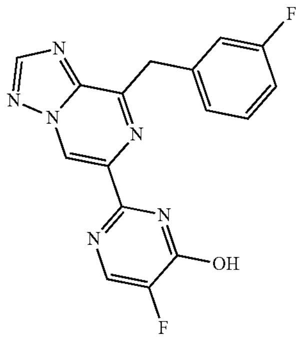 [SMILES: Oc1nc(-c2cn3ncnc3c(Cc3cccc(F)c3)n2)ncc1F]
I-11
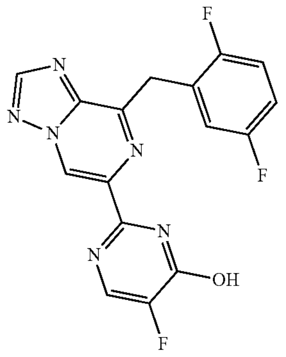 [SMILES: Oc1nc(-c2cn3ncnc3c(Cc3cc(F)ccc3F)n2)ncc1F]
I-12
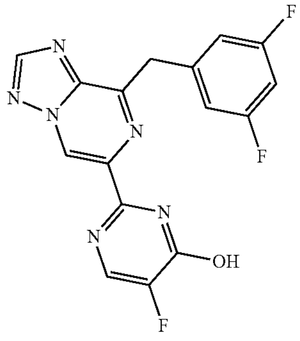 [SMILES: Oc1nc(-c2cn3ncnc3c(Cc3cc(F)cc(F)c3)n2)ncc1F]
I-13
TABLE II-continued
| Exemplary sGC stimulators of the invention. |
|---|
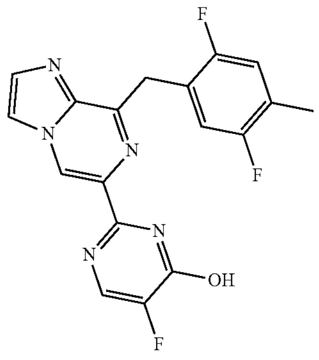 [SMILES: Cc1cc(F)c(Cc2nc(-c3ncc(F)c(O)n3)cn3ccnc23)cc1F]
I-14
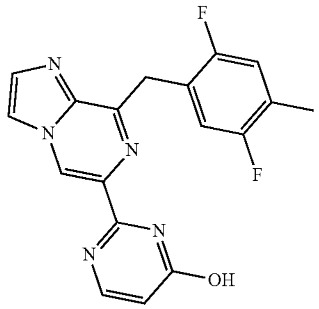 [SMILES: Cc1cc(F)c(Cc2nc(-c3nccc(O)n3)cn3ccnc23)cc1F]
I-15
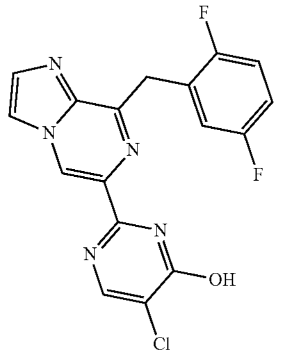 [SMILES: Oc1nc(-c2cn3ccnc3c(Cc3cc(F)ccc3F)n2)ncc1Cl]
I-16
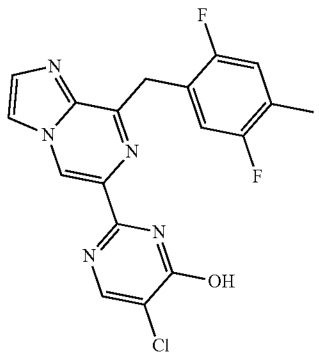 [SMILES: Cc1cc(F)c(Cc2nc(-c3ncc(Cl)c(O)n3)cn3ccnc23)cc1F]
I-17

TABLE II-continued
Exemplary sGC stimulators of the invention.
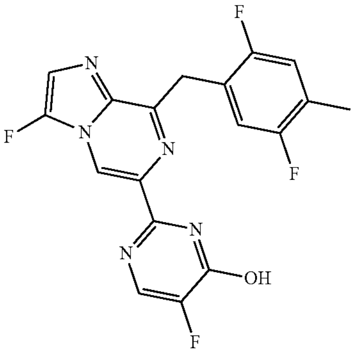 [SMILES: Cc1cc(F)c(Cc2nc(-c3ncc(F)c(O)n3)cn3c(F)cnc23)cc1F]
I-18
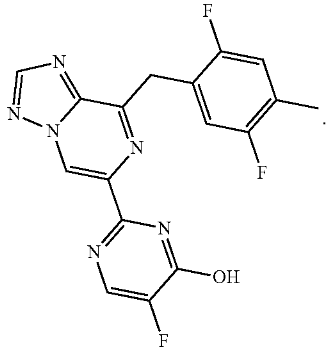 [SMILES: Cc1cc(F)c(Cc2nc(-c3ncc(F)c(O)n3)cn3ncnc23)cc1F]
I-19
In a third embodiment, the compound of the invention is selected from those depicted in Table III below:
TABLE III
Exemplary sGC stimulators of the invention.
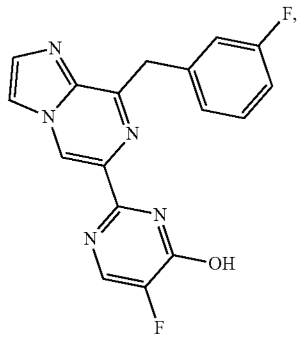 [SMILES: Oc1nc(-c2cn3ccnc3c(Cc3cccc(F)c3)n2)ncc1F]
I-1
TABLE III-continued
Exemplary sGC stimulators of the invention.
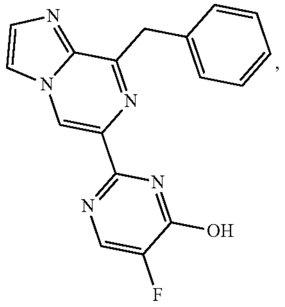 [SMILES: Oc1nc(-c2cn3ccnc3c(Cc3ccccc3)n2)ncc1F]
I-2
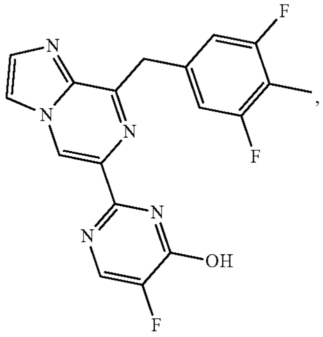 [SMILES: Cc1c(F)cc(Cc2nc(-c3ncc(F)c(O)n3)cn3ccnc23)cc1F]
I-3
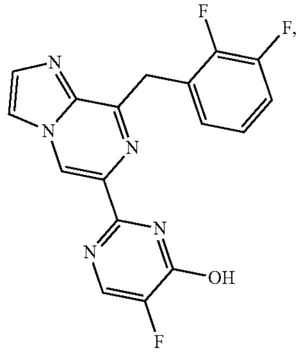 [SMILES: Oc1nc(-c2cn3ccnc3c(Cc3cccc(F)c3F)n2)ncc1F]
I-4
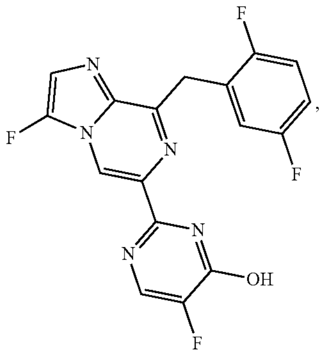
I-5

TABLE III-continued
Exemplary sGC stimulators of the invention.
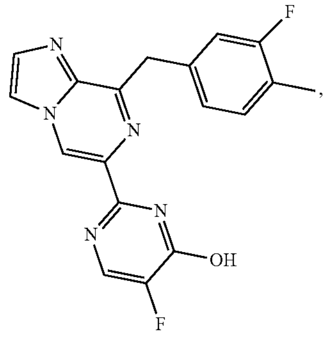 [SMILES: Cc1ccc(Cc2nc(-c3ncc(F)c(O)n3)cn3ccnc23)cc1F]
I-6
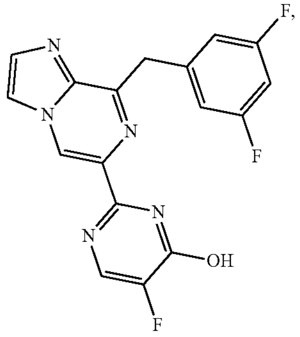 [SMILES: Oc1nc(-c2cn3ccnc3c(Cc3cc(F)cc(F)c3)n2)ncc1F]
I-7
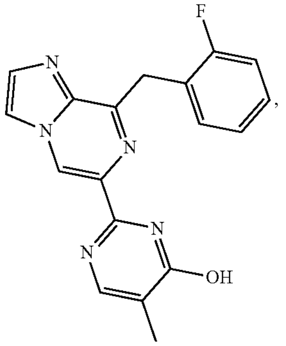 [SMILES: Cc1cnc(-c2cn3ccnc3c(Cc3ccccc3F)n2)nc1O]
I-8
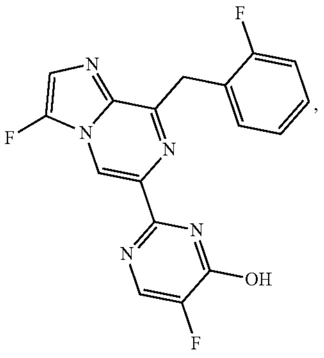 [SMILES: Oc1nc(-c2cn3c(F)cnc3c(Cc3ccccc3F)n2)ncc1F]
I-9
TABLE III-continued
Exemplary sGC stimulators of the invention.
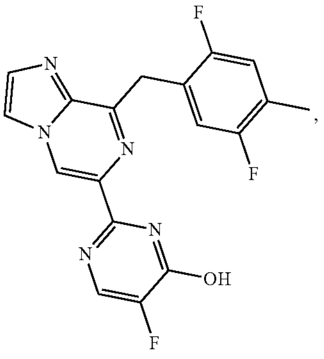 [SMILES: Cc1cc(F)c(Cc2nc(-c3ncc(F)c(O)n3)cn3ccnc23)cc1F]
I-14
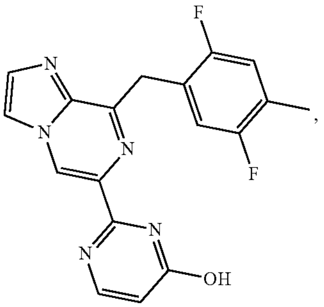 [SMILES: Cc1cc(F)c(Cc2nc(-c3nccc(O)n3)cn3ccnc23)cc1F]
I-15
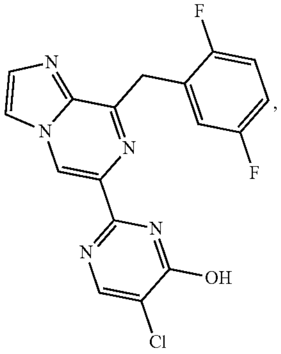 [SMILES: Oc1nc(-c2cn3ccnc3c(Cc3cc(F)ccc3F)n2)ncc1Cl]
I-16
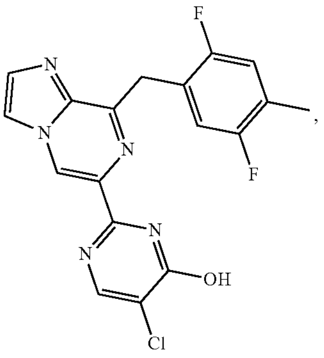 [SMILES: Cc1cc(F)c(Cc2nc(-c3ncc(Cl)c(O)n3)cn3ccnc23)cc1F]
I-17

TABLE III-continued

| Exemplary sGC stimulators of the invention. |
|---|
| 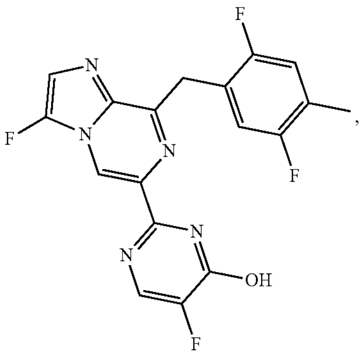 [SMILES: Cc1cc(F)c(Cc2nc(-c3ncc(F)c(O)n3)cn3c(F)cnc23)cc1F]<br>I-18<br>and<br>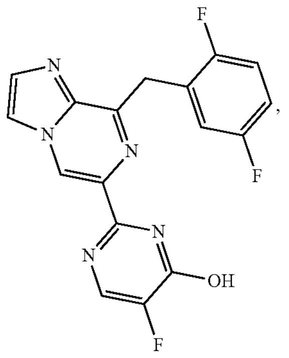 [SMILES: Oc1nc(-c2cn3ccnc3c(Cc3cc(F)ccc3F)n2)ncc1F]<br>I-20 |

or a pharmaceutically acceptable salt thereof.

In a fourth embodiment, the compound of the invention is selected from those depicted in Table IV below:

TABLE IV

| Exemplary sGC stimulators of the invention. |
|---|
| 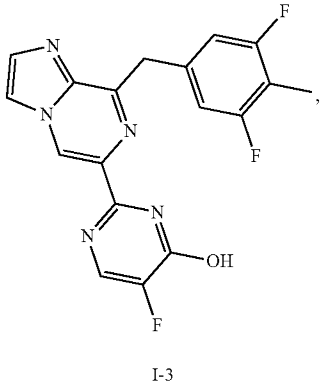<br>I-3 |

TABLE IV-continued

| Exemplary sGC stimulators of the invention. |
|---|
| 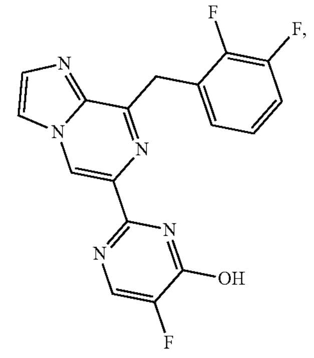 [SMILES: Oc1nc(-c2cn3ccnc3c(Cc3cccc(F)c3F)n2)ncc1F]<br>I-4 |
| 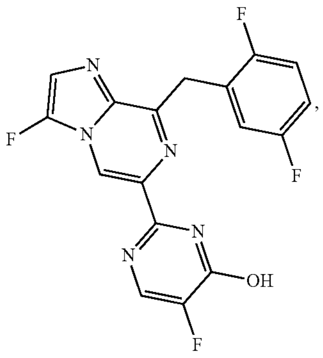<br>I-5 |
| 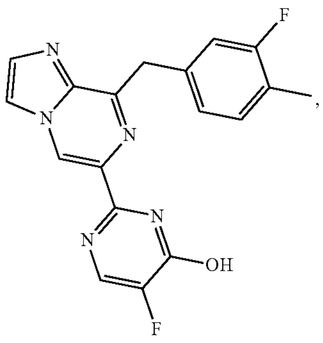 [SMILES: Cc1ccc(Cc2nc(-c3ncc(F)c(O)n3)cn3ccnc23)cc1F]<br>I-6 |
| 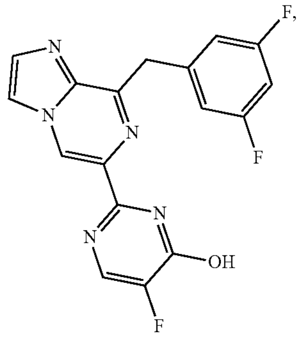 [SMILES: Oc1nc(-c2cn3ccnc3c(Cc3cc(F)cc(F)c3)n2)ncc1F]<br>I-7 |

TABLE IV-continued
| Exemplary sGC stimulators of the invention. |
| --- |
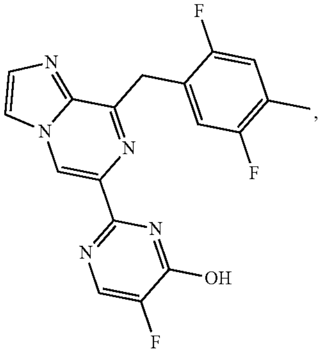 [SMILES: Cc1cc(F)c(Cc2nc(-c3ncc(F)c(O)n3)cn3ccnc23)cc1F]
I-14
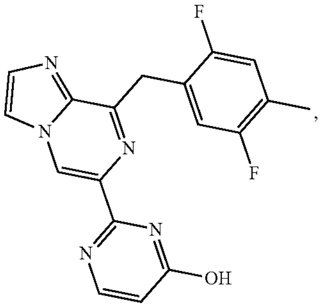 [SMILES: Cc1cc(F)c(Cc2nc(-c3nccc(O)n3)cn3ccnc23)cc1F]
I-15
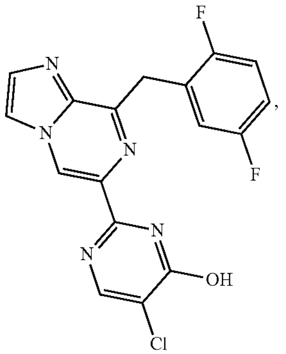 [SMILES: Oc1nc(-c2cn3ccnc3c(Cc3cc(F)ccc3F)n2)ncc1Cl]
I-16
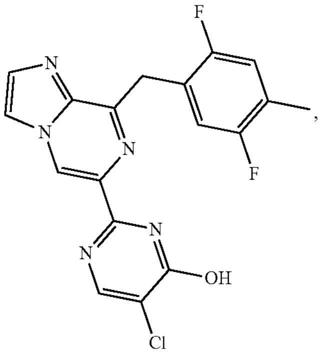 [SMILES: Cc1cc(F)c(Cc2nc(-c3ncc(Cl)c(O)n3)cn3ccnc23)cc1F]
I-17
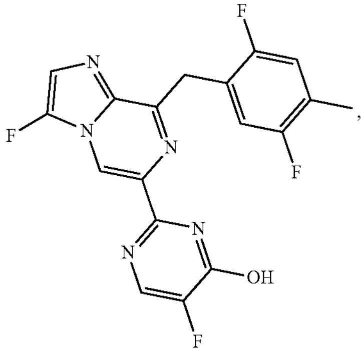 [SMILES: Cc1cc(F)c(Cc2nc(-c3ncc(F)c(O)n3)cn3c(F)cnc23)cc1F]
I-18
and
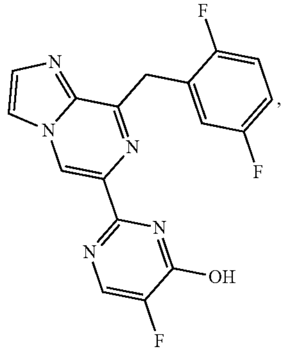 [SMILES: Oc1nc(-c2cn3ccnc3c(Cc3cc(F)ccc3F)n2)ncc1F]
I-20
or a pharmaceutically acceptable salt thereof.
In a fifth embodiment, the compound of the invention is selected from those depicted in Table V below:
TABLE V
| Exemplary sGC stimulators of the invention. |
| --- |
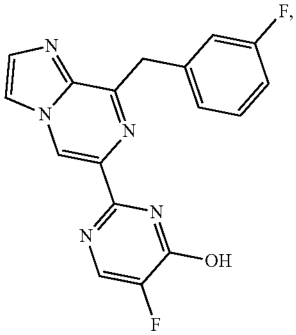 [SMILES: Oc1nc(-c2cn3ccnc3c(Cc3cccc(F)c3)n2)ncc1F]
I-1

TABLE V-continued
| Exemplary sGC stimulators of the invention. |
| --- |
| 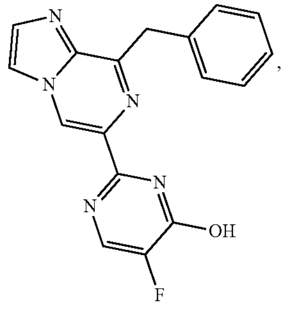 [SMILES: Oc1nc(-c2cn3ccnc3c(Cc3ccccc3)n2)ncc1F] |
| I-2 |
| 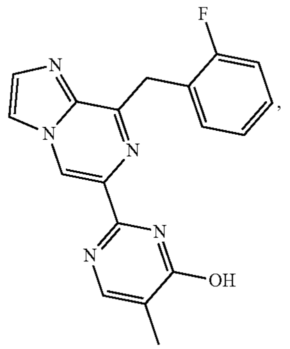 [SMILES: Cc1cnc(-c2cn3ccnc3c(Cc3ccccc3F)n2)nc1O] |
| I-8, |
| and |
| 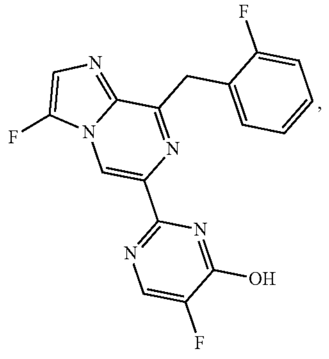 [SMILES: Oc1nc(-c2cn3c(F)cnc3c(Cc3ccccc3F)n2)ncc1F] |
| I-9 |
or a pharmaceutically acceptable salt thereof.
In a sixth embodiment, the compound of the invention is selected from those depicted in Table VI below:
TABLE VI
| Exemplary sGC stimulators of the invention. |
| --- |
| 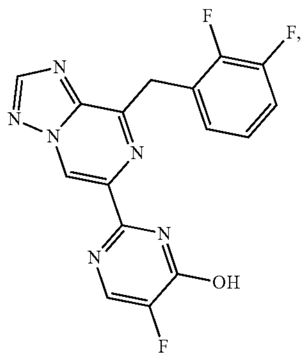 [SMILES: Oc1nc(-c2cn3ncnc3c(Cc3cccc(F)c3F)n2)ncc1F] |
| I-10 |
| 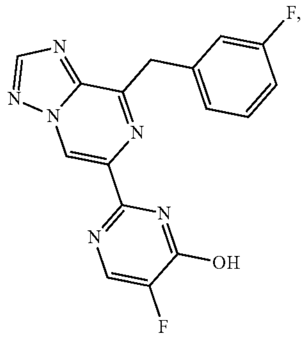 [SMILES: Oc1nc(-c2cn3ncnc3c(Cc3cccc(F)c3)n2)ncc1F] |
| I-11 |
| 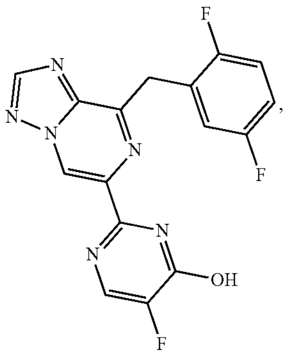 [SMILES: Oc1nc(-c2cn3ncnc3c(Cc3cc(F)ccc3F)n2)ncc1F] |
| I-12 |
| 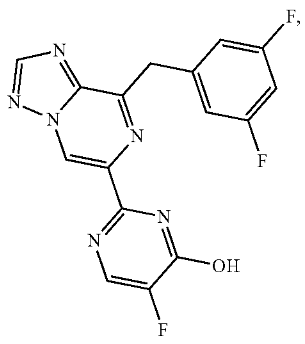 [SMILES: Oc1nc(-c2cn3ncnc3c(Cc3cc(F)cc(F)c3)n2)ncc1F] |
| I-13 |
| and |

TABLE VI-continued

| Exemplary sGC stimulators of the invention. |
|---|
| 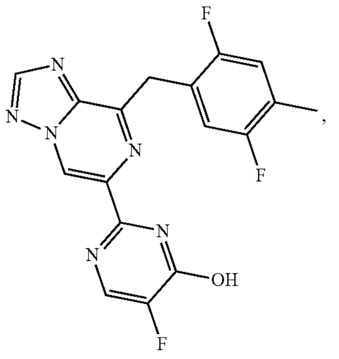 [SMILES: Cc1cc(F)c(Cc2nc(-c3ncc(F)c(O)n3)cn3ncnc23)cc1F] |
| I-19 |

or a pharmaceutically acceptable salt thereof.

In a seventh embodiment, the compound of the invention is compound I-14 or a pharmaceutically acceptable salt thereof. In one embodiment, the pharmaceutically acceptable salt of compound I-14 is the sodium salt. In another embodiment, the compound of the invention is the sodium salt of compound I-14 represented by the following formula:

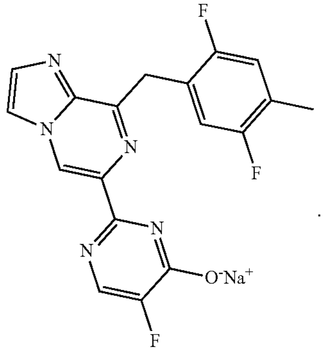

In an eighth embodiment, the compound of the invention is compound I-20 or a pharmaceutically acceptable salt thereof. In one embodiment, the pharmaceutically acceptable salt of compound I-20 is the sodium salt. In another embodiment, the compound of the invention is a sodium salt of compound I-20 represented by the following formula:

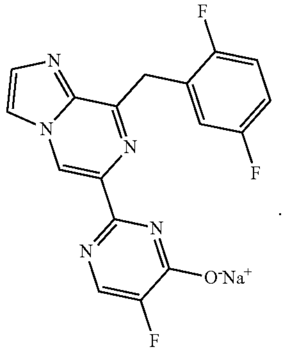

In a ninth embodiment, the compound of the invention is represented by Formula I:

Formula I

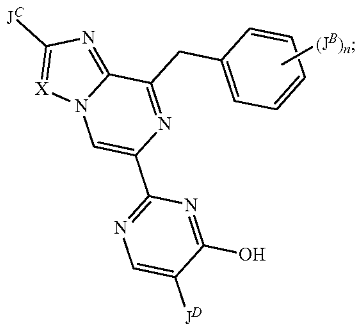

or a pharmaceutically acceptable salt thereof, wherein:

$J^C$ is selected from the group consisting of hydrogen, halogen $C_{1-6}$ alkyl and $C_{1-6}$ fluoroalkyl substituted with 1 to 3 fluoro atoms;

X is N or $C(J^{C1})$;

$J^{C1}$ is selected from the group consisting of hydrogen, halogen, $C_{1-6}$ alkyl and $C_{1-6}$ fluoroalkyl substituted with 1 to 3 fluoro atoms;

each $J^B$ is independently selected from the group consisting of hydrogen, halogen, $C_{1-6}$ alkyl and $C_{1-6}$ fluoroalkyl substituted with 1 to 3 fluoro atoms;

$J^D$ is selected from the group consisting of hydrogen, halogen, $C_{1-6}$ alkyl and $C_{1-6}$ fluoroalkyl substituted with 1 to 3 fluoro atoms; and n is an integer selected from 0, 1, 2, 3 or 4, provided that the compound is not one of the following:

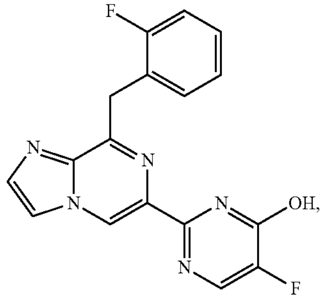

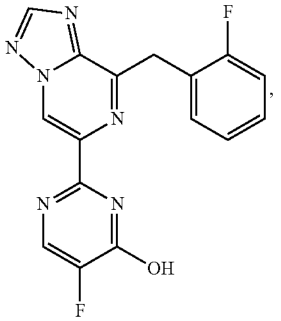

-continued

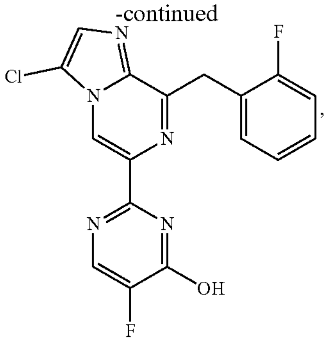

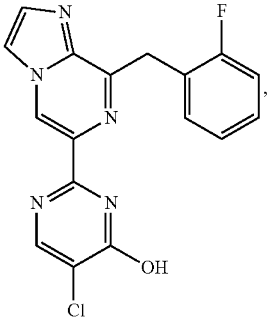

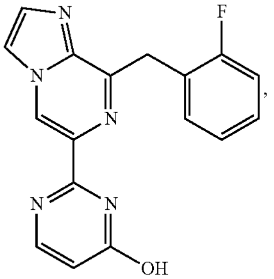

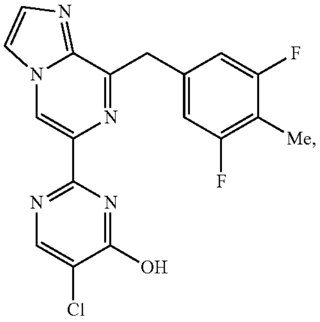

and

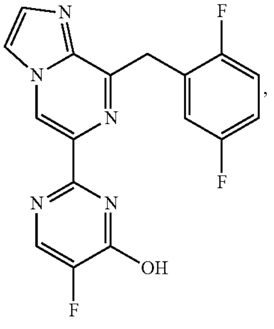

or a pharmaceutically acceptable salt thereof.

In a tenth embodiment, for a compound of Formula I described in the ninth embodiment, the variables are defined as follows:

$J^C$ is selected from the group consisting of hydrogen, halogen, and $C_{1-6}$ alkyl;

X is N or $C(J^{C1})$;

$J^{C1}$ is selected from the group consisting of hydrogen, halogen, and $C_{1-6}$ alkyl;

each $J^B$ is independently selected from the group consisting of hydrogen, halogen, and $C_{1-6}$ alkyl;

$J^D$ is selected from the group consisting of hydrogen, halogen, and $C_{1-6}$ alkyl; and n is an integer selected from 0, 1, 2, 3 or 4, provided that the compound is not one of the following:

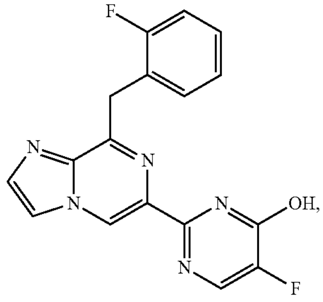

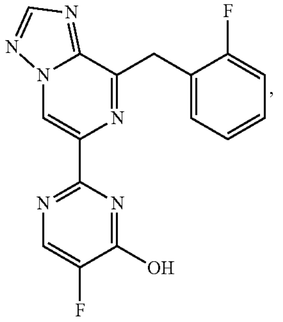

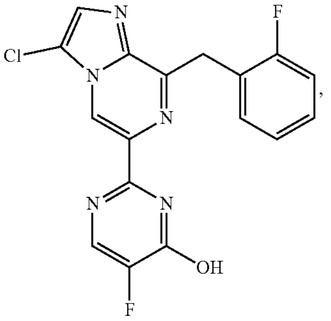

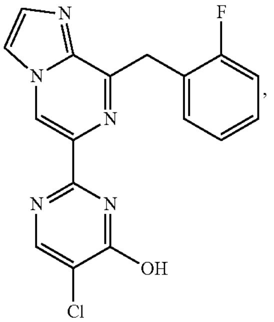

-continued

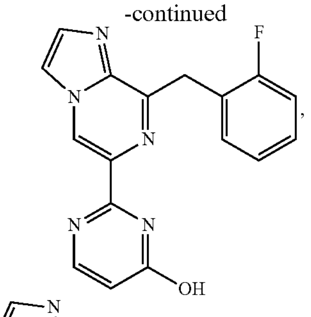

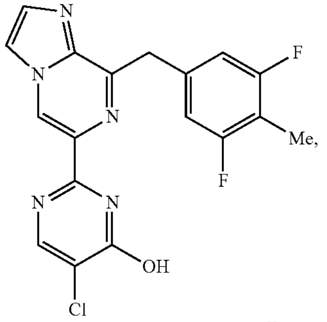 and

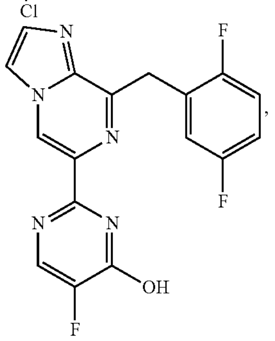

or a pharmaceutically acceptable salt thereof. In some embodiments, each $J^B$ is independently selected from the group consisting of halogen and $C_{1-6}$alkyl.

In a eleventh embodiment, for a compound of Formula I, n is an integer selected from 1, 2, 3 or 4, each $J^B$ is independently selected from the group consisting of halogen, $C_{1-6}$ alkyl and $C_{1-6}$ fluoroalkyl substituted with 1 to 3 fluoro atoms, all other carbon atoms of the phenyl ring where $J^B$ are attached are unsubstituted, and the remaining variables are as defined above in the ninth embodiment.

In an twelfth embodiment, the compound of Formula I is represented by Formula IA:

Formula IA

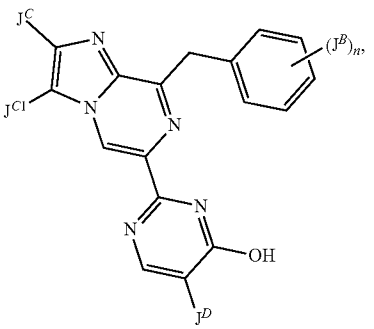

or a pharmaceutically acceptable salt thereof, wherein the variables are as described above for Formula I, in the ninth, tenth or eleventh embodiment, provided that the compound is not any one of the following:

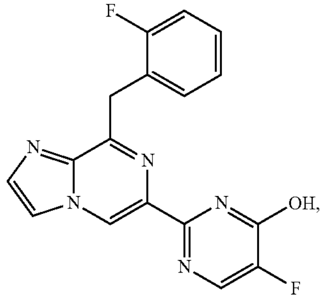

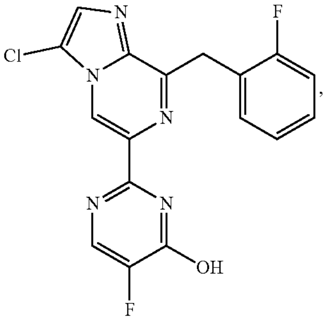

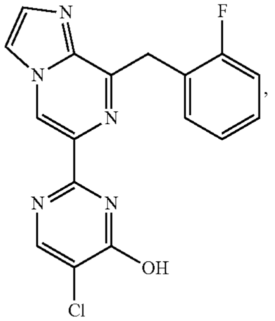

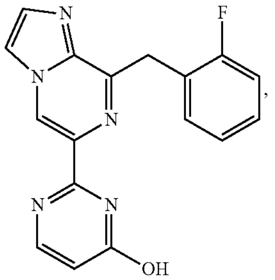

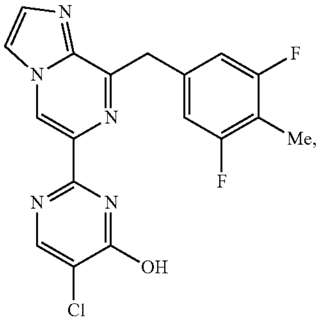 and

-continued

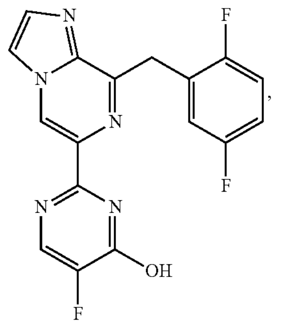

or a pharmaceutically acceptable salt thereof.

In a thirteenth embodiment, for the compound of Formula I or Formula IA, or a pharmaceutically acceptable salt thereof, $J^{C1}$ is H, F, Cl, $C_{1-2}$ alkyl or $C_{1-2}$ fluoroalkyl substituted with 1 to 3 fluoro atoms; and the remaining variables are as defined in any one of the ninth, eleventh or twelfth embodiments.

In a fourteenth embodiment, for the compound of Formula I or Formula IA, or a pharmaceutically acceptable salt thereof, $J^{C1}$ is H, F or Cl; and the remaining variables are as defined in any one of the ninth to twelfth embodiments.

In a fifteenth embodiment, for the compound of Formula I or Formula IA, or a pharmaceutically acceptable salt thereof, $J^{C1}$ is H, F, methyl or fluoromethyl substituted with 1 to 3 fluoro atoms (i.e., $—CH_2F$, $—CHF_2$ or $CF_3$); and the remaining variables are defined in any one of the ninth and eleventh to thirteenth embodiments.

In a sixteenth embodiment, for the compound of Formula I or Formula IA, or a pharmaceutically acceptable salt thereof, $J^{C1}$ is H; and the remaining variables are defined in any one of the ninth to fifteenth embodiments.

In a seventeenth embodiment, for the compound of Formula I or Formula IA, or a pharmaceutically acceptable salt thereof, $J^{C1}$ is F, methyl or fluoromethyl substituted with 1 to 3 fluoro atoms (i.e., $—CH_2F$, $—CHF_2$ or $CF_3$); and the remaining variables are defined in any one of the ninth, eleven to thirteen, and fifteenth embodiments.

In an eighteenth embodiment, for the compounds of Formula I or Formula IA, according to embodiment thirteenth, fifteenth or seventeenth, the $C_{1-2}$ fluoroalkyl or fluoromethyl group is substituted with one fluoro atom.

In a nineteenth embodiment, for the compounds of Formula I or Formula IA, according to embodiment thirteenth, fifteenth or seventeenth, the $C_{1-2}$ fluoroalkyl or fluoromethyl group is substituted with two fluoro atoms.

In a twentieth embodiment, for the compounds of Formula I or Formula IA, according to embodiment thirteenth, fifteenth or seventeenth, the $C_{1-2}$ fluoroalkyl or fluoromethyl group is substituted with three fluoro atoms.

In a twenty-first embodiment, for the compound of Formula I or Formula IA, or a pharmaceutically acceptable salt thereof, $J^{C1}$ is F or H; and the remaining variables are defined in any one of the ninth to twelfth embodiments.

In a twenty-second embodiment, the compound of Formula I is represented by Formula IB:

Formula IB

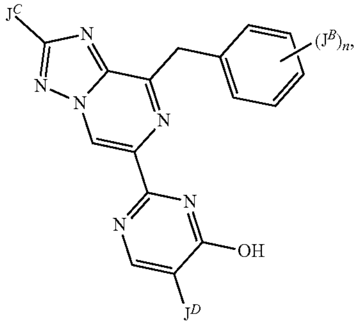

or a pharmaceutically acceptable salt thereof, wherein the variables are as described above for Formula I, according to embodiment ninthtenth, or eleventh, provided that the compound is not

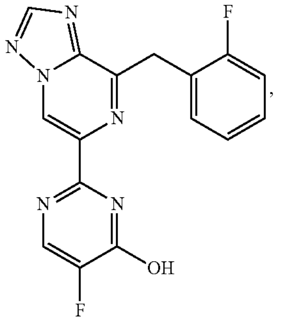 [SMILES: Oc1nc(-c2cn3ncnc3c(Cc3ccccc3F)n2)ncc1F]

or a pharmaceutically acceptable salt thereof.

In a twenty-third embodiment, for the compound of Formula I, IA or IB, or a pharmaceutically acceptable salt thereof, n is 2 or 3, and the remaining variables are as described in any one of the ninth, to twenty-second embodiments. In some embodiments, n is 2. In other embodiments, n is 3.

In a twenty-fourth embodiment, for the compound of Formula I, IA or IB, or a pharmaceutically acceptable salt thereof, n is 0 or 1, and the remaining variables are as described in any one of the ninth to twenty-second embodiments. In some embodiments, n is 1.

In a twenty-fifth embodiment, for the compound of Formula I, IA or IB, or a pharmaceutically acceptable salt thereof, each $J^B$ is independently H, F, $C_{1-4}$ alkyl or $C_{1-4}$ fluoroalkyl substituted with 1 to 3 fluoro atoms; and the remaining variables are as described in any one of the ninth to twenty-fourth embodiments.

In a twenty-sixth embodiment, for the compound of Formula I, IA or IB, or a pharmaceutically acceptable salt thereof, each $J^B$ is independently H, F or $C_{1-4}$ alkyl; and the remaining variables are as described in any one of the ninth to twenty-fourth embodiments.

In a twenty-seventh embodiment, for the compound of Formula I, IA or IB, or a pharmaceutically acceptable salt thereof, n is 2 or 3; each $J^B$ is independently F, methyl or fluoromethyl substituted with 1 to 3 fluoro atoms; and the remaining variables are as described in any one of the ninth to twenty-third embodiments.

In a twenty-eighth embodiment, for the compound of Formula I, IA or IB, or a pharmaceutically acceptable salt thereof, n is 2 or 3; each $J^B$ is independently F or methyl; and the remaining variables are as described in any one of the ninth to twenty-third embodiments.

In a twenty-ninth embodiment, for the compound of Formula I, IA or IB, or a pharmaceutically acceptable salt thereof, n is 2 or 3; each $J^B$ is independently F, ethyl or fluoroethyl substituted with 1 to 3 fluoro atoms; and the remaining variables are as described in any one of the ninth to twenty-third embodiments.

In a thirtieth embodiment, for the compound of Formula I, IA or IB, or a pharmaceutically acceptable salt thereof, n is 2; $J^B$ are both F or one of $J^B$ is F and the other is methyl or fluoromethyl substituted with 1 to 3 fluoro atoms; and the remaining variables are as described in any one of the ninth to twenty-third embodiments. In some embodiments, one $J^B$ is F and the other is methyl or fluoromethyl substituted with 1 to 3 atoms. In still other embodiments, one $J^B$ is F and the other is methyl. In yet other embodiments, one $J^B$ is F and the other is fluoromethyl. In some embodiments the fluoromethyl is substituted with one fluoro atom (i.e., $—CH_2F$). In other embodiments the fluoromethyl is substituted with two fluoro atoms (i.e., $—CHF_2$) and in other embodiments the fluoromethyl is substituted with three fluoro atoms (i.e., $—CF_3$).

In a thirty-first embodiment, for the compound of Formula I, IA or IB, or a pharmaceutically acceptable salt thereof, n is 2; $J^B$ are both F or one of $J^B$ is F and the other is ethyl or fluoroethyl substituted with 1 to 3 fluoro atoms; and the remaining variables are as described in any one of the ninth to twenty-third embodiments. In some embodiments, one $J^B$ is F and the other is ethyl or fluoroethyl substituted with 1 to 3 atoms. In still other embodiments, one $J^B$ is F and the other is ethyl. In yet other embodiments, one $J^B$ is F and the other is fluoroethyl. In some embodiments, the fluoroethyl is substituted with one fluoro atom. In other embodiments, the fluoroethyl is substituted with two fluoro atoms and in other embodiments the fluoroethyl is substituted with three fluoro atoms.

In a thirty-second embodiment, for the compound of Formula I, IA or IB, or a pharmaceutically acceptable salt thereof, n is 3; the three instances of $J^B$ are F or two of $J^B$ are F and the other is methyl or fluoromethyl substituted with 1 to 3 fluoro atoms; and the remaining variables are as described in any one of the ninth to twenty-third embodiments. In some embodiments the fluoromethyl is substituted with one fluoro atom (i.e., $—CH_2F$). In other embodiments the fluoromethyl is substituted with two fluoro atoms (i.e., $—CHF_2$) and in other embodiments the fluoromethyl is substituted with three fluoro atoms (i.e., $—CF_3$). In some embodiments, two of $J^B$ are F and the other is methyl.

In a thirty-third embodiment, for the compound of Formula I, IA or IB, or a pharmaceutically acceptable salt thereof, n is 3; the three instances of $J^B$ are F or two of $J^B$ are F and the other is ethyl or fluoroethyl substituted with 1 to 3 fluoro atoms; and the remaining variables are as described in any one of the ninth to twenty-third embodiments. In some embodiments the fluoroethyl is substituted with one fluoro atom. In other embodiments the fluoroethyl is substituted with two fluoro atoms and in other embodiments the fluoroethyl is substituted with three fluoro atoms.

In a thirty-fourth embodiment, for the compound of Formula I, IA or IB, or a pharmaceutically acceptable salt thereof, n is 1; $J^B$ is F, methyl, ethyl, fluoromethyl or fluoroethyl; and the remaining variables are as described in any one of the ninth to twenty-second embodiments. In some embodiments the fluoromethyl is substituted with one fluoro atom (i.e., $—CH_2F$). In other embodiments the fluoromethyl is substituted with two fluoro atoms (i.e., $—CHF_2$) and in other embodiments the fluoromethyl is substituted with three fluoro atoms (i.e., $—CF_3$). In some embodiments the fluoroethyl is substituted with one fluoro atom. In other embodiments the fluoroethyl is substituted with two fluoro atoms and in other embodiments the fluoroethyl is substituted with three fluoro atoms.

In a thirty-fifth embodiment, for the compound of Formula I, IA or IB, or a pharmaceutically acceptable salt thereof, n is 1; $J^B$ is F; and the remaining variables are as described in any one of the ninth to twenty-second embodiments.

In a thirty-sixth embodiment, for the compound of Formula I, IA or IB, or a pharmaceutically acceptable salt thereof, n is 0; and the remaining variables are as described in the ninth to twenty-second embodiments.

In a thirty-seventh embodiment, for the compound of Formula I, IA or IB, or a pharmaceutically acceptable salt thereof, $J^D$ is H, F, Cl, methyl, ethyl, or fluoromethyl or fluoroethyl, wherein said fluoromethyl or fluoroethyl is substituted with 1 to 3 fluoro atoms; and the remaining variables are as described in any one of the ninth to thirty-sixth embodiments. In some embodiments the fluoromethyl is substituted with two fluoro atoms (i.e., $—CHF_2$) and in other embodiments the fluoromethyl is substituted with three fluoro atoms (i.e., $—CF_3$). In other embodiments the fluoroethyl is substituted with one fluoro atom. In other embodiments the fluoroethyl is substituted with two fluoro atoms and in other embodiments the fluoroethyl is substituted with three fluoro atoms.

In a thirty-eighth embodiment, for the compound of Formula I, IA or IB, or a pharmaceutically acceptable salt thereof, $J^D$ is H or F, and all other variables are as defined in any one of the ninth to the thirty-seventh embodiments. In some embodiments, $J^D$ is F. In some embodiments, $J^D$ is H.

In a thirty-ninth embodiment, for the compound of Formula I, IA or IB, or a pharmaceutically acceptable salt thereof, $J^D$ is hydrogen; and the remaining variables are as described in any one of the ninth to thirty-seventh embodiments.

In a fortieth embodiment, for the compound of Formula I, IA or IB, or a pharmaceutically acceptable salt thereof, $J^D$ is F; and the remaining variables are as described in any one of the ninth to thirty-seventh embodiments.

In a forty-first embodiment, for the compound of Formula I, IA or IB, or a pharmaceutically acceptable salt thereof, $J_C$ is H, Cl, F, methyl, ethyl, fluoroethyl or fluoromethyl substituted with 1 to 3 fluoroatoms; and the remaining variables are as described in any one of the ninth to fortieth embodiments. In some embodiments, the fluoromethyl is substituted with two fluoro atoms (i.e., $—CHF_2$) and in other embodiments, the fluoromethyl is substituted with three fluoro atoms (i.e., $—CF_3$). In other embodiments, the fluoroethyl is substituted with one fluoro atom. In other embodiments the fluoroethyl is substituted with two fluoro atoms and in other embodiments the fluoroethyl is substituted with three fluoro atoms.

In a forty-second embodiment, for the compound of Formula I, IA or IB, or a pharmaceutically acceptable salt thereof, $J^C$ is H, Cl or F; and the remaining variables are as described in any one of the ninth to fortieth embodiments.

In a forty-third embodiment, for the compound of Formula I, IA or IB, or a pharmaceutically acceptable salt thereof, $J^C$ is H, F, methyl or fluoromethyl; and the remaining variables are as described in any one of the ninth to fortieth embodiments. In some embodiments, the fluoromethyl is substituted with two fluoro atoms (i.e., $—CHF_2$) and in other embodiments the fluoromethyl is substituted with three fluoro atoms (i.e., $-CF_3$).

In a forty-fourth embodiment, for the compound of Formula I, IA or IB, or a pharmaceutically acceptable salt thereof, $J^C$ is H or F; and the remaining variables are as described in any one of the ninth to fortieth embodiments. In some embodiments, $J^C$ is H.

In a forty-fifth embodiment, the compound of the present invention is a compound represented by Formula IC:

Formula IC

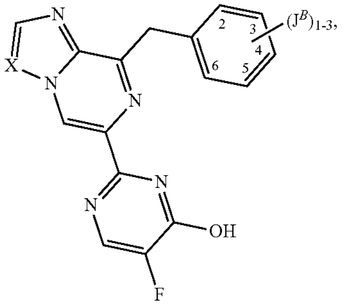

or a pharmaceutically acceptable salt thereof, wherein X is N or $C(J^{C1})$, wherein when X is $C(J^{C1})$, it is represented by C in the below table; and the definitions for variables X, $J^{C1}$ and $J^B$ are described in the Table below; further where Me represents a methyl group and Me-F represents a fluorinated methyl group substituted by 1 to 3 fluoro atoms (i.e, $-CH_2F$, $-CHF_2$ or $CF_3$);

| Compound | position of $J^B$ on the phenyl ring and $J^B$ definition | | | | | | |
|---|---|---|---|---|---|---|---|
| No. | 2 | 3 | 4 | 5 | 6 | X | $J^{C1}$ |
| I-27 | | F | | | | C | F |
| I-28 | | | F | | | C | H |
| I-29 | | | F | | | N | — |
| I-30 | | | F | | | C | F |
| I-31 | F | F | | | | C | F |
| I-32 | F | | F | | | C | H |
| I-33 | F | | F | | | N | — |
| I-34 | F | | F | | | C | F |
| I-35 | F | | | | F | C | H |
| I-36 | F | | | | F | N | — |
| I-37 | F | | | | F | C | F |
| I-38 | | F | F | | | C | H |
| I-39 | | F | F | | | N | — |
| I-40 | | F | F | | | C | F |
| I-41 | | F | | F | | C | F |
| I-42 | | F | | | F | C | H |
| I-43 | | F | | | F | N | — |
| I-44 | | F | | | F | C | F |
| I-45 | F | Me | | | | C | H |
| I-46 | F | Me | | | | N | — |
| I-47 | F | Me | | | | C | F |
| I-48 | Me | F | | | | C | H |
| I-49 | Me | F | | | | N | — |
| I-50 | Me | F | | | | C | F |
| I-51 | F | | Me | | | C | H |
| I-52 | F | | Me | | | N | — |
| I-53 | F | | Me | | | C | F |
| I-54 | Me | | F | | | C | H |
| I-55 | Me | | F | | | N | — |
| I-56 | Me | | F | | | C | F |
| I-57 | F | | | Me | | C | H |
| I-58 | F | | | Me | | C | F |
| I-59 | F | | | Me | | N | — |
| I-60 | Me | | | F | | C | H |
| I-61 | Me | | | F | | C | F |

-continued

| Compound | position of $J^B$ on the phenyl ring and $J^B$ definition | | | | | | |
|---|---|---|---|---|---|---|---|
| No. | 2 | 3 | 4 | 5 | 6 | X | $J^{C1}$ |
| I-62 | Me | | | F | | N | — |
| I-63 | F | | | | Me | C | H |
| I-64 | F | | | | Me | N | — |
| I-65 | F | | | | Me | C | F |
| I-66 | Me | | | | F | C | H |
| I-67 | Me | | | | F | N | — |
| I-68 | Me | | | | F | C | F |
| I-69 | | F | Me | | | N | — |
| I-70 | | F | Me | | | C | F |
| I-71 | | Me | F | | | C | H |
| I-72 | | Me | F | | | N | — |
| I-73 | | Me | F | | | C | F |
| I-74 | | F | | Me | | C | H |
| I-75 | | F | | Me | | N | — |
| I-76 | | F | | Me | | C | F |
| I-77 | | Me | | F | | C | H |
| I-78 | | Me | | F | | N | — |
| I-79 | | Me | | F | | C | F |
| I-80 | | Me | | | F | C | H |
| I-81 | | Me | | | F | N | — |
| I-82 | | Me | | | F | C | F |
| I-83 | | F | | | Me | C | H |
| I-84 | | F | | | Me | N | — |
| I-85 | | F | | | Me | C | F |
| I-86 | F | F | Me | | | C | H |
| I-87 | F | F | Me | | | N | — |
| I-88 | F | F | Me | | | C | F |
| I-89 | F | F | | Me | | C | H |
| I-90 | F | F | | Me | | N | — |
| I-91 | F | F | | Me | | C | F |
| I-92 | F | F | | | Me | C | H |
| I-93 | F | F | | | Me | N | — |
| I-94 | F | F | | | Me | C | F |
| I-95 | F | Me | F | | | C | H |
| I-96 | F | Me | F | | | N | — |
| I-97 | F | Me | F | | | C | F |
| I-98 | F | | F | Me | | C | H |
| I-99 | F | | F | Me | | N | — |
| I-100 | F | | F | Me | | C | F |
| I-101 | F | | F | | Me | C | H |
| I-102 | F | | F | | Me | N | — |
| I-103 | F | | F | | Me | C | F |
| I-104 | F | Me | | F | | C | H |
| I-105 | F | Me | | F | | C | F |
| I-106 | F | Me | | F | | N | — |
| I-107 | F | | | F | Me | C | H |
| I-108 | F | | | F | Me | C | F |
| I-109 | F | | | F | Me | N | — |
| I-110 | F | Me | | | F | C | H |
| I-111 | F | Me | | | F | N | — |
| I-112 | F | Me | | | F | C | F |
| I-113 | F | | Me | | F | C | H |
| I-114 | F | | Me | | F | N | — |
| I-115 | F | | Me | | F | C | F |
| I-116 | Me | F | F | | | C | H |
| I-117 | Me | F | F | | | N | — |
| I-118 | Me | F | F | | | C | F |
| I-119 | | F | F | Me | | C | H |
| I-120 | | F | F | Me | | N | — |
| I-121 | | F | F | Me | | C | F |
| I-122 | | F | F | | Me | C | H |
| I-123 | | F | F | | Me | N | — |
| I-124 | | F | F | | Me | C | F |
| I-125 | Me | F | | F | | C | H |
| I-126 | Me | F | | F | | N | — |
| I-127 | Me | F | | F | | C | F |
| I-128 | | F | Me | F | | N | — |
| I-129 | | F | Me | F | | C | F |
| I-130 | F | Me—F | | | | C | H |
| I-131 | F | Me—F | | | | N | — |
| I-132 | F | Me—F | | | | C | F |
| I-133 | Me—F | F | | | | C | H |
| I-134 | Me—F | F | | | | N | — |
| I-135 | Me—F | F | | | | C | F |

-continued

| Compound | position of $J^B$ on the phenyl ring and $J^B$ definition | | | | | | |
|---|---|---|---|---|---|---|---|
| No. | 2 | 3 | 4 | 5 | 6 | X | $J^{C1}$ |
| I-136 | F | | Me—F | | | C | H |
| I-137 | F | | Me—F | | | N | — |
| I-138 | F | | Me—F | | | C | F |
| I-139 | Me—F | | F | | | C | H |
| I-140 | Me—F | | F | | | N | — |
| I-141 | Me—F | | F | | | C | F |
| I-142 | F | | | Me—F | | C | H |
| I-143 | F | | | Me—F | | C | F |
| I-144 | F | | | Me—F | | N | — |
| I-145 | Me—F | | | F | | C | H |
| I-146 | Me—F | | | F | | C | F |
| I-147 | Me—F | | | F | | N | — |
| I-148 | F | | | | Me—F | C | H |
| I-149 | F | | | | Me—F | N | — |
| I-150 | F | | | | Me—F | C | F |
| I-151 | Me—F | | | | F | C | H |
| I-152 | Me—F | | | | F | N | — |
| I-153 | Me—F | | | | F | C | F |
| I-154 | | F | Me—F | | | N | — |
| I-155 | | F | Me—F | | | C | F |
| I-156 | | F | Me—F | | | C | H |
| I-157 | | Me—F | F | | | N | — |
| I-158 | | Me—F | F | | | C | H |
| I-159 | | Me—F | F | | | C | F |
| I-160 | | F | | Me—F | | C | H |
| I-161 | | F | | Me—F | | N | — |
| I-162 | | F | | Me—F | | C | F |
| I-163 | | Me—F | | F | | C | H |
| I-164 | | Me—F | | F | | N | — |
| I-165 | | Me—F | | F | | C | F |
| I-166 | | Me—F | | | F | C | H |
| I-167 | | Me—F | | | F | N | — |
| I-168 | | Me—F | | | F | C | F |
| I-169 | | F | | | Me—F | C | H |
| I-170 | | F | | | Me—F | N | — |
| I-171 | | F | | | Me—F | C | F |
| I-172 | F | F | Me—F | | | C | H |
| I-173 | F | F | Me—F | | | N | — |
| I-174 | F | F | Me—F | | | C | F |
| I-175 | F | F | | Me—F | | C | H |
| I-176 | F | F | | Me—F | | N | — |
| I-177 | F | F | | Me—F | | C | F |
| I-178 | F | F | | | Me—F | C | H |
| I-179 | F | F | | | Me—F | N | — |
| I-180 | F | F | | | Me—F | C | F |
| I-181 | F | Me—F | F | | | C | H |
| I-182 | F | Me—F | F | | | N | — |
| I-183 | F | Me—F | F | | | C | F |
| I-184 | F | | F | Me—F | | C | H |
| I-185 | F | | F | Me—F | | N | — |
| I-186 | F | | F | Me—F | | C | F |
| I-187 | F | | F | | Me—F | C | H |
| I-188 | F | | F | | Me—F | N | — |
| I-189 | F | | F | | Me—F | C | F |
| I-190 | F | Me—F | | F | | C | H |
| I-191 | F | Me—F | | F | | C | F |
| I-192 | F | Me—F | | F | | N | — |
| I-193 | F | | | F | Me—F | C | H |
| I-194 | F | | | F | Me—F | C | F |
| I-195 | F | | | F | Me—F | N | — |
| I-196 | F | Me—F | | | F | C | H |
| I-197 | F | Me—F | | | F | N | — |
| I-198 | F | Me—F | | | F | C | F |
| I-199 | F | | Me—F | | F | C | H |
| I-200 | F | | Me—F | | F | N | — |
| I-201 | F | | Me—F | | F | C | F |
| I-202 | Me—F | F | F | | | C | H |
| I-203 | Me—F | F | F | | | N | — |
| I-204 | Me—F | F | F | | | C | F |
| I-205 | | F | F | Me—F | | C | H |
| I-206 | | F | F | Me—F | | N | — |
| I-207 | | F | F | Me—F | | C | F |
| I-208 | | F | F | | Me—F | C | H |
| I-209 | | F | F | | Me—F | N | — |
| I-210 | | F | F | | Me—F | C | F |
| I-211 | Me—F | F | | F | | C | H |
| I-212 | Me—F | F | | F | | N | — |
| I-213 | Me—F | F | | F | | C | F |
| I-214 | | F | Me—F | F | | N | — |
| I-215 | | F | Me—F | F | | C | F |
| I-216 | | F | Me—F | F | | C | H |

Pharmaceutically Acceptable Salts of the Invention.

A "pharmaceutically acceptable salt" of the compounds described herein include those derived from said compounds when mixed with inorganic or organic acids or bases. In some embodiments, the salts can be prepared in situ during the final isolation and purification of the compounds. In other embodiments the salts can be prepared from the free form of the compound in a separate synthetic step. The preparation of the pharmaceutically acceptable salts described above and other typical pharmaceutically acceptable salts is more fully described by Berg et al., "Pharmaceutical Salts," J. Pharm. Sci., 1977:66:1-19, incorporated here by reference in its entirety. The pharmaceutically acceptable salts of a compound of any one of Tables I-VI or Formula I are those that may be used in medicine. Salts that are not pharmaceutically acceptable may, however, be useful in the preparation of a compounds of Tables I-VI, or Formula I or of their pharmaceutically acceptable salts.

When a compound described herein (e.g., a compound of Tables I-VI or a compound represented by Formula I) is acidic, suitable "pharmaceutically acceptable salts" refers to salts prepared from pharmaceutically acceptable non-toxic bases including inorganic and organic bases. Salts derived from inorganic bases include aluminum, ammonium, calcium, copper, ferric, ferrous, lithium, magnesium, manganic, manganous, potassium, sodium, zinc and the like. Particular embodiments include ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines, arginine, betaine, caffeine, choline, N,$N^1$-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

In some embodiments, compounds of the present invention have an acidic OH group that can react with a base (e.g., a pharmaceutically acceptable non-toxic base) to form a salt (e.g., a pharmaceutically acceptable salt). In some embodiments, the salt is an ammonium, calcium, magnesium, potassium or sodium salt. In some embodiments, the salt is a sodium salt.

When a compound described herein (e.g., a compound of Tables I-VI or a compound represented by Formula I) is basic, salts may be prepared from pharmaceutically acceptable non-toxic acids, including inorganic and organic acids. Such acids include acetate, acetic, acid citrate, acid phosphate, ascorbate, benzenesulfonic, benzenesulfonate, benzoic, benzoate, bromide, bisulfate, bitartrate, camphorsulfonic, chloride, citrate, citric, ethanesulfonate, ethanesulfonic, formate, fumarate, fumaric, gentisinate, gluconate, gluconic, glucuronate, glutamate, glutamic, hydrobromic, hydrochloric, iodide, isethionic, isonicotinate, lactate, lactic, maleate, maleic, malic, mandelic, methanesulfonic, methanesulfonate, mucic, nitrate, nitric, oleate, oxalate, pamoic, pamoate (i.e., 1,1'-methylene-bis-(2-hydroxy-3-naphthoate)), pantothenic, pantothenate, phosphate, phosphoric, saccharate, salicylate, succinic, succinate, sulfuric, sulfate, tannate, tartrate, tartaric, p-toluenesulfonate, p-toluenesulfonic acid and the like. Particular embodiments include citric, hydrobromic, hydrochloric, maleic, phosphoric, sulfuric and tartaric acids.

In addition to the compounds described herein, their pharmaceutically acceptable salts may also be employed in compositions to treat or prevent the herein identified diseases.

Pharmaceutical Compositions and Methods of Administration.

In a second aspect, the invention relates to pharmaceutical compositions comprising a compound described herein (e.g., a compound of Tables I-VI or a compound represented by Formula I, or a pharmaceutically acceptable salt thereof) and at least one pharmaceutically acceptable excipient or carrier.

In some embodiments, the pharmaceutical composition of the present invention comprises a compound according of any one of the compounds as described in the first, second, third, fourth, fifth, sixth, seventh, eighth, ninth, tenth, eleventh, twelfth, thirteen, fourteenth, fifteenth, sixteenth, seventeenth, eighteenth, nineteenth, twentieth, twenty-first, twenty-second, twenty-third, twenty-fourth, twenty-fifth, twenty-sixth, twenty-seventh and twenty-eighth embodiments, or a pharmaceutically acceptable salt thereof, and at least one pharmaceutically acceptable excipient or carrier.

The compounds herein disclosed, and their pharmaceutically acceptable salts thereof may be formulated as pharmaceutical compositions or "formulations".

A typical formulation is prepared by mixing a compound described herein (e.g., a compound of Tables I-VI or a compound represented by Formula I, or a pharmaceutically acceptable salt thereof), and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which a compound described herein (e.g., a compound of Tables I-VI or a compound represented by Formula I, or a pharmaceutically acceptable salt thereof) is being formulated. Solvents are generally selected based on solvents recognized by persons skilled in the art as safe (GRAS-Generally Regarded as Safe) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include other types of excipients such as one or more buffers, stabilizing agents, antiadherents, surfactants, wetting agents, lubricating agents, emulsifiers, binders, suspending agents, disintegrants, fillers, sorbents, coatings (e.g. enteric or slow release) preservatives, antioxidants, opaquing agents, glidants, processing aids, colorants, sweeteners, perfuming agents, flavoring agents and other known additives to provide an elegant presentation of the drug (i.e., a compound of Tables I-VI, a compound represented by Formula I or pharmaceutical composition thereof) or aid in the manufacturing of the pharmaceutical product (i.e., medicament).

Acceptable diluents, carriers, excipients, and stabilizers are those that are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, e.g., hydroxymethylcellulose or gelatin-microcapsules and poly-(methylmethacylate) microcapsules, respectively; in colloidal drug delivery systems (for example, liposomes, albumin microspheres, microemulsions, nano-particles and nanocapsules) or in macroemulsions. Such techniques are disclosed in Remington's: The Science and Practice of Pharmacy, 21$^{st}$ Edition, University of the Sciences in Philadelphia, Eds., 2005 (hereafter "Remington's").

The formulations may be prepared using conventional dissolution and mixing procedures.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. The therapeutically effective amount of the compound to be administered will be governed by such considerations, and is the minimum amount necessary to ameliorate, cure or treat the disease, or one or more of its symptoms.

The terms "administer", "administering" or "administration" in reference to a compound, composition or dosage form of the invention means introducing the compound, composition or dosage form into the system of the subject or patient in need of treatment. When a compound of the invention is provided in combination with one or more other active agents, "administration" and its variants are each understood to include concurrent and/or sequential introduction of the compound, composition or dosage form and the other active agents.

The compositions described herein may be administered systemically or locally, e.g. orally (including, but not limited to solid dosage forms including hard or soft capsules (e.g. gelatin capsules), tablets, pills, powders, sublingual tablets, troches, lozenges, and granules; and liquid dosage forms including, but are not limited to, pharmaceutically acceptable emulsions, microemulsions, aqueous or oil solutions, suspensions, syrups and elixirs, by inhalation (e.g. with an aerosol, gas, inhaler, nebulizer or the like), to the ear (e.g.

using ear drops), topically (e.g. using creams, gels, inhalants, liniments, lotions, ointments, patches, pastes, powders, solutions, sprays, transdermal patches, etc.), ophthalmically (e.g. with eye drops, ophthalmic gels, ophthalmic ointments), rectally (e.g. using enemas or suppositories), nasally, buccally, vaginally (e.g. using douches, intrauterine devices, vaginal suppositories, vaginal rings or tablets, etc.), via ear drops, via an implanted reservoir or the like, or parenterally depending on the severity and type of the disease being treated. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Formulations of a compound intended for oral use may be prepared according to any method known in the art for the manufacture of pharmaceutical compositions.

In solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. Tablets may be uncoated or may be coated by known techniques including microencapsulation to mask an unpleasant taste or to delay disintegration and adsorption in the gastrointestinal tract and thereby provide a sustained action over a longer period. For example, a time delay material such as glyceryl monostearate or glyceryl distearate alone or with a wax may be employed. A water soluble taste masking material such as hydroxypropyl-methylcellulose or hydroxypropyl-cellulose may be employed.

In addition to the active compounds, liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Oral compositions (either solid or liquid) can also include excipients and adjuvants such as dispersing or wetting agents, such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate); emulsifying and suspending agents, such as sodium carboxymethylcellulose, croscarmellose, povidone, methylcellulose, hydroxypropyl methylcelluose, sodium alginate, polyvinylpyrrolidone, gum tragacanth and gum acacia; sweetening, flavoring, and perfuming agents; and/or one or more preservatives such as ethyl or n-propyl p-hydroxy-benzoate, one or more coloring agents, one or more flavoring agents and one or more sweetening agents, such as sucrose or saccharin.

The pharmaceutical compositions may also be administered by nasal aerosol or by inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. Formulations suitable for intrapulmonary or nasal administration have a particle size for example in the range of 0.1 to 500 micros (including particles in a range between 0.1 and 500 microns in increments microns such as 0.5, 1, 30, 35 microns, etc.) which is administered by rapid inhalation through the nasal passage or by inhalation through the mouth so as to reach the alveolar sacs.

The pharmaceutical compositions described herein may also be administered topically, especially when the target of treatment includes areas or organs readily accessible by topical application, including diseases of the eye, the ear, the skin, or the lower intestinal tract. Suitable topical formulations are readily prepared for each of these areas or organs. The active component is admixed under sterile conditions with a pharmaceutically acceptable carrier and any needed preservatives or buffers as may be required.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

Alternatively, the active ingredients may be formulated in a cream with an oil-in-water cream base. If desired, the aqueous phase of the cream base may include a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of emulsions prepared using a compound of Tables I-VI or Formula I may be constituted from known ingredients in a known manner. While the phase may comprise merely an emulsifier (otherwise known as an emulgent), it desirably comprises a mixture of at least one emulsifier with a fat or an oil or with both a fat and an oil. A hydrophilic emulsifier may be included together with a lipophilic emulsifier which acts as a stabilizer. In some embodiments, the emulsifier includes both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulgents and emulsion stabilizers suitable for use in the formulation of a compound of Tables I-VI or Formula I include Tween™-60, Span™-80, cetostearyl alcohol, benzyl alcohol, myristyl alcohol, glyceryl mono-stearate and sodium lauryl sulfate.

Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum. For treatment of the eye or other external tissues, e.g., mouth and skin, the formulations may be applied as a topical ointment or cream containing the active ingredient(s) in an amount of, for example, 0.075 to 20% w/w. When formulated in an ointment, the active ingredients may be employed with either an oil-based, paraffinic or a water-miscible ointment base.

Compositions for rectal or vaginal administration are preferably suppositories which can be prepared by mixing the compounds described herein with suitable non-irritating excipients or carriers such as cocoa butter, beeswax, polyethylene glycol or a suppository wax which are solid at ambient temperature but liquid at body temperature and therefore melt in the rectum or vaginal cavity and release the active compound. Other formulations suitable for vaginal administration may be presented as pessaries, tampons, creams, gels, pastes, foams or sprays.

Sterile injectable forms of the compositions described herein (e.g. for parenteral administration) may be aqueous or oleaginous suspension. These suspensions may be formulated according to techniques known in the art using suitable dispersing or wetting agents and suspending agents (including those described in the preceding paragraph). The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as a vegetable oil, for example *arachis* oil, olive oil, sesame oil or coconut oil, especially in their polyoxyethylated versions, or in mineral oil such as liquid paraffin. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of injectable formulations. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

In another aspect, a compound of Tables I-VI or Formula I or a pharmaceutically acceptable salt thereof may be formulated in a veterinary composition comprising a veterinary carrier. Veterinary carriers are materials useful for the purpose of administering the composition and may be solid, liquid or gaseous materials which are otherwise inert. In the veterinary art and are compatible with the active ingredient. These veterinary compositions may be administered parenterally, orally or by any other desired route.

Therapeutic Methods

In another aspect, the invention also provides a method of treating a disease in a subject in need thereof, comprising administering, alone or in combination therapy, a therapeutically effective amount of a compound of Tables I-VI or Formula I or a pharmaceutically acceptable salt thereof to the subject; wherein the disease is one that benefits from sGC stimulation or from an increase in the concentration of NO or cGMP or both, or from the upregulation of the NO-sGC-cGMP pathway. The invention also provides a method of treating a disease in a subject in need thereof, comprising administering, alone or in combination therapy, a pharmaceutical composition or a dosage form comprising a compound of Tables I-VI or Formula I, or a pharmaceutically acceptable salt thereof to the subject, wherein the disease is one that benefits from sGC stimulation or from an increase in the concentration of NO or cGMP or both, or from the upregulation of the NO-sGC-cGMP pathway.

A tenth embodiment of the invention is a method of treating a disease in a subject in need of treatment, comprising administering a therapeutically effective amount of a compound of any one of the compounds as described in the first, second, third, fourth, fifth, sixth, seventh, or eighth embodiment, or a pharmaceutically acceptable salt thereof, or a pharmaceutical composition as described in the ninth embodiment, to the subject in need of treatment.

In some embodiments, the compounds here disclosed are sGC stimulators that may be useful in the prevention and/or treatment of diseases characterized by undesirable reduced bioavailability of and/or sensitivity to NO, such as those associated with conditions of oxidative stress or nitrosative stress.

Increased concentration of cGMP leads to vasodilation, inhibition of platelet aggregation and adhesion, anti-hypertensive effects, anti-remodeling effects, anti-apoptotic effects, anti-inflammatory, anti-fibrotic effects, metabolic effects, neuronal signal transmission effects and mitochondrial effects. Thus, sGC stimulators may be used to treat and/or prevent a range of diseases.

Specific diseases or disorders which may be treated and/or prevented by administering an sGC stimulator of the invention (e.g., a compound of Tables I-VI or Formula I and pharmaceutically acceptable salts thereof), include but are not limited to:

Abetalipoproteinemia, achalasia (e.g., esophageal achalasia), acute respiratory distress syndrome (ARDS), adhesive capsulitis, age-related learning and memory disturbances, age-related memory loss, alcoholism, alopecia or hair loss, altitute sickness, Alzheimer's disease (including pre-Alzheimer's disease, mild to moderate Alzheimer's disease and moderate to severe Alzheimer's disease), amyotrophic lateral sclerosis (ALS or Lou Gehrig's disease), anal fissures, aneurysm, angina (e.g., stable or unstable angina pectoris, variant angina, Prinzmetal's angina, microvascular angina), anxiety or anxiety disorders, arginosuccinic aciduria, arterial and venous thromboses, arthritis, Asperger's syndrome, asthma and asthmatic diseases, ataxia, telangliectasia, atherosclerosis (e.g., atherosclerosis associated with endothelial injury, platelet and monocyte adhesion and aggregation, smooth muscle proliferation or migration), atrophic vaginitis, attention deficit disorder (ADD) and attention deficit hyperactivity disorder (ADHD), autism and disorders in the autism spectrum, benign prostatic hyperplasia (BPH) or hypertrophy or enlargement, bipolar disorder, bladder outlet obstruction, bladder pain syndrome (BPS), blepharitis, bone and carbohydrate metabolism disturbances, bone healing (e.g. bone healing following osteoclastic bone remodeling, osteoclastic bone resorption, new bone formation), brain aneurism, brain hypoxia, cancer metastasis, cerebral amyloid angiopathy (CAA) or congophilic angiopathy, cerebral autosomal-dominant arteriopathy with subcortical infarcts and leukoencephalopathy (CADASIL or CADASIL syndrome), cerebral perfusion, cerebral small vessel disease, cerebral vasospasm, chemo-brain, childhood disintegrative disorder, chronic bronchitis, chronic fatigue, chronic traumatic encephalopathy (CTE), ciliopathies, cirrhosis (e.g., liver cirrhosis, liver cirrhosis associated with chronic liver disease, primary biliary cirrhosis), CNS-disease related sexual dysfunction, CNS-disease related sleep disturbances, cognitive defect associated with Huntington's Disease, cognitive dysfunction, cognitive impairment (e.g., vascular cognitive impairment, mild cognitive impairment, cognitive impairment associated with diabetes, cognitive impairment associated with Multiple Sclerosis, cognitive impairment associated with obstructive sleep apnea, cognitive impairment associated with schizophrenia (CIAS), cognitive impairment associated with sickle cell disease, concussion, congenital myasthenic syndrome, connective tissue disease, consequences of cerebral infarction (apoplexia cerebri), conservation of blood substituents in trauma patients, CREST syndrome, Crohn's disease, cystic fibrosis (CF), delusional disorder, dementia (e.g., vascular dementia, post-stroke dementia, Lewy body dementia, dementia with frontal lobe degeneration, dementia with frontotemporal lobar degeneration, dementia with corticobasal degeneration, Creutzfeldt-Jakob dementia, HIV-dementia, multi-infarct dementia, post-operative dementia, strategic single-infarct dementia, HIV-associated dementia (including asymptomatic neurocognitive impairment (ANI), minor neurocognitive disorder (MND), HIV-associated dementia (HAD, also called AIDS dementia complex [ADC] or HIV encephalopathy), pre-senile dementia (mild cognitive impairment, MCI), mixed dementia, Binswanger's dementia (subcortical arteriosclerotic encephalopathy), Parkinson's Dementia), demyelination, depression, depressive disorder, dermatomyositis, diabetic angiopathy, diabetic macular edema, diabetic microangiopathies, diabetic ulcers or wounds (e.g., diabetic food ulcer), diseases associated with or related to metabolic syndrome (e.g. obesity, diabetes, insulin resistance, elevated fasting glucose, elevated fasting insulin, elevated lipids), diseases involving downregulated neurotransmitters, diseases involving impaired cerebral blood flow, diseases involving impaired neurodegeneration, diseases involving impaired synaptic function, diseases involving neuroinflammation, diseases involving neurotoxicity, diseases of the organs of the male and female urogenital system (benign and malignant), disturbances of concentration in children with learning and memory problems, Down syndrome, drug addiction, drug-induced psychosis, dry eye syndrome, Duchenne muscular dystrophy, Dupuytren's contracture, dyskinesia (e.g., acute dyskinesia, chronic or tardive dyskinesia, non-motor dyskinesia, levo-dopa induced dyskinesia (LID)), dysmenhorrea (e.g., primary dysmenhorrea, secondary dysmenhorrea), dyspaneuria, dysphagia, dystonia (e.g., generalized dystonia, focal dystonia, segmental dystonia, sexual dystonia, intermediate dystonia, acute dystonic reaction, genetic or primary dystonia), edema, elecrolyte disturbances (e.g., herkalemia, hyponatremia), emphysema, endometriosis, endothelial dysfunction or injury and diseases associated with endothelial dysfunction, erectile dysfunction, esophageal achalasia, Fabry Disease, female sexual dysfunction (e.g., female sexual arousal dysfunction), fibromyalgia, fibrosis (e.g., endomyocardial fibrosis, atrial fibrosis, cardiac interstitial fibrosis, cardiac fibrosis, pulmonary fibrosis, eye fibrosis, skin fibrosis, intestinal fibrosis, renal or kidney fibrosis, interstitial renal fibrosis, pulmonary fibrosis, idiopathic pulmonary fibrosis, progressive massive fibrosis of the lungs, liver fibrosis, mediastinal fibrosis, retroperitoneal fibrosis, arthrofibrosis, bone marrow fibrosis, myelofibrosis, osteomyelofibrosis, radiation-induced fibrosis, pancreatic fibrosis), Fragile X, functional dyspepsia, gastroparesis, Gaucher Disease, general disturbances of concentration, general psychosis, glaucoma, glioblastoma, glomerulopathies (e.g., glomerulonephritis, acute glomerulonephritis, glomerulosclerosis, focal segmental glomerulosclerosis), granulomas, head injury, hearing impairment (e.g., partial hearing loss, total hearing loss, partial deafness, total deafness, noise-induced hearing loss), heart disease (e.g., left ventricular myocardial remodeling, left ventricular systolic dysfunction, ischemic cardiomyopathy, dilatated cardiomyopathy, alcoholic cardiomyopathy, storage cardiomyopathies, congenital heart deffects, decreased coronary blood flow, diastolic or systolic dysfunction, coronary insufficiency, acute coronary syndrome, coronary artery disease, arrhythmias, reduction of ventricular preload, cardiac hypertrophy, right heart hypertrophy, disturbances of atrial and ventricular rhythm and heart conduction disturbances, atrioventricular blocks of degree I-III (AVB I-III), supraventricular tachyarrhythmia, premature ventricular contraction, atrial fibrillation, atrial flutter, ventricular fibrillation, ventricular flutter, ventricular tachyarrhythmia, torsade-de-pointes tachycardia, atrial and ventricular extrasystoles, AV-junction extrasystoles, sick-sinus syndrome, AV-node reentry tachycardia, Wolff-Parkinson-White syndrome, myocardial insufficiency, chronic, acute or viral myocarditis, cardiogenic shock, cardiac remodeling), heart failure (HF; e.g.: Heart failure with preserved ejection fraction (HFPEF), Heart failure with reduced ejection fraction (HFREF), acute heart failure, chronic heart failure, acute phases of an existing chronic heart failure (worsening HF), transient heart failure, post-acute heart failure, systolic heart failure, diastolic heart failure, congestive heart failure, acute decompensated heart failure, right ventricular failure, total heart failure, high output heart failure, heart failure with valvular defects, diabetic heart failure, heart failure/cardiorenal syndrome, right heart failure), high concentration of plasminogen activator inhibitor 1 (PA-1), high levels of fibrinogen and low density DLD, histiocytosis X, Huntington's disease or chorea (HD), hyperammonemia and related, hypertension (e.g., arterial hypertension, resistant hypertension, diabetic hypertension, idiopathic hypertension, essential hypertension, secondary hypertension, gestational hypertension, portal hypertension, systemic hypertension, pre-eclampsia, increased acute and chronic coronary blood pressure), hypertonia, hypertrophic scars, hypoactive sexual arousal disorder, hypoperfusion, impotence, Inflammaroty bowel disease (e.g., Crohn's disease, Ulcerative Colitis), inflammation caused by cerebral malaria, inflammation caused by infectious disease, inflammatory response in periopration care, platelet aggregation, intellectual disability, intermittent claudication, interstitial cystitis (IC), intradialytic hypotension, ischemia (e.g., cerebral ischemia, myocardial ischemia, thromboembolic ischemia, critical limb ischemia), keloids, kidney disease (e.g., chronic kidney disease, acute and chronic renal failure, acute and chronic renal insufficiency, sequelae of renal insufficiency, renal-insufficiency related to pulmonary enema, renal-insufficiency related to HF, renal-insufficiency related to uremia or anemia, primary kidney disease, congenital kidney disease, polycystic kidney disease progression, kidney transplant rejection, immune complex-induced kidney disease, abnormally reduced creatinine and/or water excretion, abnormally increased blood concentrations of urea, nitrogen, potassium and/or creatinine, altered activity of renal enzymes (e.g. glutamyl synthetase), altered urine osmolarity or urine volume, increased microalbuminuria, macroalbuminuria, lesions of glomeruli and arterioles, tubular dilatation, hyperphosphatemia, vascular kidney disease, renal cysts, renal edema due to HF), Korsakoff psychosis, leukocyte activation, levo-dopa induced addictive behavior, lichen sclerosus, lipid related disorders (e.g., excessive adiposity, excessive subcutaneous fat, hyperlipidemias, dyslipidemia, hypercholesterolemias, decreased high-density lipoprotein cholesterol (HDL-cholesterol), moderately elevated low-density lipoprotein cholesterol (LDL-cholesterol) levels, hypertriglyceridemias, hyperglyceridemia, hypolipoproteinanemias, sitosterolemia, fatty liver disease, liver steatosis or abnormal lipid accumulation in the liver, steatosis of the heart, kidney or muscle, sitosterolemia, xanthomatosis, Tangier disease), liver diseases (e.g., vascular liver disease, hepatic stellate cell activation, hepatic fibrous collagen and total collagen accumulation, liver disease of necro-inflammatory and/or of immunological, cholestatic liver disease associated with granulomatous liver diseases, cholestatic liver disease associated with liver malignancies, cholestatic liver disease associated with intrahepatic cholestasis of pregnancy, cholestatic liver disease associated with hepatitis, cholestatic liver disease associated with sepsis, cholestatic liver disease associated with drugs or toxins, cholestatic liver disease associated with graft-versus-host disease, cholestatic liver disease associated with post-liver transplantation, cholestatic liver disease associated with choledocholithiasis, cholestatic liver disease associated with bile duct tumors, cholestatic liver disease associated with pancreatic carcinoma, cholestatic liver disease associated with Mirizzi's syndrome, cholestatic liver disease associated with AIDS, cholangiopathy, cholestatic liver disease associated with parasites, cholestatic liver disease associated with schistosomiasis, hepatitis, non-alcoholic steatohepatitis (NASH), non-alcoholic fatty liver disease (NAFLD), hepatic vaso-occlusive disease (VOD), hepatic sinusoidal obstruction syndrome (SOS), hepatic encephalopathy), localized thrombosis, lower urinary tract syndromes (LUTS), lumbar spinal canal stenosis, lupus nephritis, lupus or Systemic Lupus Erythematosus, microalbuminuria, microcirculation abnormalities, migraines, minor neurocognitive disorder (MND), morphea, moyamoya, multiple lacunar infarction, multiple organ dysfunction syndrome (MODS), multiple organ failure (MOF), multiple sclerosis (MS, including clinically isolated syndrome (CIS), relapsing-remitting MS (RRMS), primary progressive MS (PPMS), secondary progressive MS (SPMS)), multiple system atrophy (MSA), myocardial infarction or heart attack (e.g., ST-segment elevation myocardial infarction, Non-ST-segment elevation myocardial infarction, old myocardial infarction), myopic choroidal neovascularization, naevi, narcotic dependence, nephropathies (e.g., diabetic nephropathy, non-diabetic nephropathy, nephritis, nephropathy induced by toxins, contrast medium induced nephropathy, diabetic or non-diabetic nephrosclerosis, nephrotic syndrome, pyelonephritis, nephrogenic fibrosis), neurodegenerative diseases, neurogenic bladder and incontinence, neuroinflammation, neurologic disorders associated with decreased nitric oxide production, neuromuscular diseases (e.g., Duchenne muscular dystrophy (DMD), Becker muscular dystrophy (BMD), limb girdle muscular dystrophies, distal myopathies, type I and type II myotonic dystrophies, facio-scapulo-peroneal muscular dystrophy, autosomal and X-linked Emery-Dreifuss muscular dystrophy, oculopharyngeal muscular dystrophy, amyotrophic lateral sclerosis, spinal muscle atrophy (SMA)), neuromyelitis optica, neuropathies (e.g., peripheral neuropathy, autonomic neuropathy, central nervous system neuropathy, chemotherapy induced neuropathy, diabetic neuropathy, painful neuropathies, neuropathic pain, non-painful neuropathies, painful diabetic neuropathy, non-painful diabetic neuropathy, neuropathies associated to a CNS disease (e.g., Multiple sclerosis, MS), radiation-induced neuropathy), neuropathic pain associated with shingles, neuropathic pain associated with spine surgery), obsessive compulsive disorder (OCD), obstructive thromboanginitis, obstructive uropathy, oesinophilic fasciitis, osteoporosis, overactive bladder, pain (e.g., acute pain, central pain syndrome, inflammatory pain, post-operative pain, tonic pain, visceral pain, claudication pain, orphan pain indications (e.g., Acetazolamide-responsive myotonia, Autoerythrocyte sensitization syndrome, Autosomal dominant Charcot-Marie-Tooth disease type 2V, Autosomal dominant intermediate Charcot-Marie-Tooth disease with neuropathic pain, Autosomal recessive limb-girdle muscular dystrophy type 2A, Channelopathy-associated congenital insensitivity to pain, Chronic pain requiring intraspinal analgesia, Complex regional pain syndrome, Complex regional pain syndrome type 1, Complex regional pain syndrome type 2, Congenital insensitivity to pain with hyperhidrosis, Congenital insensitivity to pain with severe intellectual disability, Congenital insensitivity to pain-hypohidrosis syndrome, Diffuse palmoplantar keratoderma with painful fissures, Familial episodic pain syndrome, Familial episodic pain syndrome with predominantly lower limb involvement, Familial episodic pain syndrome with predominantly upper body involvement, Hereditary painful callosities, Hereditary sensory and autonomic neuropathy type 4, Hereditary sensory and autonomic neuropathy type 5, Hereditary sensory and autonomic neuropathy type 7, Interstitial cystitis, Painful orbital and systemic neurofibromas-marfanoid habitus syndrome, Paroxysmal extreme pain disorder, Persistent idiopathic facial pain, Qualitative or quantitative defects of calpain, Tolosa-Hunt syndrome, pancreatitis, panic disorder, Parkinson's disease, Parkinsonism Plus, Parkinson's Dysphagia, pathological eating disorders, pelvic pain, peripheral vascular disease (e.g., peripheral arterial disease, peripheral arterial occlusive disease, peripheral embolism, peripheral perfusion disturbances), peritonitis, pervasive development disorder, Peyronie's disease, Picks syndrome, polychondritis, polymyositis, post herpetic neuralgia, post-traumatic head injury, post-traumatic stress disorder (PTSD), premature ejaculation, progressive nuclear palsy, prostate hypertrophy, pulmonary disease (e.g., plexogenic pulmonary arteriopathy, bronchoconstriction or pulmonary bronchoconstriction, vascular disease of the lung, chronic obstructive pulmonary disease (COPD), pulmonary capillary hemangiomatosis, lymphangiomatosis and compressed pulmonary vessels (e.g., due to adenopathy, tumor or fibrosing mediastinitis), pulmonary vascular remodeling, pulmonary hypertonia), pulmonary hypertension (PH, e.g., pulmonary arterial hypertension (PAH), primary PH, secondary PH, sporatid PH, pre-capically PH, idiopathic PH, PH associated with left ventricular disease, PH associated with HIV, PH associated with SCD, PH associated with thromoboembolism (chronic thromboembolic PH or CTEPH), PH associated with sarcoidosis, PH associated with chronic obstructive pulmonary disease, PH associated with acute respiratory distress syndrome (ARDS), PH associated with acute lung injury, PH associated with alpha-1-antitrypsin deficiency (AATD), PH associated with pulmonary emphysema (e.g., smoking induced emphysema), PH associated with lung disease, PH associated with hypoxemia, PH associated with scleroderma, PH associated with cystic fibrosis (CF), PH associated with left ventricular dysfunction, PH associated with hypoxemia, PH (WHO groups I, II, III, IV and V), PH associated with mitral valve disease, PH associated with pericarditis, PH associated with constrictive pericarditis, PH associated with aortic stenosis, PH associated with dilated cardiomyopathy, PH associated with hyperthrophic cardiomyopathy, PH associated with restrictive cardiomyopathy, PH associated with mediastinal fibrosis, PH associated with pulmonary fibrosis, PH associated with anomalous pulmonary venous drainage, PH associated with pulmonary veno-occlusive disease, PH associated with pulmonary vasculitis, PH associated with collagen vascular disease, PH associated with congenital heart disease, PH associated with pulmonary venous hypertension, PH associated with interstitial lung disease, PH associated with sleep-disordered breathing, PH associated with chronic airflow obstruction, PH associated with obstructive sleep apnea, PH associated with central sleep apnea, PH associated with mixed sleep apnea, PH associated with alveolar hypoventilation disorders, PH associated with chronic exposure to high altitude, PH associated with neonatal lung disease, PH associated with alveolar-capillary dysplasia, PH associated with sickle cell disease, PH associated with other coagulation disorders, PH associated with chronic thromboembolism), radiculopathy, Raynaud's disease, Raynaud's syndrome (primary or secondary), refractory epilepsy, Renpennings's syndrome, reperfusion injury (e.g., ischemia-reperfusion damage, ischemia-reperfusion associated with organ transplant), restenosis (e.g., restenosis developed after thrombolysis therapies, after percutaneous transluminal angioplasties (PTAs), after transluminal coronary angioplasties (PTCAs), after heart transplant or after bypass operations), retinopathies (e.g., diabetic retinopathy, non-diabetic retinopathy, non-proliferative diabetic retinopathy, proliferative vitroretinopathy, peripheral retinal degeneration, retinal vein occlusion), Rhett's disorder, rheumatoid or rheumatic disease (e.g., arthritis, rheumatoid arthritis), sarcoidosis, sarcoids, schistosomiasis, schizoaffective disorder, schizophrenia, schizophrenia with dementia, scleroderma (e.g., localized scleroderma or circumscribed scleroderma, systemic scleroderma), sclerosis (e.g. renal sclerosis, progressive sclerosis, liver sclerosis, primary sclerosing cholanginitis, sclerosis of the gastro-intestinal tract, hippocampal sclerosis, focal sclerosis, primary lateral sclerosis, osteosclerosis, otosclerosis, atherosclerosis, tuberous sclerosis, systemic sclerosis), sepsis or septic shock or anaphylactic shock, Sickle Cell Anemia, Sickle Cell Disease, Sjogren's syndrome, sleep-wake disorders, Sneddon's syndrome, spasms (e.g., coronary spasms, vascular spasms, spasms of the peripheral arteries), spinal cord injury, spinal muscular atrophy, spinal subluxations, spinocerebellar ataxias, Steel-Richardson-Olszewski disease (progressive supranuclear palsy), stroke, subarachnoid hemorrhage, subcortical arteriosclerotic encephalopathy, syncopes, tauopathies, tension, thalamic degeneration, thromboembolic or thrombogenic disorders, transient ischemic attacks (TIAs), traumatic brain injury, tubulointerstitial diseases, ulcers, uterine fibroids, vaginal atrophy, valve deffects (e.g., mitral valve stenosis, mitral valve regurgitation, insufficiency or incompetence, aortic valve stenosis, aortic valve insufficiency, tricuspic valve insufficiency, pulmonary valve stenosis, pulmonar valve insufficiency, combined valcular deffects), vascular disease of the brain, vascular disorder resulting from cardiac and renal complications, vascular leakage or permeability, vasculitis (e.g., thrombotic vasculitis, occlusive thrombotic vasculitis, Kawasaki disease, arteritis, aortitis), vaso-occlusive crisis, venus graft failure, wet age-related macular degeneration and Williams syndrome.

In a specific embodiment of the invention, the disease is selected from sickle cell disease (SCD), focal segmental glomerulosclerosis (FSGS), heart disease, non-alcoholic steatohepatitis (NASH), non-alcoholic fatty liver disease (NAFLD), heart failure, pulmonary hypertension, liver fibrosis, and kidney fibrosis.

The term "disease", as used herein refers to any deviation from or interruption of the normal structure or function of any body part, organ, or system that is manifested by a characteristic set of symptoms and signs and whose etiology, pathology, and prognosis may be known or unknown. The term disease encompasses other related terms such as disorder and condition (or medical condition) as well as syndromes, which are defined as a combination of symptoms resulting from a single cause or so commonly occurring together as to constitute a distinct clinical picture. In some embodiments, the term disease refers to an sGC, cGMP and/or NO mediated medical or pathological disease.

"Treat", "treating" or "treatment" with regard to a disorder, disease, condition, symptom or syndrome, refers to abrogating or improving the cause and/or the effects (i.e., the symptoms, physiological, physical, psychological, emotional or any other clinical manifestations, observations or measurements, or improving pathological assessments) of the disorder, disease, condition or syndrome.

As used herein, the terms "treat", "treatment" and "treating" also refer to the delay or amelioration or prevention of the progression (i.e. the known or expected progression of the disease), severity and/or duration of the disease or delay or amelioration or prevention of the progression of one or more symptoms, clinical manifestations, observations or measurements, or preventing or slowing down the negative progression of pathological assessments (i.e. "managing" without "curing" the condition), resulting from the administration of one or more therapies.

As used herein, the terms "subject" and "patient" are used interchangeably. The terms "subject" and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In some embodiments, the subject is a non-human animal such as a farm animal (e.g., a horse, cow, pig or sheep), or a companion animal or pet (e.g., a dog, cat, mice, rats, hamsters, gerbils, guinea pig or rabbit). In some embodiments, the subject is a human.

The invention also provides a method for treating one of the above diseases in a subject, comprising administering a therapeutically effective amount of a compound of Tables I-VI or Formula I, or a pharmaceutically acceptable salt thereof, to the subject in need of the treatment. Alternatively, the invention provides the use of a compound of Tables I-VI or Formula I, or a pharmaceutically acceptable salt thereof, in the treatment of one of these diseases in a subject in need of the treatment. Also included in the invention is the use of a compound of Tables I-VI or Formula I, or a pharmaceutically acceptable salt thereof, for the manufacture of medicament for treating one of the above diseases in a subject in need of the treatment. The invention further provides a method of making or manufacturing a medicament useful for treating one of these diseases comprising using a compound of any one of Tables VI, or a pharmaceutically acceptable salt thereof.

The term "biological sample", as used herein, refers to an in vitro or ex vivo sample, and includes, without limitation, cell cultures or extracts thereof; biopsied material obtained from a mammal or extracts thereof; blood, saliva, urine, faeces, semen, tears, lymphatic fluid, ocular fluid, vitreous humor, cerebrospinal fluid (CSF), or other body fluids or extracts thereof.

In other embodiments, the invention provides a method of stimulating sGC activity in a biological sample, comprising contacting said biological sample with a compound or composition of the invention. Use of a sGC stimulator in a biological sample is useful for a variety of purposes known to one of skill in the art. Examples of such purposes include, without limitation, biological assays and biological specimen storage.

Combination Therapies

The compounds and pharmaceutical compositions described herein can be used alone or in combination therapy for the treatment of a disease mediated, regulated or influenced by sGC, cGMP and/or NO.

As used herein, the terms "in combination" (as in the sentence "in combination therapy") or "co-administration" can be used interchangeably to refer to the use of more than one therapy. The use of the terms does not restrict the order in which therapies are administered to a subject.

The compounds and pharmaceutical compositions described herein can be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent.

When used in combination therapy with other agents, a "therapeutically effective amount" of the compounds and pharmaceutical compositions described herein and of the other agent or agents will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed.

In some embodiments, co-administration or combination therapy encompasses administration of the first and second amounts of the compounds in an essentially simultaneous manner, such as in a single pharmaceutical composition, for example, capsule or tablet having a fixed ratio of first and second amounts, or in multiple, separate capsules or tablets for each. In addition, such co administration also encompasses use of each compound in a sequential manner in either order.

When co-administration involves the separate administration of a first amount of a compound of Tables I-VI or Formula I and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound of Tables I-VI or Formula I and the second therapeutic agent can be administered in any order within about 24 hours of each other, within about 16 hours of each other, within about 8 hours of each other, within about 4 hours of each other, within about 1 hour of each other or within about 30 minutes of each other.

Examples of other therapeutic agents that may be combined with a compound of Tables I-VI or Formula I, or a pharmaceutically acceptable salt thereof, either administered separately or in the same pharmaceutical composition include, but are not limited to:

(1) Endothelium-derived releasing factor (EDRF) or NO gas.

(2) NO donors including, but not limited to: a nitrosothiol, a nitrite, a sydnonimine, a NONOate, a N-nitrosamine, a N-hydroxyl nitrosamine, a nitrosimine, nitrotyrosine, a diazetine dioxide, an oxatriazole 5-imine, an oxime, a hydroxylamine, a N-hydroxyguanidine, a hydroxyurea or a furoxan. Some examples of these types of compounds include: glyceryl trinitrate (also known as GTN, nitroglycerin, nitroglycerine, and trinitrogylcerin), the nitrate ester of glycerol; sodiumnitroprusside (SNP), wherein a molecule of nitric oxide is coordinated to iron metal forming a square bipyramidal complex; 3-morpholinosydnonimine (SIN-1), a zwitterionic compound formed by combination of a morpholine and a sydnonimine; S-nitroso-N-acetylpenicillamine (SNAP), an N-acetylated amino acid derivative with a nitrosothiol functional group; diethylenetriamine/NO (DETA/NO), a compound of nitric oxide covalently linked to diethylenetriamine; an m-nitroxymethyl phenyl ester of acetyl salicylic acid. More specific examples of some of these classes of NO donors include: the classic nitrovasodilators, such as organic nitrate and nitrite esters, including nitroglycerin, amyl nitrite, isosorbide dinitrate, isosorbide 5-mononitrate, and nicorandil; isosorbide; 3-morpholinosydnonimine; linsidomine chlorohydrate ("SIN-1"); S-nitroso-N-acetylpenicillamine ("SNAP"); S-nitrosoglutathione (GSNO), sodium nitroprusside, S-nitrosoglutathione mono-ethyl-ester (GSNO-ester), 6-(2-hydroxy-1-methyl-nitrosohydrazino)-N-methyl-1-hexanamine or diethylamine NONOate.

(3) Other substances that enhance cGMP concentrations, including, but not limited toprotoporphyrin IX, arachidonic acid and phenyl hydrazine derivatives.

(4) Nitric Oxide Synthase substrates, including, but not limited to L-arginine, n-hydroxyguanidine based analogs, such as N[G]-hydroxy-L-arginine (NOHA), 1-(3,4-dimethoxy-2-chlorobenzylideneamino)-3-hydroxyguanidine, and PR5 (1-(3,4-dimethoxy-2-chlorobenzylideneamino)-3-hydroxyguanidine); L-arginine derivatives (such as homo-Arg, homo-NOHA, N-tert-butyloxy- and N-(3-methyl-2-butenyl) oxy-L-arginine, canavanine, epsilon guanidine-carpoic acid, agmatine, hydroxyl-agmatine, and L-tyrosyl-L-arginine); N-alkyl-N'-hydroxyguanidines (such as N-cyclopropyl-N'-hydroxyguanidine and N-butyl-N'-hydroxyguanidine), N-aryl-N'-hydroxyguanidines (such as N-phenyl-N'-hydroxyguanidine and its para-substituted derivatives which bear —F, —Cl, -methyl, —OH substituents, respectively); guanidine derivatives such as 3-(trifluoromethyl) propylguanidine.

(5) Compounds which enhance eNOS transcription.

(6) NO independent heme-independent sGC activators, including, but not limited to BAY 58-2667 (described in patent publication DE19943635); HMR-1766 (ataciguat, described in patent publication WO2000002851); S 3448 (2-(4-chloro-phenylsulfonylamino)-4,5-dimethoxy-N-(4-(thiomorpholine-4-sulfonyl)-phenyl)-benzamide (described in patent publications DE19830430 and WO2000002851); and HMR-1069 (from Sanofi-Aventis).

(7) Heme-dependent, NO-independent sGC stimulators including, but not limited to YC-1 (see patent publications EP667345 and DE19744026); riociguat (BAY 63-2521, Adempas®, described in DE19834044); nelociguat (BAY 60-4552, described in WO 2003095451); vericiguat (BAY 1021189, described in U.S. Pat. No. 8,420,656); BAY 41-2272 (described in DE19834047 and DE19942809); BAY 41-8543 (described in DE19834044); etriciguat (described in WO 2003086407); CFM-1571 (described in patent publication WO2000027394); A-344905, its acrylamide analogue A-350619 and the aminopyrimidine analogue A-778935;

other sGC stimulators described in one of publications US20090209556, U.S. Pat. No. 8,455,638, US20110118282 (WO2009032249), US20100292192, US20110201621, U.S. Pat. Nos. 7,947,664, 8,053,455 (WO2009094242), US20100216764, U.S. Pat. No. 8,507,512, (WO2010099054) US20110218202 (WO2010065275), US20130012511 (WO2011119518), US20130072492 (WO2011149921), US20130210798 (WO2012058132), and Tetrahedron Letters (2003), 44(48): 8661-8663; and IW1973 (praliciguat), IW1701 (olinciguat) and CY6463 (previously IW-6463).

(8) Compounds that inhibit the degradation of cGMP and/or cAMP, including, but not limited to:

PDE1 inhibitors, PDE2 inhibitors, PDE-3 inhibitors such as, for example, amrinone, milrinone, enoximone, vesnarinone, pimobendan, and olprinone, PDE4 inhibitors, such as, for example, rolumilast, PDE5 inhibitors, such as, for example, sildenafil and related agents such as avanafil, lodenafil, mirodenafil, sildenafil citrate, tadalafil, vardenafil and udenafil; alprostadil; dipyridamole and PF-00489791; PDE6 inhibitors, PDE9 inhibitors, such as, for example, PF-04447943, PDE10 inhibitors such as, for example, PF-02545920 (PF-10), and PDE11 inhibitors.

(9) Anticoagulants, including but not limited to:

coumarines (Vitamin K antagonists) such as warfarin, cenocoumarol, phenprocoumon and phenindione;

heparin and derivatives such as low molecular weight heparin, fondaparinux and idraparinux;

direct thrombin inhibitors such as argatroban, lepirudin, bivalirudin, dabigatran and ximelagatran; and tissue-plasminogen activators, used to dissolve clots and unblock arteries, such as alteplase.

(10) Antiplatelet drugs, including, but not limited to topidogrel, ticlopidine, dipyridamoleand aspirin.

(11) Supplemental oxygen therapy.

(12) Alpha-1-adrenoceptor antagonists, including, but not limited to prazosin, indoramin, urapidil, bunazosin, terazosin and doxazosin; atrial natriuretic peptide (ANP), ethanol, histamine-inducers, tetrahydrocannabinol (THC) and papaverine.

(13) Bronchodilators, including, but not limited to:

short acting $\beta_2$ agonists, such as albutamol or albuterol and terbutaline;

long acting $\beta_2$ agonists (LABAs) such as salmeterol and formoterol;

anticholinergics such as pratropium and tiotropium; and theophylline, a bronchodilator and phosphodiesterase inhibitor.

(14) Corticosteroids, including, but not limited to beclomethasone, methylprednisolone, betamethasone, prednisone, prednisolone, triamcinolone, dexamethasone, fluticasone, flunisolide, hydrocortisone, and corticosteroid analogs such as budesonide.

(15) Dietary supplements, including but not limited to omega-3 oils; folic acid, niacin, zinc, copper, Korean red ginseng root, ginkgo, pine bark, *Tribulus terrestris*, arginine, *Avena sativa*, horny goat weed, maca root, muira puama, saw palmetto, and Swedish flower pollen; vitamin C, Vitamin E, Vitamin K2; testosterone supplements, testosterone transdermal patch; zoraxel, naltrexone, bremelanotide and melanotan II.

(16) PGD2 receptor antagonists.

(17) Immunosuppressants, including, but not limited to cyclosporine, tacrolimus, rapamycin and other FK-506 type immunosuppressants, mycophenolate, mycophenolate mofetil.

(18) Non-steroidal anti-asthmatics, including, but not limited to:

β2-agonists like terbutaline, metaproterenol, fenoterol, isoetharine, albuterol, salmeterol, bitolterol and pirbuterol;

β2-agonist-corticosteroid combinations such as salmeterol-fluticasone, formoterol-budesonide, theophylline, cromolyn, cromolyn sodium, nedocromil, atropine, ipratropium, ipratropium bromide; and leukotriene biosynthesis inhibitors such as zileuton or veliflapon.

(19) Non-steroidal anti-inflammatory agents (NSAIDs), including, but not limited to:

propionic acid derivatives like alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen;

acetic acid derivatives such as indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac;

fenamic acid derivatives such as flufenamic acid, meclofenamic acid, mefenamic acid, niflumic acid and tolfenamic acid;

biphenylcarboxylic acid derivatives such as diflunisal and flufenisal;

oxicams such as isoxicam, piroxicam, sudoxicam and tenoxican;

salicylates such as acetyl salicylic acid and sulfasalazine; and pyrazolones such as apazone, bezpiperylon, feprazone, mofebutazone, oxyphenbutazone and phenylbutazone.

(20) Cyclooxygenase-2 (COX-2) inhibitors, included, but not limited to celecoxib, rofecoxib, valdecoxib, etoricoxib, parecoxib and lumiracoxib; opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine.

(21) Adrenergic neuron blockers, including, but not limited to guanethidine and guanadrel.

(22) Imidazoline I-1 receptor agonists, including, but not limited to rimenidine dihydrogen phosphate and moxonidine hydrochloride hydrate.

(23) Potassium channel activators, including, but not limited to pinacidil.

(24) Dopamine D1 agonists, including, but not limited to fenoldopam mesilate; other dopamine agonists such as ibopamine, dopexamine and docarpamine.

(25) 5-HT2 antagonists, including, but not limited to ketanserin.

(26) Vasopressin antagonists, including, but not limited to tolvaptan.

(27) Calcium channel sensitizers, including, but not limited to levosimendan or activators such as nicorandil.

(28) Adenylate cyclase activators, including, but not limited to colforsin dapropate hydrochloride.

(29) Positive inotropic agents, including, but not limited to digoxin and metildigoxin; metabolic cardiotonic agents such as ubidecarenone; brain natriuretic peptides such as nesiritide.

(30) Drugs used for the treatment of erectile dysfunction, including, but not limited to alprostadil, aviptadil, and phentolamine mesilate.

(31) Drugs used for the treatment of Alzheimer's disease and dementias, including but not limited to:

acetyl cholinesterase inhibitors such as galantamine, rivastigmine, donepezil and tacrine; and NMDA receptor antagonists such as memantine; and oxidoreductase inhibitors such as idebenone.

(32) Psychiatric medications, including, but not limited to:

ziprasidone, risperidone, olanzapine, valproate;

dopamine D4 receptor antagonists such as clozapine;

dopamine D2 receptor antagonists such as nemonapride;

mixed dopamine D1/D2 receptor antagonists such as zuclopenthixol;

GABA A receptor modulators such as carbamazepine;

sodium channel inhibitors such as lamotrigine;

monoamine oxidase inhibitors such as moclobemide and indeloxazine; and primavanserin, and perospirone.

(33) Drugs used for the treatment of movement disorders or symptoms, including, but not limited to:

catechol-O-methyl transferase inhibitors such as entacapone;

monoamine oxidase B inhibitors such as selegiline;

dopamine receptor modulators such as levodopa;

dopamine D3 receptor agonists such as pramipexole;

decarboxylase inhibitors such as carbidopa;

other dopamine receptor agonists such as pergolide, ropinirole, cabergoline; ritigonide, istradefylline, talipexole; zonisamide and safinamide; and synaptic vesicular amine transporter inhibitors such as tetrabenazine.

(34) Drugs used for the treatment of mood or affective disorders or OCD such as the following types:

tricyclic antidepressants such as amitriptyline, desipramine, imipramine, amoxapine, nortriptyline, doxepin and clomipramine;

selective serotonin reuptake inhibitors (SSRIs) such as paroxetine, fluoxetine, sertraline, trazodone and citralopram;

atypical antidepressants such as agomelatine;

selective norepinephrine reuptake inhibitors (SNRIs) such as venlafaxine, reboxetine and atomoxetine; dopaminergic antidepressants such as bupropion and amineptine.

(35) Drugs for the enhancement of synaptic plasticity, including, but not limited to:

nicotinic receptor antagonists such as mecamylamine; and mixed 5-HT, dopamine and norepinephrine receptor agonists such as lurasidone.

(36) Drugs used for the treatment of ADHD such as amphetamine; 5-HT receptor modulators such as vortioxetine and alpha-2 adrenoceptor agonists such as clonidine.

(37) Nitric oxide synthase cofactors, including, but not limited to tetrahydrobiopterin, dihydrobiopterin and sapropterin.

(38) Blood glucose lowering medications (also referred as glycemic control medications or antidiabetic medications) including, but not limited to:

biguanides such as metformin;

sulfonylureas such as glyburide, glybenclamide, glipizide, gliclazide, gliquidone, glimepiride, atorvastatin calcium combined with glimerpiride, meglinatide, tolbutamide, chlorpropamide, acetohexamide, and tolazimide;

alpha-glucosidase inhibitors such as acarbose, epalrestat, voglibose, and miglitol;

insulin secretagoges such as repaglinide, mitiglinide and nateglinide;

thiazolidinediones such as rosiglitazone, troglitazone, ciglitazone, pioglitazone, englitazone, lobeglitazone sulfate and balaglitazone;

DPP-4 inhibitors (or DPP-IV inhibitors) such as sitagliptin, vildagliptin, saxagliptin, alogliptin, linagliptin, alogliptin benzoate combined with metformin or metformin hydrochloride, anagliptin, teneligliptin, atorvastatin calcium and glimepiride, empagliflozin combined with linagliptin, gemigliptin, sitagliptin phosphate monohydrate combined with pioglitazone hydrochloride, sitagliptin combined with pioglitazone, sitagliptin combined with atorvastatin calcium, and (2S,4S)-1-[2-(1,1-dimethyl-3-oxo-3-pyrrolidin-1-yl-propylamino)acetyl]-4-fluoro-pyrrolidine-2-carbonitrile (DBPR-108);

GLP-1 receptor agonists or incretin mimetics such as exenatide, dulaglutide, liraglutide, semaglutide, lixisenatide, lixisenatide combined with insulin glargine, albiglutide and pegapamodutide (TT-401), LY3298176 (dual glucose-dependent insulinotropic polypeptide (GIP) and GLP-1 receptor agonist);

SGLT2 inhibitors (SGLT2is) such as empagliflozin, empaglifozin combined with linagliptin, empagliflozin combined with metformin, ipragliflozin, ipragliflozin L-proline, tofogliflozin, sergliflozin etabonate, remogliflozin etabonate, ertugliflozin, ertugliflozin combined with sitagliptin, ertugliflozin combined with metformin, sotagliflozin, canagliflozin, canagliflozin combined with metformin or metformin hydrochloride, dapagliflozin, dapagliflozin combined with metformin or metformin hydrochloride and luseoglifozin, dapagliflozin combined with saxagliptin;

SGLT1 inhibitors or combinations of SGLT1 and SGLT2 inhibitors such as sotagliflozin;

insulin therapy such one of the many types of insulin, like insulin glulisine, insulin degludec, insulin lispro, insulin aspart, insulin glargine, insulin detemir, insulin isophane, insulin mixtard (human insulin containing both fast-acting (soluble) and long-acting (isophane) insulin, insulin degludec combined with insulin aspart, insulin human (rDNA origin) inhalation powder, recombinant human insulin, hepatic-directed vesicle insulin, insulin tregopi (IN-105), insulin degludec combined with liraglutide, insulin peglispro (LY-2605541) and nodlin; and tolimidone (a lyn kinase activator).

(39) Blood pressure lowering medications (also known as anti-hypertensive medications), including, but not limited to:

diuretics such as thiazide diuretics, chlorothiazide, chlorthalidone, hydrochlorothiazide, bendroflumethiazide, cyclopenthiazide, methyclothiazide, polythiazide, quinethazone, xipamide, metolazone, indapamide, cicletanine, furosemide, toresamide, amiloride, spironolactone, canrenoate potassium, eplerenone, triamterene, acetazolamid and carperitide;

beta blockers such as acebutolol, atenolol, metoprolol, and nebivolol;

angiotensin-converting enzyme (ACE) inhibitors such as sulfhydryl-containing agents (for example, captopril, zofenopril), dicarboxylate-containing agents (for example, enalapril, quinapril, ramipril, perindopril, lisinopropil, and benazepril), phosphonate-containing agents (for example fosinopril), naturally occurring ACE inhibitors (for example, casokinins, lactokinins, lactotripeptides Val-Pro-Pro and Ile-Pro-Pro), alacepril, delapril, cilazapril, imidapril, temocapril, moexipril, lisinopril, combinations of lisinopril with hydrochlorothiazide, trandolapril and spirapril;

angiotensin II receptor blockers (ARBs) such as candesartan, losartan, losartan potassiur-hydrochlorothiazide, valsartan, candesartan cilexetil, eprosaran, irbesartan, telmisartan, olmesartan medoxomil (or olmesartan), azilsartan medoxomil, azilsartan, amlodipine besylate combined with irbesartan, azilsartan combined with amlodipine besilate, cilnidipine combined with valsartan, fimasartan, irbesartan combined with atorvastatin, irbesartan combined with trichlormethiazide, losartan potassium combined with hydrochlorothiazide and/or amlodipine besylate, pratosartan, atorvastatin calcium combined with losartan potassium, nifedipine and candesartan cilexetil, sacubitril combined with valsartan or LCZ-696, angiotensin AT2 antagonist and TAK-591 and olmesartan medoxomil;

endothelin Receptor antagonists (ERAs) such as atrasentan, bosentan, sitaxentan, ambrisentan, actelion-1 (macitentan), Cyclo(D-trp-D-asp-L-pro-D-val-L-leu) (BQ-123), sparsentan and tezosentan disodium;

mineralocorticoid receptor antagonists (MRAs) such as spironolactone, amiloride hydrochloride combined with spironolactone, apararenone or MT-3995, eplerenone, and finerenone (BAY-94-8862);

calcium channel blockers such as amlodipine, aranidipine, azelnidipine, barnidipine, benidipine, cilnidipine, clevidipine, diltiazem, efonidipine, felodipine, lacidipine, lercanidipine, manidipine, nicardipine, nifedipine, nilvadipine, nimodipine, nisoldipine, nitrendipine, pranidipine, isradipine, verapamil, gallopamil, diltiazem, mibefradil, bepridil, fluspirilene and fendiline;

renin inhibitors such as aliskiren;

alpha blockers such as doxazosin and prazosin;

alpha-beta blockers such as carvedilol and labetalol;

central-acting agents such as clonidine, guanfacine and methyldopa;

vasodilators such as nitroglycerine, hydralazine and minoxidil; and aldosterone antagonists such as finerenone, spironolactone and eplerenone.

(40) Anti-hyperlipidemic medications, including but not limited to:

statins such as atorvastatin fluvastatin, lovastatin, pitavastatin, pravastatin, rosuvastatin, and simvastatin;

combinations of statins with another agent such as amlodipine/atorvastatin, aspirin/pravastatin, ezetimibe/simvastatin, niacin/simvastatin, lovastatin/niacin, simvastatin/sitagliptin and atorvastatin/ezetimibe;

fibrates or fibric acid derivatives. Examples include, but are not limited to, fenofibrate, gemfibrozil, bezafibrate, ciprofibrate, clinofibrate and clofibrate;

niacin (or nicotinic acid);

bile acid sequestrants such as cholestyramine, colesevelam, colestilan and colestipol;

ezetimibe, lomitapide, phytosterols or orlistat; and

PCSK9 inhibitors such as alirocumab and evolocumab;

(41) Neprilysin inhibitors (also known as endopeptidase inhibitors or NEP inhibitors or enkephalinase inhibitors), including, but not limited to sacubitril, or the combination of sacubitril with valsartan; neprilysin inhibitors in development TD-1439 or TD-0714.

(42) Renoprotective drugs, including, but are not limited to:

Bardoxolone;

ACE inhibitors such as captopril;

ARBs such as losartan or irbesartan;

SGLT2 inhibitors such as canagliflozin,

GLP1 receptor agonists;

MRAs such as finerenone;

ERAs such as atrasentan; and apoptosis signal-regulating kinase 1 (ASK1) inhibitors such as selonsertib.

(43) Hydroxyurea (HU, hydroxycarbamide).

(44) Anti-sickling agents, including, but not limited to hydroxyurea, voxelotor or GBT-440.

(45) Anti-adhesion therapies, including, but not limited, to blocking antibodies to P-selectin, E-selectin, VLA-4, VCAM-1.

(46) Glutamine.

(47) Erythropoietin (EPO), also known as hematopoietin or hemopoietin, including all its forms such as exogenous erythropoietin, recombinant human erythropoietin (rhEPO) or other erythropoiesis-stimulating agents (ESA) two examples being epoetin alfa and epoetin beta.

(48) Antibiotics, including but not limited to:

penicilin and its derivatives, including, but not limited to penicillin, amoxicillin, ampicillin, azlocillin, cloxacillin, penicillin G, penicillin V, procaine penicillin or benzathine penicillin amongst others.

cephalosporins such as cephalexin, cefadroxil, cefaclor, cefuroxime and cefexime;

macrolides such as erythromycin, clarithromycin, azithromycin, and roxithromycin;

tetracycline and its derivatives such as demeclocycline, doxycycline, minocycline, oxytetracycline and tetracycline;

sulfonamides, including, but not limited to, mafenide, sulfacetamide, sulfadiazine, silver sulfadiazine, sulfadimethoxine, sulfamethizole, sulfamethoxazole, sulfasalazine, trimethoprim-sulfamethoxazole (Co-trimoxazole), and sulfisoxazole; and quinolones, including, but not limited to ciprofloxacin, enoxacin, gatifloxacin, gemifloxacin, levofloxacin, lomefloxacin, moxifloxacin, ofloxacin, and nalidixic acid.

(49) FXR agonists, including but not limited to obeticholic acid, cenicriviroc, emricasan, GR-MD-02, selonsertib and elafibranor.

(50) Thyroid receptor-beta agonists, including, but not limited to MGL-3196.

(51) Acetyl-CoA carboxylase inhibitors, including but not limited to GS-0976.

(52) Treatments for mitochondrial disorders including, but not limited to, vitamins and supplements, including Coenzyme Q10; B complex vitamins, especially thiamine (B1) and riboflavin (B2); Alpha lipoic acid; L-carnitine (Carnitor); Creatine; Citrulline, and L-Arginine.

(53) Treatments for epilespsy or seizures including, but not limited to, phenytoin, valproic acid, phenobarbital, lamotrigine, carbamazepine, topiramate, oxcarbazepine, zonisamide, gabapentin, levetiracetam, pregabalin, clonazepam, lacosamide, rufinamide, and vigabatrin.

Packaging and Kits

The pharmaceutical compositions (or formulations) for use may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The compounds and pharmaceutical formulations described herein may be contained in a kit. The kit may include single or multiple doses of two or more agents, each packaged or formulated individually, or single or multiple doses of two or more agents packaged or formulated in combination. Thus, one or more agents can be present in first container, and the kit can optionally include one or more agents in a second container. The container or containers are placed within a package, and the package can optionally include administration or dosage instructions. A kit can include additional components such as syringes or other means for administering the agents as well as diluents or other means for formulation. Thus, the kits can comprise: a) a pharmaceutical composition comprising a compound described herein and a pharmaceutically acceptable carrier, vehicle or diluent; and b) a container or packaging. The kits may optionally comprise instructions describing a method of using the pharmaceutical compositions in one or more of the methods described herein (e.g. preventing or treating one or more of the diseases and disorders described herein). The kit may optionally comprise a second pharmaceutical composition comprising one or more additional agents described herein for co therapy use, a pharmaceutically acceptable carrier, vehicle or diluent. The pharmaceutical composition comprising the compound described herein and the second pharmaceutical composition contained in the kit may be optionally combined in the same pharmaceutical composition.

EXAMPLES

All references provided in the Examples are herein incorporated by reference. As used herein, all abbreviations, symbols and conventions are consistent with those used in the contemporary scientific literature. See, e.g. Janet S. Dodd, ed., The ACS Style Guide: A Manual for Authors and Editors, $2^{nd}$ Ed., Washington, D.C.: American Chemical Society, 1997, herein incorporated in its entirety by reference.

Various embodiments of the invention can be described in the text below.

Definitions of the abbreviations used in the Examples section is provided in the table below.

| Abbreviation | Word or Phrase |
|---|---|
| app. | Apparent |
| Conc. | Concentration |
| DMF | N,N-dimethylformamide |
| DMSO | Dimethylsulphoxide |
| DMSO-d6 | Deuterated Dimethylsulphoxide |
| dppf | 1.1'-bis(diphenylphosphino)ferrocene |
| dba | dibenzylideneacetone |
| ES+ | Positive electron spray ionization |
| EtOAc | ethyl acetate |
| equiv. | Equivalent |
| FA | Formic Acid |
| h | hour(s) |
| HEK | Human embryonic kidney |
| HPLC | high performance liquid chromatography |
| i-PrOH | Isopropyl alcohol |
| LC-MS | Liquid Chromatography- Mass Spectrometry |
| MeOH | Methanol |
| mL | Milliliter |
| MHz | Megahertz |
| MS | Mass Spectrometry |
| NMR | Nuclear Magnetic Resonance |
| No. | Compound Number |
| Ph | Phenyl |
| ppm | parts per million |
| RP- HPLC | reversed phase high performance liquid chromatography |
| TFA | Trifluoroacetic acid |
| THF | Tetrahydrofuran |

Synthesis Section

Example 1: Synthesis of Compounds of Table I

The present invention also provides methods for synthesizing the compounds of Table I, which represent another embodiment of this invention. Compounds of this invention may be prepared according to the general and specific syntheses described herein, synthetic procedures reported in the chemical literature or methods known to a person of ordinary skill in the art. As could be appreciated by those of ordinary skill in the art, optimum reaction condition, which may be determined during the experimentation, may vary based on the reaction type and the specific reagents used in the reaction. As such, unless specifically described, reaction conditions such as pressure, temperature, relative ratio of the reagents, solvent, and reaction time may be readily selected and modified, without undue experimentation, by a person of ordinary skill in the art. Compounds and intermediates of this invention may be purified by purification methods known to a person of ordinary skill in the art. These methods include, but are not limited to, silica gel chromatography, recrystallization, reverse phase HPLC (RP-HPLC) and Supercritical Fluid Chromatography (SFC). Purification on RP-HPLC may be accomplished on a suitable reverse phase column (e.g., Waters XBridge OBD C18, 5 μm, 19×150 mm) using a suitable gradient selected from a range of 0% to 100% acetonitrile in water containing an additive such as 0.1% TFA or FA. Diastereomers may be separated by silica gel chromatography, RP-HPLC or chiral HPLC. Discrete enantiomers may be obtained from a mixture of enantiomers by resolution using a chiral HPLC. Reaction progress may be monitored by methods known to one of ordinary skill in the art such as thin layer chromatography, reverse phase HPLC, or tandem reverse phase HPLC-Mass Spectrometry (LC-MS).

Starting materials used in the syntheses described herein are available from commercial sources or may be prepared by a person of ordinary skill in the art using methods reported in the chemical literature or referenced herein.

The general methods described herein may be used to prepare compounds of Table I. The general and specific methods described herein are provided as illustrations of the enablement of the present invention. As such, they are not intended to impose any restrictions on the subject matter and the scope of the claimed compounds of this invention.

All references provided in the Examples are herein incorporated by reference. As used herein, all abbreviations, symbols and conventions are consistent with those used in the contemporary scientific literature. See, e.g. G. M. Banik, G. Baysinger, P. V. Kamat, N. J. Pienta, eds., The ACS Guide to Scholarly Communication, Washington, D.C.: American Chemical Society, 2020 (https://pub.acs.org/doi/book/10.1021/acsguide), herein incorporated in its entirety by reference.

Compounds herein disclosed can be made, for example, using the general procedure depicted below (General Procedure C) from the corresponding nitrile intermediates:

General Procedure C

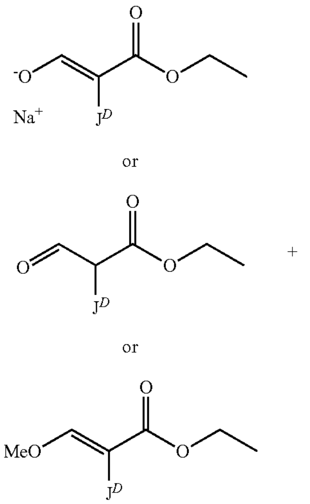

-continued

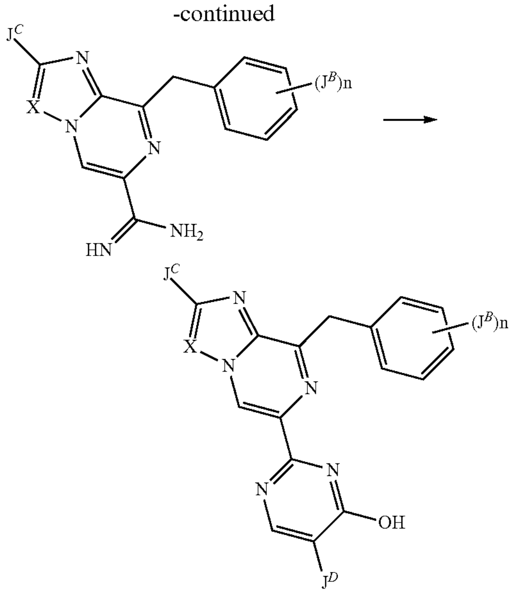

Compounds of the invention can be prepared by following similar procedures to those described herein via their corresponding nitriles. Nitriles with different patters of substitution can be prepared by following the procedures described in WO2015187470, WO2016081668, WO2017197555, WO2017200825, WO2018/045276A1 and WO2019/126354A1.

The following nitrile intermediates were prepared according to literature procedures described in WO2018/045276A1 and WO2019/126354A1. The reaction conditions (such as reagents ratio, temperature and reaction time) and purification methods were modified as needed.

8-Benzylimidazo[1,2-a]pyrazine-6-carbonitrile;

8-(3-Fluorobenzyl)imidazo[1,2-a]pyrazine-6-carbonitrile;

8-(2-Fluorobenzyl)imidazo[1,2-a]pyrazine-6-carbonitrile;

8-(2,3-Difluorobenzyl)imidazo[1,2-a]pyrazine-6-carbonitrile;

8-(2,5-Difluorobenzyl)imidazo[1,2-a]pyrazine-6-carbonitrile;

8-(3-Fluoro-4-methylbenzyl)imidazo[1,2-a]pyrazine-6-carbonitrile;

8-(3,5-Difluorobenzyl)imidazo[1,2-a]pyrazine-6-carbonitrile;

8-(3,5-Difluoro-4-methylbenzyl)imidazo[1,2-a]pyrazine-6-carbonitrile;

8-(2,5-Difluoro-4-methylbenzyl)imidazo[1,2-a]pyrazine-6-carbonitrile;

8-(2,5-Difluorobenzyl)-[1,2,4]triazolo[1,5-a]pyrazine-6-carbonitrile;

8-(3-Fluorobenzyl)-[1,2,4]triazolo[1,5-a]pyrazine-6-carbonitrile;

8-(3,5-Difluorobenzyl)-[1,2,4]triazolo[1,5-a]pyrazine-6-carbonitrile;

8-(2,3-Difluorobenzyl)-[1,2,4]triazolo[1,5-a]pyrazine-6-carbonitrile;

8-(2,5-Difluoro-4-methylbenzyl)-[1,2,4]triazolo[1,5-a]pyrazine-6-carbonitrile.

General Procedure a, Exemplified as Applied to the Synthesis Compound I-1

The title compound was synthesized in 2 steps:

Step 1: Synthesis of 8-(3-fluorobenzyl)imidazo[1,2-a]pyrazine-6-carboximidamide

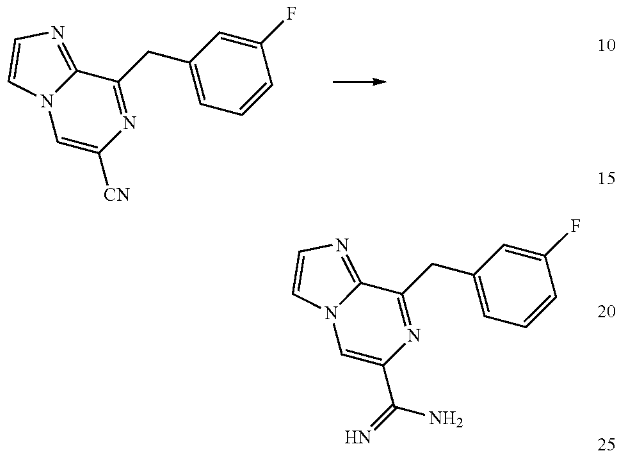

To a solution of 8-(3-fluorobenzyl)imidazo[1,2-a]pyrazine-6-carbonitrile (220 mg, 0.87 mmol, 1.0 equiv.) in methanol (5.0 mL) was added a solution of 0.50 N sodium methanolate in methanol (0.17 mL, 0.087 mmol, 0.10 equiv.) (note: stoichiometric or excess amount of sodium methanolate could also be used). After 6 h of stirring at ambient temperature, ammonium chloride (280 mg, 5.2 mmol, 6.0 equiv.) was added and the reaction was allowed to stir for 16 h. The reaction mixture was concentrated in vacuo, diluted with half-saturated $NaHCO_3$ solution (20 mL) and extracted with 2×20 mL of $CH_2Cl_2$/iPrOH (5:1). The combined organic phases were dried over sodium sulfate, filtered, and concentrated to afford the crude product carboximidamide as a tan foam solid. It was used in the next step without further purification.

LC/MS $ES^+$ m/z=270.2 $[M+H]^+$.

Step 2: Synthesis of 5-fluoro-2-(8-(3-fluorobenzyl)imidazo[1,2-a]pyrazin-6-yl)pyrimidin-4-ol

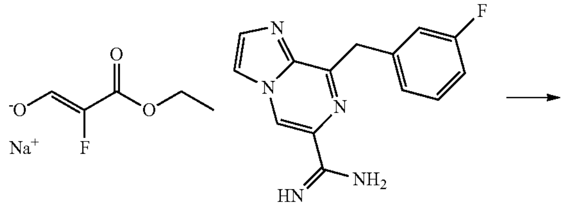

-continued

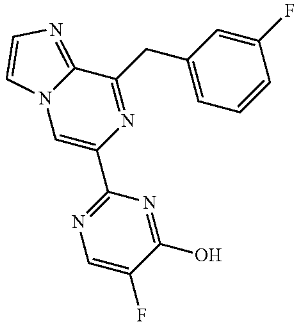

Compound I-1

To a suspension of 8-(3-fluorobenzyl)imidazo[1,2-a]pyrazine-6-carboximidamide (210 mg, 0.79 mmol, 1.0 equiv.) in ethanol (7.0 mL) was added sodium (Z)-3-ethoxy-2-fluoro-3-oxoprop-1-en-1-olate (490 mg, 3.1 mmol, 4.0 equiv.). The reaction was heated in a sealed vial at 90° C. for 2.5 h. After cooling to ambient temperature, 1.0 N aqueous HCl solution (3.1 mL, 3.1 mmol, 4.0 equiv.) was added. The resultant mixture was concentrated in vacuo, diluted with water (50 mL), adjusted to pH 6 with saturated $NaHCO_3$ solution, and extracted with 2×50 mL of $CH_2Cl_2$/iPrOH (5:1). The combined organic phases were dried over sodium sulfate, filtered, and concentrated. The crude material was purified via silica gel chromatography (0-15% acetonitrile/methanol (7:1) in $CH_2Cl_2$) to deliver the title compound (180 mg, 64% yield over 2 steps) as a light tan solid. $^1H$ NMR (500 MHz, DMSO-$d_6$) δ (ppm) 13.1-12.5 (pair of s, 1H, tautomers), 9.46 (s, 1H), 8.30 (s, 1H), 8.26-8.00 (pair of s, 1H, tautomers), 7.90 (s, 1H), 7.50 (m, 1H), 7.41 (m, 1H), 7.32 (m, 1H), 7.02 (app. t, 1H), 4.53 (s, 2H).

Compound I-2

Compound I-2

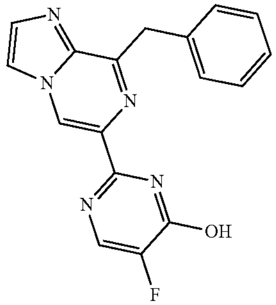

2-(8-Benzylimidazo[1,2-a]pyrazin-6-yl)-5-fluoropyrimidin-4-ol (Compound 2) was synthesized according to General Procedure A as a white solid (25 mg, 14% overall yield). The reaction conditions (such as reagents ratio, temperature and reaction time) and purification methods were modified as needed. $^1H$ NMR (500 MHz, methanol-$d_4$) δ (ppm) 9.30 (s, 1H), 8.09 (s, 1H), 7.99 (d, 1H), 7.80 (s, 1H), 7.40 (d, 2H), 7.17 (t, 2H), 7.07-7.11 (m, 1H), 4.52 (s, 2H).

Compound I-4

-continued

Compound I-4

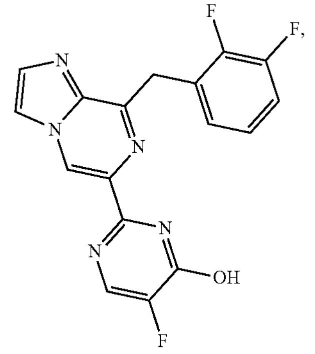

2-(8-(2,3-Difluorobenzyl)imidazo[1,2-a]pyrazin-6-yl)-5-fluoropyrimidin-4-ol (Compound 4) was synthesized according to General Procedure A as a light tan solid (150 mg, 67% overall yield). The reaction conditions (such as reagents ratio, temperature and reaction time) and purification methods were modified as needed. $^1$H NMR (500 MHz, acetone-$d_6$) δ (ppm) 10.6 (s, 1H), 9.34 (s, 1H), 8.16 (s, 1H), 7.92 (s, 1H), 7.78 (s, 1H), 7.20 (t, 1H), 7.09 (q, 1H), 7.00 (q, 1H), 4.60 (s, 2H).

Compound I-6

Compound I-6

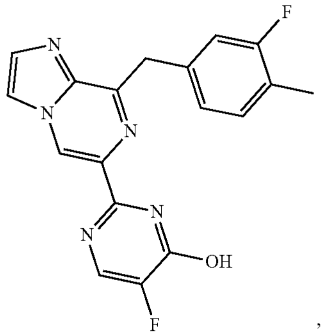

,

5-Fluoro-2-(8-(3-fluoro-4-methylbenzyl)imidazo[1,2-a]pyrazin-6-yl)pyrimidin-4-ol (Compound I-6) was synthesized according to General Procedure A as a pale yellow solid (200 mg, 54% overall yield). The reaction conditions (such as reagents ratio, temperature and reaction time) and purification methods were modified as needed. $^1$H NMR (500 MHz, DMSO-$d_6$) δ (ppm) 12.9 (br. s, 1H), 9.44 (s, 1H), 8.29 (s, 1H), 8.16 (br. s, 1H), 7.89 (s, 1H), 7.39 (d, 1H), 7.27 (d, 1H), 7.17 (t, 1H), 4.48 (s, 2H), 2.14 (s, 3H).

Compound I-7

-continued

Compound I-7

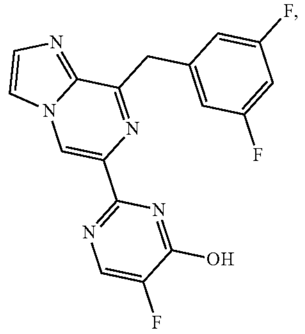

2-(8-(3,5-Difluorobenzyl)imidazo[1,2-a]pyrazin-6-yl)-5-fluoropyrimidin-4-ol (Compound I-7) was synthesized according to General Procedure A as a yellow solid (190 mg, 57% overall yield). The reaction conditions (such as reagents ratio, temperature and reaction time) and purification methods were modified as needed. $^1$H NMR (500 MHz, DMSO-$d_6$) δ (ppm) 13.0 (br. s, 1H), 9.47 (s, 1H), 8.31 (s, 1H), 8.22 (br. s, 1H), 7.91 (s, 1H), 7.36 (br. s, 2H), 7.07 (t, 1H), 4.53 (s, 2H).

Compound I-3

Compound I-3

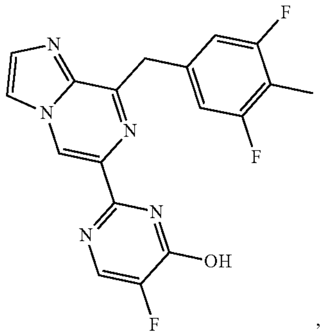

,

5-Fluoro-2-(8-(3,5-difluoro-4-methylbenzyl)imidazo[1,2-a]pyrazin-6-yl)pyrimidin-4-ol (Compound 3) was synthesized according to General Procedure A as a white solid (67 mg, 34% overall yield). The reaction conditions (such as reagents ratio, temperature and reaction time) and purification methods were modified as needed. $^1$H NMR (500 MHz, chloroform-d) δ (ppm) 11.1 (br. s, 1H), 9.14 (s, 1H), 8.00-7.91 (m, 2H), 7.87 (s, 1H), 7.00 (d, 2H), 4.56 (s, 2H), 2.14 (s, 3H).

Compound I-14

The title compound was synthesized in 2 steps:

Step 1: Synthesis of 8-(2,5-difluoro-4-methylbenzyl)imidazo[1,2-a]pyrazine-6-carboximidamide

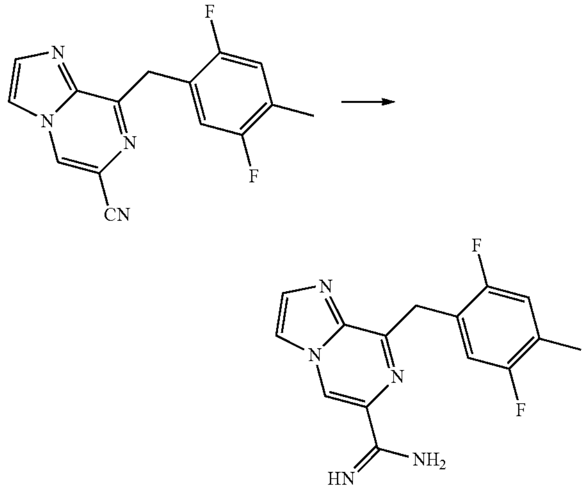

To a suspension of 8-(2,5-difluoro-4-methylbenzyl)imidazo[1,2-a]pyrazine-6-carbonitrile (2.5 g, 8.9 mmol, 1.0 equiv.) in methanol (44 mL) was added a solution of 0.50 N sodium methanolate in methanol (18 mL, 8.9 mmol, 1.0 equiv.). After 4 h of stirring at ambient temperature, an additional portion of 0.50 N sodium methanolate in methanol (5.3 mL, 2.7 mmol, 0.3 equiv.) was added and stirring was continued for another 2 h. Ammonium chloride (470 mg, 8.9 mmol, 1.0 equiv.) was then added. After 16 h, the reaction mixture was concentrated in vacuo, suspended in aqueous saturated $NaHCO_3$ solution, and stirred for 20 min. The solid was collected by filtration and washed with 3 volumes of water and 2 volumes of ether. The crude product was re-suspended in 100 mL of acetonitrile with heating, diluted with ether, and filtered. The filter cake was washed with 3 volumes of ether and dried to afford a tan solid (2.2 g, 83% yield). It was used in the next step without further purification. LC/MS $ES^+$ m/z=302.1 $[M+H]^+$.

Step 2: Synthesis of 5-fluoro-2-(8-(2,5-difluoro-4-methylbenzyl)imidazo[1,2-a]pyrazin-6-yl)pyrimidin-4-ol

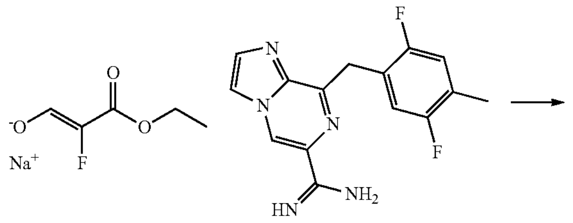

-continued

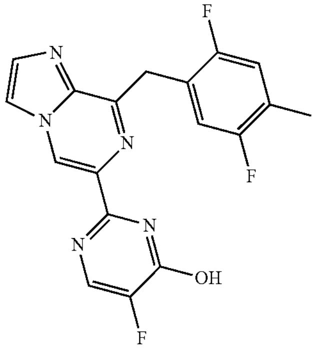

Compound I-14

To 8-(2,5-difluoro-4-methylbenzyl)imidazo[1,2-a]pyrazine-6-carboximidamide (1.9 g, 6.2 mmol, 1.0 equiv.) in ethanol (31 mL) was added sodium (Z)-3-ethoxy-2-fluoro-3-oxoprop-1-en-1-olate (2.9 g, 19 mmol, 3.0 equiv.). The solution was heated in a sealed vessel at 90° C. for 18 h. After cooling to ambient temperature, 2.5 N ethanolic HCl solution (7.4 mL, 19 mmol, 3.0 equiv.) was added. The resultant mixture was concentrated in vacuo, suspended in acetonitrile (100 mL) with heating. After slight cooling, ether (100 mL) was added and the mixture was stirred for 10 min. The solid was collected by filtration and washed with 3 volumes of ether. The resultant solid was re-suspended in water, stirred for 1 h and filtered. The crude material was purified via preparative reverse phase HPLC (10-70% acetonitrile/water with 0.1% trifluoroacetic acid as additive). Impure fractions were repurified via preparative reverse phase HPLC (10-50% acetonitrile/water with 0.1% trifluoroacetic acid as additive) to deliver the title compound (840 mg, 37% yield) as an off-white solid. $^1H$ NMR (500 MHz, methanol-$d_4$) δ (ppm) 9.43 (s, 1H), 8.21 (s, 1H), 8.08 (br. s, 1H), 7.89 (s, 1H), 7.09 (m, 1H), 7.00 (m, 1H), 4.63 (s, 2H), 2.23 (s, 3H).

Na+ salt of Compound 14

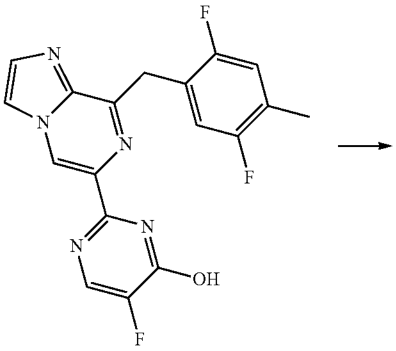

-continued

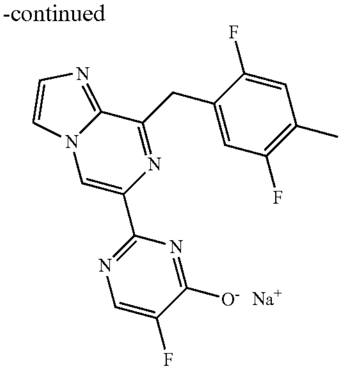

Compound I-1-14-Na+

To an off-white suspension of 5-fluoro-2-(8-(2,5-difluoro-4-methylbenzyl)imidazo[1,2-a]pyrazin-6-yl)pyrimidin-4-ol (Compound I-14, 10 g, 27 mmol) in 450 mL of anhydrous MeOH under a nitrogen atmosphere was added a solution of 0.50 N sodium methanolate in methanol (54 mL, 27 mmol). After brief sonication, the resultant light yellow solution was stirred at ambient temperature for 15 min and concentrated to dryness in vacuo. The solid was re-suspended in 250 mL of ether with the aid of sonication and concentrated (two times). The resultant solid was re-suspended in 650 mL of ether and stirred at ambient temperature for 3 h. The solid was collected by vacuum filtration and washed with ether (3×100 mL). After drying overnight on the filter, the product salt was dried in a vacuum oven at 45° C. for 4 days to afford sodium 5-fluoro-2-(8-(2,5-difluoro-4-methylbenzyl)imidazo[1,2-a]pyrazin-6-yl)pyrimidin-4-olate (11 g, 99% yield) as a white solid. $^1$H NMR (500 MHz, $D_2O$) □ (ppm) 8.92 (s, 1H), 7.99 (d, 1H), 7.97 (d, 1H), 7.70 (d, 1H), 6.98 (dd, 1H), 6.86 (dd, 1H), 4.48 (s, 2H), 2.14 (s, 3H).

Compound I-11

Compound I-11

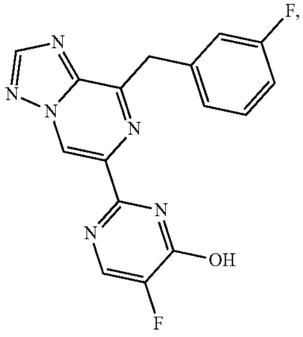

5-Fluoro-2-(8-(3-fluorobenzyl)-[1,2,4]triazolo[1,5-a]pyrazin-6-yl)pyrimidin-4-ol (Compound I-11) was synthesized according to General Procedure A as a yellow-gold solid (61 mg, 23% overall yield). The reaction conditions (such as reagents ratio, temperature and reaction time) and purification methods were modified as needed. $^1$H NMR (500 MHz, DMSO-$d_6$) δ (ppm) 13.3 (br. s, 1H), 9.60 (s, 1H), 8.86 (s, 1H), 8.24-8.27 (m, 1H), 7.32-7.47 (m, 3H), 7.03-7.06 (m, 1H), 4.59 (s, 2H).

Compound I-13

-continued

Compound I-13

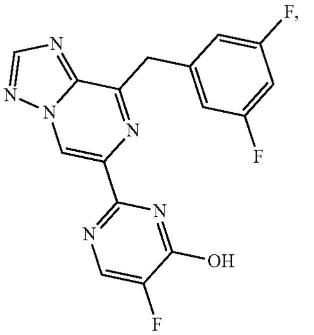

2-(8-(3,5-Difluorobenzyl)-[1,2,4]triazolo[1,5-a]pyrazin-6-yl)-5-fluoropyrimidin-4-ol (Compound I-13) was synthesized according to General Procedure A as a brown solid (57 mg, 17% overall yield). The reaction conditions (such as reagents ratio, temperature and reaction time) and purification methods were modified as needed. $^1$H NMR (500 MHz, DMSO-$d_6$) δ (ppm) 13.2 (br. s, 1H), 9.61 (s, 1H), 8.87 (s, 1H), 8.25 (s, 1H), 7.33 (d, 2H), 7.10 (t, 1H), 4.60 (s, 2H).

Compound I-10

Compound I-10

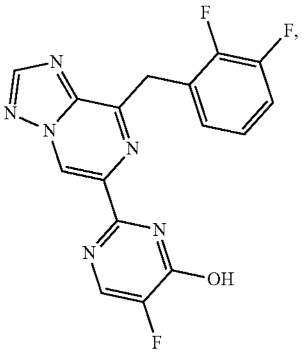

2-(8-(2,3-Difluorobenzyl)-[1,2,4]triazolo[1,5-a]pyrazin-6-yl)-5-fluoropyrimidin-4-ol (Compound I-10) was synthesized according to General Procedure A as a pale-yellow solid (85 mg, 16% overall yield). The reaction conditions (such as reagents ratio, temperature and reaction time) and purification methods were modified as needed. $^1$H NMR (500 MHz, DMSO-$d_6$) δ (ppm) 13.0 (br. s, 1H), 9.62 (s, 1H), 8.85 (s, 1H), 8.23 (s, 1H), 7.29-7.37 (m, 2H), 7.09-7.16 (m, 1H), 4.68 (s, 2H).

Compound I-12

-continued

Compound I-12

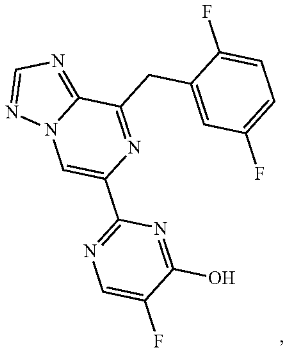

, 2-(8-(2,5-Difluorobenzyl)-[1,2,4]triazolo[1,5-a]pyrazin-6-yl)-5-fluoropyrimidin-4-ol (Compound I-12) was synthesized according to General Procedure A as an off-white solid (75 mg, 57% yield). The reaction conditions (such as reagents ratio, temperature and reaction time) and purification methods were modified as needed. $^{1}$H NMR (500 MHz, methanol-$d_4$) δ (ppm) 9.67 (s, 1H), 8.69 (s, 1H), 8.12 (d, 1H), 7.25 (m, 1H), 7.13 (m, 1H), 7.02 (m, 1H), 4.73 (s, 2H).

Compound I-19

Compound I-19

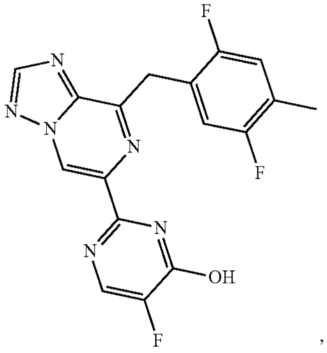

,

5-Fluoro-2-(8-(2,5-difluoro-4-methylbenzyl)-[1,2,4]triazolo[1,5-a]pyrazin-6-yl)pyrimidin-4-ol (Compound I-19) was synthesized according to General Procedure A as a tan solid (140 mg, 66% overall yield). The reaction conditions (such as reagents ratio, temperature and reaction time) and purification methods were modified as needed. $^{1}$H NMR (500 MHz, DMSO-$d_6$) δ (ppm) 13.1 (br. s, 1H), 9.61 (s, 1H), 8.83 (s, 1H), 8.26 (br. s, 1H), 7.35 (br. s, 1H), 7.17 (m, 1H), 4.57 (s, 2H), 2.18 (s, 3H).

General Procedure B, Exemplified as Applied to the Synthesis of Compound I-16

The title compound was synthesized in 2 steps:

Step 1: Synthesis of 8-(2,5-difluorobenzyl)imidazo[1,2-a]pyrazine-6-carboximidamide

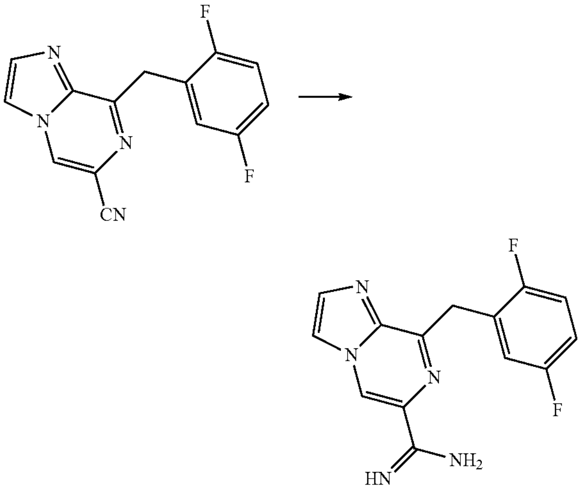

To a suspension of 8-(2,5-difluorobenzyl)imidazo[1,2-a]pyrazine-6-carbonitrile (490 mg, 1.8 mmol, 1.0 equiv.) in methanol (5.0 mL) was added a solution of 0.50 N sodium methanolate in methanol (3.6 mL, 1.8 mmol, 1.0 equiv.) (note: catalytic or excess amount of sodium methanolate could also be used). After 3 h 45 min of stirring at ambient temperature, ammonium chloride (970 mg, 18 mmol, 10 equiv.) was added and the reaction was stirred for 20 h. The resultant mixture was concentrated in vacuo to a volume of about 2 mL and diluted with EtOAc (20 mL) and 10% aqueous $NaHCO_3$ solution (10 mL). After stirring for 15 min, the product was collected by filtration, washed with water (10 mL) and dried in vacuo to afford the title compound (420 mg, 80% yield) as an off-white solid. LC/MS $ES^{+}$ m/z=287.9 $[M+H]^{+}$.

Step 2: Synthesis of 5-chloro-2-(8-(2,5-difluorobenzyl)imidazo[1,2-a]pyrazin-6-yl)pyrimidin-4-ol

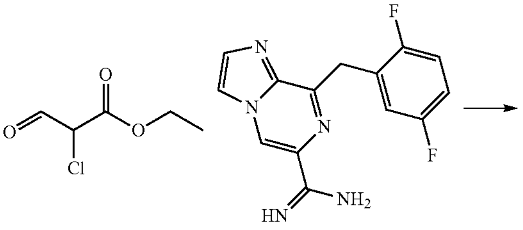

-continued

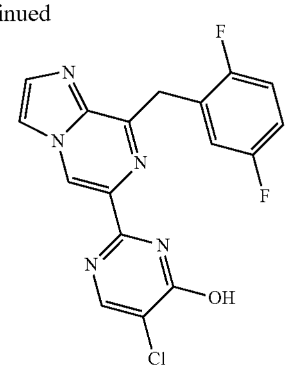

Compound I-16

To a suspension of 8-(2,5-difluorobenzyl)imidazo[1,2-a]pyrazine-6-carboximidamide (100 mg, 0.35 mmol) and ethyl 2-chloro-3-oxopropanoate (110 mg, 0.70 mmol) in methanol (1.7 mL) was added a solution of 0.50 N sodium methanolate in methanol (1.4 mL, 0.70 mmol). The reaction was heated in a sealed vial at 65° C. for 2.5 h. After cooling to ambient temperature, the resultant mixture was concentrated in vacuo, diluted with water (10 mL), adjusted to pH 3 with 6.0 N aqueous HCl solution, and extracted with 2×15 mL of $CH_2Cl_2$/iPrOH (8:1). The combined organic phases were dried over sodium sulfate, filtered, and concentrated. The crude material was purified via silica gel chromatography (0-20% acetonitrile/methanol (7:1) in $CH_2Cl_2$) and repurified via silica gel chromatography (20-100% EtOAc/$CH_2Cl_2$) to deliver the title compound (37 mg, 28% yield) as an off-white solid.

$^1$H NMR (500 MHz, DMSO-$d_6$) δ (ppm) 12.6 (br. s, 1H), 9.54 (s, 1H), 8.36 (br. s, 1H), 8.32 (s, 1H), 7.89 (s, 1H), 7.45 (br. s, 1H), 7.25 (m, 1H), 7.12 (m, 1H), 4.58 (s, 2H).

Compound I-17

Compound I-17

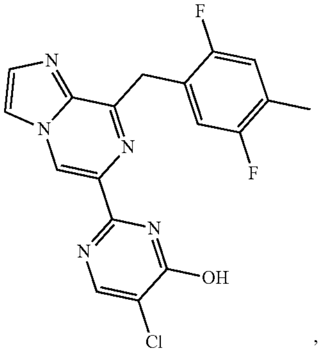

,

5-Chloro-2-(8-(2,5-difluoro-4-methylbenzyl)imidazo[1,2-a]pyrazin-6-yl)pyrimidin-4-ol (Compound I-17) was synthesized according to General Procedure B as a tan solid (5.2 mg, 2.2% overall yield). The reaction conditions (such as reagents ratio, temperature and reaction time) and purification methods were modified as needed. $^1$H NMR (500 MHz, DMSO-$d_6$) δ (ppm) 9.47 (s, 1H), 8.45 (s, 1H), 8.22 (d, 1H), 7.94 (s, 1H), 7.23 (dd, 1H), 7.16 (dd, 1H), 6.72 (d, 1H), 4.56 (s, 2H), 2.17 (br s, 3H). LC/MS ES$^+$ m/z=388.0 [M+H]$^+$.

Compound I-15

The title compound was synthesized in 2 steps:

Step 1: Synthesis of 8-(2,5-difluoro-4-methylbenzyl)imidazo[1,2-a]pyrazine-6-carboximidamide

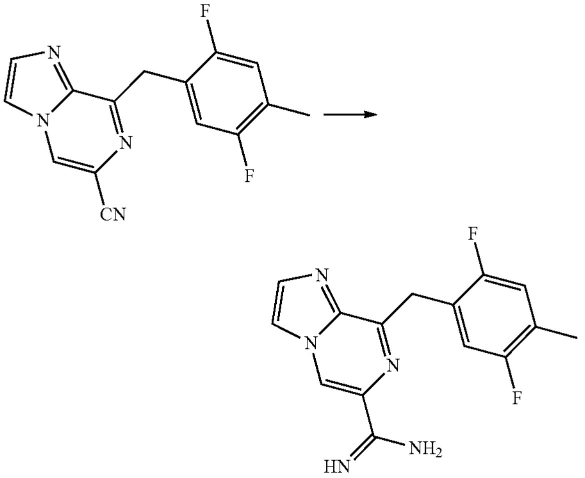

8-(2,5-Difluoro-4-methylbenzyl)imidazo[1,2-a]pyrazine-6-carboximidamide was synthesized according to Step 1 of General Procedure A or B as a tan solid (840 mg, 76% yield). The reaction conditions (such as reagents ratio, temperature and reaction time) and purification methods were modified as needed. LC/MS ES$^+$ m/z=302.0 [M+H]$^+$.

Step 2: Synthesis of 2-(8-(2,5-difluoro-4-methylbenzyl)imidazo[1,2-a]pyrazin-6-yl)pyrimidin-4-ol

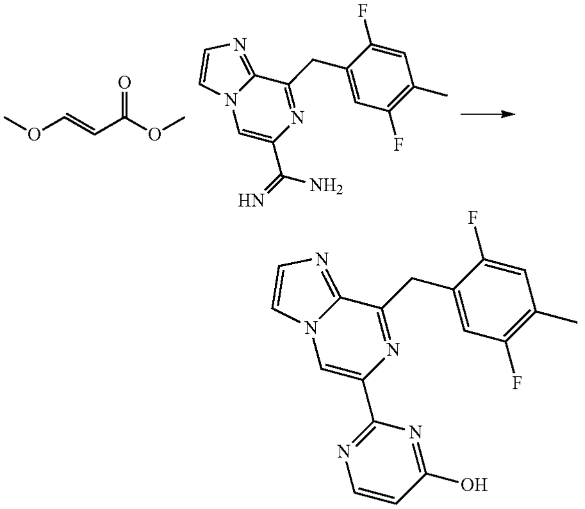

Compound I-15

To a suspension of 8-(2,5-difluoro-4-methylbenzyl)imidazo[1,2-a]pyrazine-6-carboximidamide (360 mg, 1.2 mmol) and methyl 3-methoxyacrylate (0.39 mL, 3.6 mmol) in ethanol (6.0 mL) was added Hunig's base (0.63 mL, 3.6 mmol). The reaction was heated in a sealed vial at 90° C. for 3 h. After cooling to ambient temperature, the resultant mixture treated with 2.5 N ethanolic HCl solution (1.4 mL, 3.6 mmol) and concentrated to dryness. The crude material was purified via silica gel chromatography (0-20% acetonitrile/methanol (7:1) in $CH_2Cl_2$) and repurified via silica gel chromatography (0-15% $MeOH/CH_2Cl_2$) to deliver the title compound (120 mg, 28% yield) as a tan solid. $^1H$ NMR (500 MHz, DMSO-$d_6$) δ (ppm) 11.9 (br. s, 1H), 9.52 (s, 1H), 8.31 (s, 1H), 8.07 (br. d, 1H), 7.89 (s, 1H), 7.37 (dd, 1H), 7.16 (dd, 1H), 6.38 (br. d, 1H), 4.54 (s, 2H), 2.18 (s, 3H).

Compound I-8

The title compound was synthesized in 2 steps:

Step 1: Synthesis of 8-(2-fluorobenzyl)imidazo[1,2-a]pyrazine-6-carboximidamide

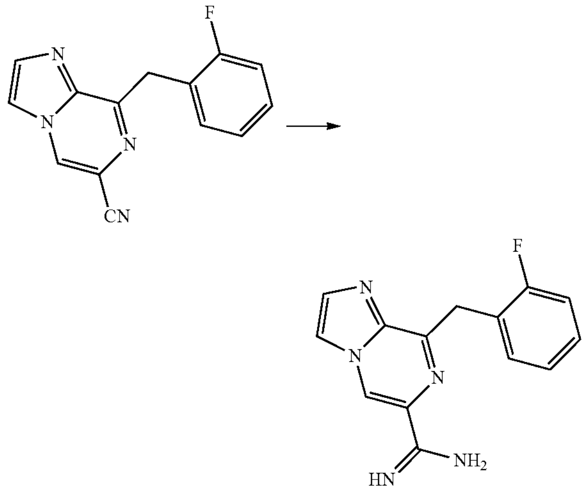

8-(2-Fluorobenzyl)imidazo[1,2-a]pyrazine-6-carboximidamide was synthesized according to Step 1 of General Procedure A or B as a cream-colored solid (5.1 g, 91% yield). The reaction conditions (such as reagents ratio, temperature and reaction time) and purification methods were modified as needed. LC/MS $ES^+$ m/z=270.2 $[M+H]^+$.

Step 2: Synthesis of 2-(8-(2-fluorobenzyl)imidazo[1,2-a]pyrazin-6-yl)-5-methylpyrimidin-4-ol

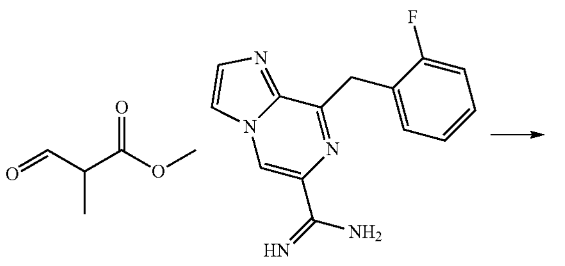

-continued

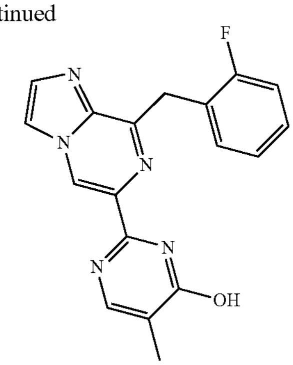

Compound I-8

To a solution of 8-(2-fluorobenzyl)imidazo[1,2-a]pyrazine-6-carboximidamide (400 mg, 1.5 mmol) and ethyl 2-methyl-3-oxopropanoate (230 mg, 1.8 mmol) in t-BuOH (9.9 mL) was added potassium hydrogencarbonate (220 mg, 2.2 mmol). The reaction was heated to reflux for 2 h. After cooling to ambient temperature, water was added and the product was collected by filtration and dried to deliver the title compound as a cream-colored solid (410 mg, 82% yield). $^1H$ NMR (500 MHz, DMSO-$d_6$) δ (ppm) 11.6 (br. s, 1H), 9.48 (s, 1H), 8.30 (s, 1H), 7.94 (br s, 1H), 7.88 (s, 1H), 7.48 (app. t, 1H), 7.29 (m, 1H), 7.19 (m, 1H), 7.11 (app. t, 1H), 4.60 (s, 2H), 1.98 (s, 3H).

Compound I-9

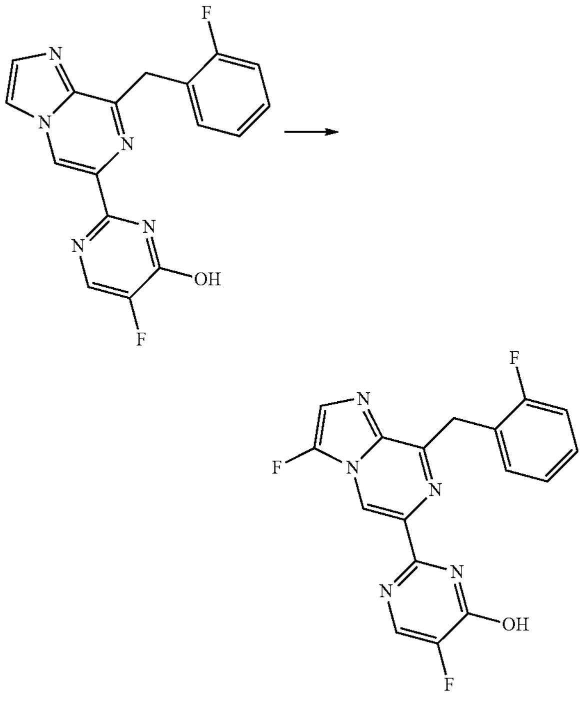

Compound I-9

5-Fluoro-2-(8-(2-fluorobenzyl)imidazo[1,2-a]pyrazin-6-yl)pyrimidin-4-ol (230 mg, 0.67 mmol) in 9.0 mL of acetonitrile-THF (2:1) was treated with sodium hydrogen carbonate (84 mg, 1.0 mmol) and Selectfluor™ (350 mg, 1.0 mmol) and heated at 50° C. Over the course of the experiment, additional portions of sodium hydrogen carbonate (42+28 mg) and Selectfluor™ (180+120 mg) were added. After a total of 49 h, the reaction was cooled to ambient temperature and 20 mL of water was added. The resultant mixture was acidified to pH 3 with 1.0 N aqueous HCl solution and extracted with 2×25 mL of EtOAc. The combined organic phases were dried over sodium sulfate, filtered, and concentrated. The crude material was purified via silica gel chromatography (0-20% acetonitrile/methanol (7:1) in $CH_2Cl_2$) and repurified via preparative reverse phase HPLC (15-65% acetonitrile/water with 0.1% formic acid as additive) to deliver the title compound (23 mg, 9.7% yield) as a tan solid. $^1$H NMR (500 MHz, DMSO-$d_6$) δ (ppm) 12.6 (br. s, 1H), 8.98 (s, 1H), 8.19 (br. s, 1H), 7.74 (d, 1H), 7.48 (app. t, 1H), 7.28 (m, 1H), 7.19 (m, 1H), 7.10 (app. t, 1H), 4.56 (s, 2H).

Compound I-5

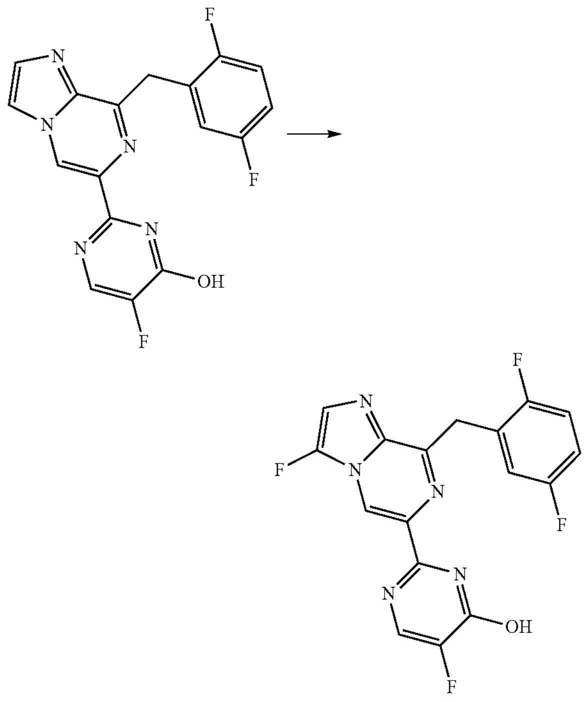

Compound I-5

5-Fluoro-2-(8-(2,5-difluorobenzyl)imidazo[1,2-a]pyrazin-6-yl)pyrimidin-4-ol (200 mg, 0.56 mmol) in 10 mL of acetonitrile-THF (1:1) was treated with sodium hydrogen carbonate (94 mg, 1.1 mmol) and Selectfluor™ (400 mg, 1.1 mmol) and heated at 50° C. Over the course of the experiment, additional portions of sodium hydrogen carbonate (3×47 mg) and Selectfluor™ (3×200 mg) were added. After a total of 74 h, the reaction was cooled to ambient temperature and 40 mL of water was added. The resultant mixture was acidified to pH 3 with 1.0 N aqueous HCl solution and extracted with 2×40 mL of $CH_2Cl_2$/iPrOH (6:1). The combined organic phases were dried over sodium sulfate, filtered, and concentrated. The crude material was purified by silica gel chromatography (0-20% acetonitrile/methanol (7:1) in $CH_2Cl_2$), preparative reverse phase HPLC (10-70% acetonitrile/water with 0.1% TFA as additive) and a final column chromatography (20-100% EtOAc/hexanes) to deliver the title compound (24 mg, 11% yield) as a white solid. $^1$H NMR (500 MHz, DMSO-$d_6$) δ (ppm) 12.8 (br. s, 1H), 8.99 (s, 1H), 8.20 (br. s, 1H), 7.75 (d, 1H), 7.42 (m, 1H), 7.25 (m, 1H), 7.13 (m, 1H), 4.54 (s, 2H).

Compound I-18

The title compound was synthesized in 5 steps:

Step 1: Synthesis of 6,8-dibromo-3-fluoroimidazo[1,2-a]pyrazine

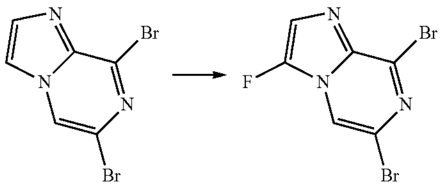 [SMILES: Brc1cn2ccnc2c(Br)n1 ; Fc1cnc2c(Br)nc(Br)cn12]

6,8-Dibromoimidazo[1,2-a]pyrazine (2.4 g, 8.7 mmol) in 40 mL of acetonitrile was treated with Selectfluor™ (4.6 g, 13 mmol) and heated at 50° C. After a 22 h, the reaction was cooled to ambient temperature, poured into 150 mL of half-saturated $NaHCO_3$ solution and extracted with 2×EtOAc (400 mL total). The combined organic phases were dried over sodium sulfate, filtered, and concentrated. The crude material was purified by silica gel chromatography (0-20% EtOAc/hexanes) to deliver the title compound (580 mg, 23% yield) as an orange solid.

Step 2: Synthesis of 6-bromo-8-(2,5-difluoro-4-methylbenzyl)-3-fluoroimidazo[1,2-a]pyrazine

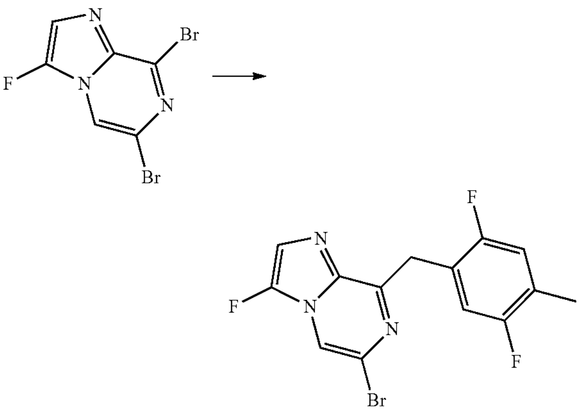

A suspension of dry zinc powder (240 mg, 3.7 mmol) in THF (3.0 mL) was treated with 1,2-dibromoethane (30 mL, cat.) and the resultant mixture was heated at 50° C. Chlorotrimethylsilane (30 mL, cat.) was then added. After 15 min, the mixture was cooled to ambient temperature. Dry lithium chloride (170 mg, 3.9 mmol) was added, followed by dropwise addition of a solution of 1-(bromomethyl)-2,5-difluoro-3-methylbenzene (480 mg, 2.2 mmol) in THF (2.0 mL) (note: exothermic reaction). The mixture was stirred for 1 h at ambient temperature. Meanwhile, a slurry of 6,8-dibromo-3-fluoroimidazo[1,2-a]pyrazine (580 mg, 2.0 mmol) and $Pd(PPh_3)_2Cl_2$ (41 mg, 0.059 mmol) in THF (3.0 mL) was degassed with nitrogen. The freshly formed zincate solution was transferred to this slurry via a syringe and rinsed with 2×0.5 mL THF to ensure complete transfer. The resultant mixture was stirred at ambient temperature for 1 h 20 min and then at 40° C. for 4 h. After cooling to ambient temperature, the reaction was quenched with 4 mL of saturated $NH_4Cl$ solution. The organic layer was concentrated, diluted with $CH_2Cl_2$ (10 mL) and filtered through a bed of Celite. The filtrate was concentrated to yield a brown residue which was purified by silica gel chromatography (compound loaded with $CH_2Cl_2$ and eluted with 0-10% EtOAc/hexanes) to deliver the title compound (440 mg, 63% yield) as a yellow solid.

Step 3: Synthesis of 8-(2,5-difluoro-4-methylbenzyl)-3-fluoroimidazo[1,2-a]pyrazine-6-carbonitrile

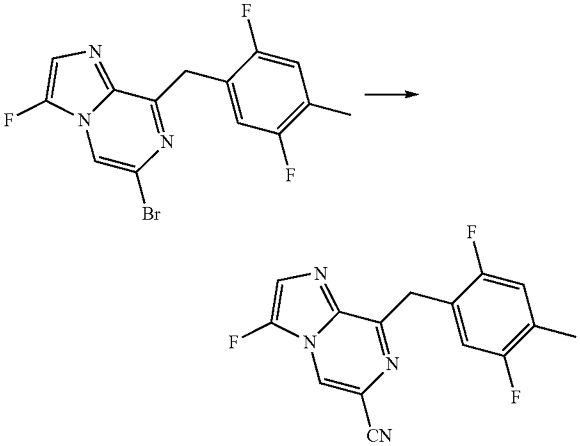

A reaction mixture comprised of 6-bromo-8-(2,5-difluoro-4-methylbenzyl)-3-fluoroimidazo[1,2-a]pyrazine (440 mmol, 1.2 mmol), zinc cyanide (100 mg, 0.87 mmol), $Pd_2(dba)_3$ (46 mg, 0.050 mmol) and 1,1'-bis(diphenylphosphino)ferrocene (dppf) (41 mg, 0.075 mmol) in anhydrous DMF (5.0 mL) was degassed with nitrogen and then heated at 90° C. for 6 h. The reaction was cooled to ambient temperature and treated with $CH_2Cl_2$ (50 mL), water (40 mL) and 28% ammonium hydroxide solution (4.0 mL). The aqueous layer was extracted with $CH_2Cl_2$ (50 mL). The combined organic layers were dried over $Na_2SO_4$, filtered and concentrated to afford a brown oil which was purified by column chromatography (0 to 20% EtOAc/hexanes gradient) to afford the title compound as a light tan solid (310 mg, 81% yield). LC/MS $ES^+$ m/z=302.8 $[M+H]^+$.

Step 4: Synthesis of 8-(2,5-difluoro-4-methylbenzyl)-3-fluoroimidazo[1,2-a]pyrazine-6-carboximidamide

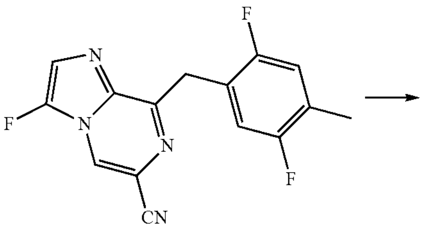

-continued

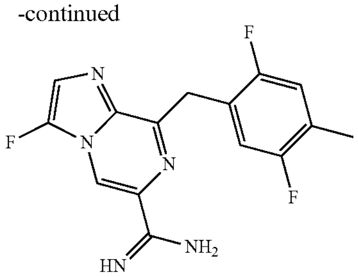

To a suspension of 8-(2,5-difluoro-4-methylbenzyl)-3-fluoroimidazo[1,2-a]pyrazine-6-carbonitrile (150 mg, 0.50 mmol) in methanol (6.0 mL) was added a solution of 0.50 N sodium methanolate in methanol (1.0 mL, 0.50 mmol). After 4 h 30 min of stirring at ambient temperature, ammonium chloride (270 mg, 5.0 mmol) was added, and the reaction was stirred for 18 h. The resultant mixture was concentrated in vacuo, treated with 10% aqueous $NaHCO_3$ solution (10 mL) and sonicated to afford a suspension. After stirring for 1 h, the product was collected by filtration, washed with water (10 mL) and dried in vacuo to afford the title compound (170 mg, >100% yield) as a light tan solid. It was used in the next step without further purification. LC/MS $ES^+$ m/z=319.7 $[M+H]^+$.

Step 5: Synthesis of 2-(8-(2,5-difluoro-4-methylbenzyl)-3-fluoroimidazo[1,2-a]pyrazin-6-fluoropyrimidin-4-ol

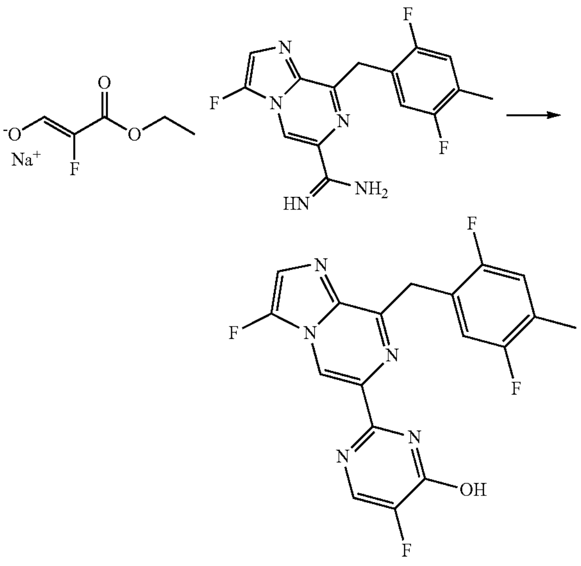

Compound I-18

To a suspension of 8-(2,5-difluoro-4-methylbenzyl)-3-fluoroimidazo[1,2-a]pyrazine-6-carboximidamide (0.50 mmol, theoretical amount from previous step) in ethanol (5.0 mL) was added sodium (Z)-3-ethoxy-2-fluoro-3-oxoprop-1-en-1-olate (310 mg, 2.0 mmol). The reaction was heated in a sealed vial at 90° C. for 16 h. After cooling to ambient temperature, the mixture was diluted with water (7.5 mL), adjusted to pH 4 with 1N aqueous HCl solution. The resultant tan solid was collected by filtration, washed with water (50 mL) and ethyl ether (30 mL), and dried to afford the title compound (140 mg, 71% yield over 2 steps) as a brown solid.

$^1$H NMR (500 MHz, DMSO-$d_6$) δ (ppm) 12.8 (br. s, 1H), 8.98 (s, 1H), 8.22 (br. s, 1H), 7.74 (d, 1H), 7.35 (br. s, 1H), 7.15 (m, 1H), 4.50 (s, 2H), 2.18 (s, 3H).

Compound I-20

The title compound was synthesized in 2 steps:

Step 1: Synthesis of 8-(2,5-difluorobenzyl)imidazo[1,2-a]pyrazine-6-carboximidamide

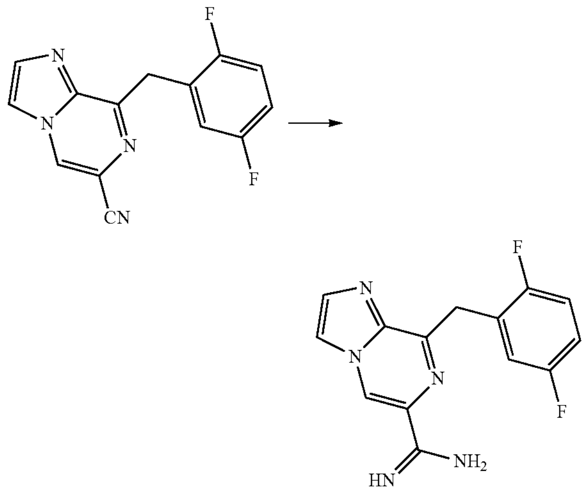

To a solution of 8-(2,5-difluorobenzyl)imidazo[1,2-a]pyrazine-6-carbonitrile (500 mg, 1.9 mmol) in methanol (22 mL) was added a solution of 25 wt % sodium methanolate in methanol (2.1 mL, 9.3 mmol). After 1 h of stirring at ambient temperature, ammonium chloride (1.0 g, 19 mmol) was added and the reaction was allowed to stir overnight. The reaction mixture was concentrated in vacuo, diluted with half-saturated $NaHCO_3$ solution (20 mL) and 1.0 N sodium hydroxide solution (2.0 mL), and extracted with 2×20 mL of EtOAc. The combined organic phases were dried over sodium sulfate, filtered, and concentrated to afford the crude product as a brown solid. It was used in the next step without further purification. LC/MS ES$^+$ m/z=288.1 $[M+H]^+$.

Step 2: Synthesis of 5-fluoro-2-(8-(2,5-difluorobenzyl)imidazo[1,2-a]pyrazin-6-yl)pyrimidin-4-ol

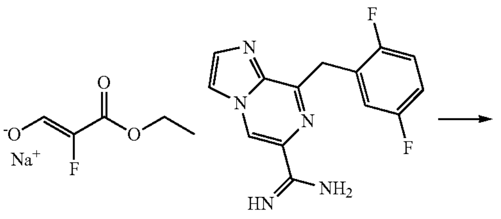

-continued

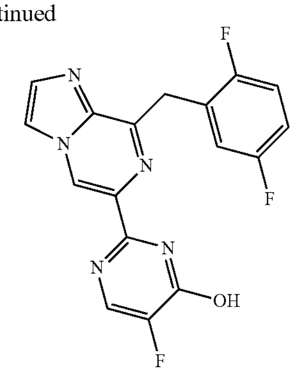

Compound I-20

To a suspension of 8-(2,5-difluorobenzyl)imidazo[1,2-a]pyrazine-6-carboximidamide (500 mg, 1.7 mmol) in ethanol (9.0 mL) was added sodium- -(Z)-3-ethoxy-2-fluoro-3-oxo-prop-1-en-1-olate (820 mg, 5.2 mmol). The reaction was heated in a sealed vial at 90° C. for 2 h. After cooling to ambient temperature, conc. HCl solution was added drop-wise to acidify the mixture to pH 4. The resultant mixture was concentrated in vacuo. Purification by preparative reverse phase HPLC (acetonitrile-water gradient with 0.1% TFA as additive) afforded the title compound (200 mg, 28% yield over 2 steps) as a yellow solid. $^1$H NMR (500 MHz, DMSO-$d_6$) δ (ppm) 12.6 (br. s, 1H), 9.49 (s, 1H), 8.32 (s, 1H), 8.19 (br. s, 1H), 7.89 (s, 1H), 7.43 (s, 1H), 7.25 (m, 1H), 7.13 (m, 1H), 4.58 (s, 2H).

Na+salt of Compound I-20

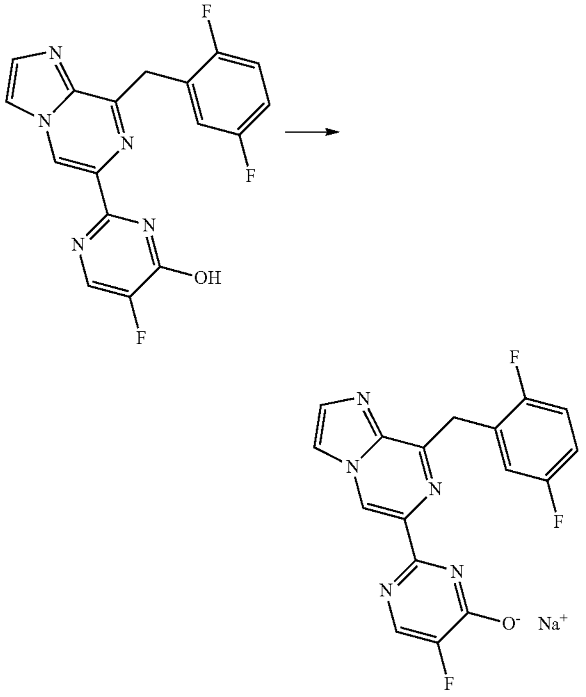

Compound I-20-Na+salt

To a light tan suspension of 5-fluoro-2-(8-(2,5-difluorobenzyl)imidazo[1,2-a]pyrazin-6-yl)pyrimidin-4-ol (Compound I-20, 10 g, 28 mmol) in 450 mL of anhydrous MeOH under a nitrogen atmosphere was added a solution of 0.50 N sodium methanolate in methanol (57 mL, 28 mmol). After brief sonication, the resultant light orange solution was stirred at ambient temperature for 15 min and concentrated to dryness in vacuo. The solid was re-suspended in 200 mL of ether with the aid of sonication and concentrated (two times). The resultant solid was re-suspended in 500 mL of ether and stirred at ambient temperature for 3 h. The solid was collected by vacuum filtration and washed with ether (3×100 mL). After drying overnight on the filter, the product salt was dried in a vacuum oven at 45° C. for 5 days to afford sodium 5-fluoro-2-(8-(2,5-difluorobenzyl)imidazo[1,2-a]pyrazin-6-yl)pyrimidin-4-olate (11 g, 99% yield) as a light tan solid. $^1H$ NMR (500 MHz, $D_2O$) δ (ppm) 8.90 (s, 1H), 7.98 (d, 1H), 7.95 (d, 1H), 7.70 (d, 1H), 7.10 (m, 1H), 6.98-6.89 (m, 2H), 4.53 (s, 2H).

Biological Section

Assessment of the Biological Properties of the Compounds of Table I

The present invention also provides the assessment of the biological properties of compounds of Table I. Representatives of the compounds of this invention have been tested in vitro for their activity as sGC stimulators in a variety of cells and assays and in vivo for their ability to reduce blood pressure in animals. Reduction of blood pressure is used as an indication of the ability of the compounds to engage the target in vivo. These biological properties represent another embodiment of the present invention.

Example 2: Biological Activity Measurement by the cGMP GloSensor Cell-Based Assay, 384-Well Format Human embryonic kidney cells (HEK293) cells expressing GloSensor™ 40F cGMP (Part No: CS182801, Promega) were used to evaluate the activity of test compounds. The luminescent biosensors (engineered luciferase) that were incorporated into these cells detect cGMP formed by the compounds stimulating the sGC enzyme and emit luminescence.

cGMP GloSensor cells were maintained in Dulbecco's Modification of Eagle's Medium (DMEM) supplemented with fetal bovine serum (FBS, 10% final) and hygromycine (200 ug/ml). The day before assay, cells were plated in DMEM with 10% FBS in a 50 μL volume at a density of $1.5\times10^4$ cells/well in a poly-D-lysine coated 384-well flat white-bottom plate (Corning Cat No 35661). Cells were incubated overnight at 37° C. in a humidified chamber with 5% $CO_2$. The next day, medium was removed and cells were replaced with 40 ul/well of GboSensor™, 2 mM (Promega Cat No E1291). Cells were treated for 90 minutes at 25° C. to allow the substrate to equilibrate in the cells. Test compounds and Diethylenetriamine NONOate (DETA-NONOate) was diluted to 3 mM (20×) in serum-free $CO_2$ independent medium and serially diluted at 4× dilutions to create 5× dose curve from which 10 ul was added to the wells (x μM concentration for test compound solution and 10 μM concentration for DETA-NONOate solution; wherein x is one of the following final concentrations: 30 μM, 7.5 μM, 1.9 μM, 469 nM, 117 nM, 29.3 nM, 7.3 nM, 1.83 nM, 0.46 nM, 0.11 nM, 0.03 nM) For the kinetics studies, luminescense was measured right away for 0.2 sec per well with Envision (Perkin Elmer). For endpoint SAR screening, data were collected after 55 min incubation at room temperature.

Concentration response data were analyzed using a 4-parameter fit (log (agonist) vs. response—variable slope). The EC50 was interpolated from the curve fit and is defined as the concentration at which the compound elicits 50% of its maximal response. When the experiment was carried out multiple times for a given compound, the geometrical mean of all experiments is reported.

Table A below summarizes the values of $EC_{50}$ in the Glo assay for compounds of the invenion:

TABLE A

| Compound No. | Glo $EC_{50}$ (nM) | Compound No. | Glo $EC_{50}$ (nM) |
|---|---|---|---|
| I-19 | B | I-5 | A |
| I-2 | B | I-14* | A |
| I-1 | B | I-16 | A |
| I-4 | B | I-15 | B |
| I-20* | A | I-17 | A |
| I-11 | B | I-18 | A |
| I-13 | B | I-12 | B |
| I-10 | B | I-3 | A |
| I-6 | A | I-8 | C |
| I-7 | B | I-9 | B |

sGC enzyme activity values in HEK cells, determined by the GloSensor assay. Code definitions for the sGC enzyme activity values, expressed as $EC_{50}$ which is defined as the concentration at which the compound elicits 50% of its maximal response: $EC_{50} \leq 100$ nM = A; 100 nM < $EC_{50} \leq 1000$ nM = B; 1000 nM < $EC_{50}$ = C.

*For Compounds I-20 and I-14, both the free acid and the sodium salt were used and the results here are the average of all experiments run independently of form.

Example 3. Biological Activity Measurement by the cGMP Neuronal Cell-Based Assay Rat primary neurons were isolated from fetuses of 18-day pregnant Sprague-Dawley females. The fetuses were collected in Hanks' balanced salt solution (HBSS) and brains were rapidly removed. The cerebral hippocampi were isolated and mechanically fragmented. Further tissue digestion was performed with 0.25% (wt/vol) trypsin solution in HBSS without Ca2+ and Mg2+ for 15 min at 37° C. After trypsination, cells were washed and resuspended in neurobasal medium supplemented with 0.5 mM L-glutamine, 12.5 uM glutamic acid, 2% B-27 and 100 U/mL penicillin, and 100 μg/mL streptomycin. Cells were plated at a density of $26\times10^3$ or $4\times10^4$ or $3\times10^4$ cells/well in a poly-D-lysine coated 384-well flat clear-bottom plate (Corning Cat No 354662). Cells were incubated 6-7 days at 37° C. in a humidified chamber with 5% $CO_2$. Media was removed and cells were washed 1× with HBSS containing Ca2+ and Mg2+, and replaced with 40 uL HBSS containing 0.5 mM IBMX, and incubated for 15 minutes at 37° C. 10 uL of a 5× stock of test compounds with diethylenetriamine NONOate (DETA-NO) was added. Final concentration of DETA-NO was either 10 μM or 30 μM. Cells were incubated for 20 min at 37° C. Medium was removed, 50 uL of ice-cold 10% acetic acid was added, and incubated for 60 minutes at 4° C. Following centrifugation at 4° C. for 5 minutes at 1000×g to pellet cell debris, the supernatant was aspirated to a clean plate and the samples were analyzed for cGMP content. cGMP concentrations were determined from each sample using LC-MS/MS.

Concentration response data were analyzed using a 4-parameter fit (log (agonist) vs. response—variable slope). The EC50 was interpolated from the curve fit and is defined as the concentration at which the compound elicits 50% of its maximal response. When the experiment was carried out multiple times for a given compound, the geometrical mean of all experiments is reported.

Table B below summarizes the values of $EC_{50}$ in the Neuronal assay for compounds of the invention:

TABLE B

| Compound No. | sGC Neuron $EC_{50}$ (nM) | Compound No. | sGC Neuron $EC_{50}$ (nM) |
|---|---|---|---|
| I-5 | A | I-3 | A |
| I-2 | B | I-15 | B |
| I-1 | B | I-9 | A |
| I-4 | A | I-19 | A |
| I-20* | A | I-14* | A |
| I-16 | A | I-12 | A |
| I-6 | A | I-7 | A |

Neuronal-based cell assay. $EC_{50} \leq 100$ nM = A; 100 nM < $EC_{50} \leq 1000$ nM = B; 1000 nM < $EC_{50}$ = C.
*For Compounds I-20 and I-14, both the free acid and the sodium salt were used and the results here are the average of all experiments run independently of form.

Example 4: Biological Activity Measurement on Human a2b1 sGC Isozyme Stably Expressed in CHO-K1 Cells sGC stimulators were dissolved in DMSO as a 10 mM solution and stored at −20° C. To achieve desired test concentrations, stock concentrations were serially diluted into DMSO and then diluted to the appropriate concentration in assay buffer.

CHO-K1 cells stably transfected with human α2β1 sGC isozyme (generated by GenScript for Ironwood) were cultured in F-12K medium (ATCC catalog #30-2004) with 10% fetal calf serum, 4 μg/mL puromycin (Gibco catalog #A11138-03) and 0.4 mg/mL of geneticin (Gibco catalog #10131-027) in a 95% humidified atmosphere containing 5% $CO_2$ in air at 37° C. For GC activity assays, cells were seeded in 384 well poly-D-lysine coated flat bottom plates (Fisher Scientific #08-774-311) in either 50 μL or 70 μL medium at a density of either $3\times10^4$ cells/well or $15\times10^3$, respectively. Cells were incubated for 24 hours at 37° C. in a humidified chamber supplemented with 5% $CO_2$.

For each test concentration, the compound was diluted in 100% DMSO to 100-fold of its final assay concentration. Immediately prior to the assay, the solution was diluted 20-fold into HBSS containing calcium, magnesium, and 50 μM DETA-NONOate (5× the final assay concentration). Medium was removed and cells were washed once with 40 μL of HBSS. Cells were then incubated with 40 μL of a solution containing 0.5 mM IBMX in HBSS for 15 min at 37° C. 10 μL from the sGC stimulator/HBSS/DETA-NONOate plate was added to the cells, which were incubated for an additional 20 min at 37° C. Final DMSO concentration was 1%, final DETA-NONOate concentration was 10 μM; and final compound concentrations were 30,000 nM, 6000 nM, 1200 nM, 240 nM, 48 nM, 9.6 nM, 1.92 nM, 0.384 nM, 0.077 nM, 0.015 nM, or 0.003 nM.

Following incubation with compound, assay buffer was removed and 50 μL of ice-cold 10% acetic acid+150 ng/mL internal standard (+3 cGMP) was added to each well. Samples were incubated on ice for 30-60 min. Following centrifugation at 4° C. for 5 min at 1000×g to pellet cell debris, the supernatant was transferred to a clean plate and the samples analyzed for cGMP content.

Data were analyzed with a 4-parameter fit (log(agonist) vs. response—variable slope) using GraphPad Prism Software v.8. The $EC_{50}$ was interpolated from the curve fit and is defined as the concentration at which the compound elicits 50% of its maximal response. When the experiment was carried out multiple times for a given compound, the geometrical mean of all experiments is reported.

Table C below summarizes the values of $EC_{50}$ in the CHO assay for compounds of the invention:

TABLE C

| Compound No. | sGC CHO $EC_{50}$ (nM) | Compound No. | sGC CHO $EC_{50}$ (nM) |
|---|---|---|---|
| I-14* | A | I-15 | B |
| I-2 | B | I-19 | A |
| I-17 | A | I-18 | A |
| I-4 | A | I-5 | A |
| I-20* | A | I-16 | A |

CHO cell assay. $EC_{50} \leq 100$ nM = A; 100 nM < $EC_{50} \leq 1000$ nM = B; 1000 nM < $EC_{50}$ = C.
*For Compounds I-20 and I-14, both the free acid and the sodium salt were used and the results here are the average of all experiments run independently of form.

Example 5: Blood Pressure Effects in Normotensive Rats, Following Acute Dose at Multiple Concentrations for Representative Compounds of the Invention a) Compound I-14

Male, normotensive Sprague Dawley rats were purchased from Charles River Laboratories. These rats have indwelling femoral artery catheters installed. Animals were harnessed to a tether system and attached to pressure transducers to monitor cardiovascular (CV) parameters, specifically mean arterial pressure (MAP) and heart rate (HR). Animals were acclimated to the system overnight and baseline CV parameters collected. The conscious, freely moving rats were then administered a single oral dose of the Compound I-14 (doses generated from the sodium salt of Compound 14) in Milli-Q water at 1, 3, 10 and 30 mg/kg. A blood sample was collected from each animal through the catheter line at pre-dose and 2 hours post-dose for compound concentration quantification. Hemodynamic measures were recorded for ten hours post-dose. Fifty-four male rats were used for these studies and they were ordered to be received at a body weight range of 250-275 grams. They were single housed under controlled conditions of temperature (21±1° C.), relative humidity (36±1%) and placed in a 12-hr light-dark cycle (lights on at 6:00 AM and off at 6:00 PM) room at SmartLabs vivarium (21 Erie Street, Cambridge, MA) under protocol MIL-110. Animals were allowed ad libitum access to chow (LabDiet Prolab Isopro RMH 3000, St. Louis, MO) and water. Two sets of studies were carried out. For the first set of studies Compound I-14 was formulated at 0.3 and 1.0 mg/ml in Milli-Q water and frozen at −20° C. For the second set of studies, the sodium salt of Compound I-14 was weighed at Cyclerion Therapeutics and reconstituted at SmartLabs to provide 0.1, 0.3, 1.0 and 3.0 mg/ml solutions of Compound I-14 in Milli-Q water. Formulations prepared were thawed less than 4 hours before dosing and stored at room temperature or were made less than 2 hours before dosing and stored at room temperature.

Studies were conducted over 6 separate sessions. The total number of subjects and treatment assignments are listed in the table below. Animals were initially used within 3 days of receipt and if catheters remained patent, reused once after 6-7 days of washout. No animals were used more than twice.

| Group | Number of animals | Treatment | Dose Volume | Dose Concentration |
|---|---|---|---|---|
| 1 | 13 | Vehicle | 10 mL/kg | — |
| 2 | 9 | 1 mg/kg Compound I-14 | 10 mL/kg | 0.1 mg/mL |
| 3 | 6 | 3 mg/kg Compound I-14 | 10 mL/kg | 0.3 mg/mL |

-continued

| Group | Number of animals | Treatment | Dose Volume | Dose Concentration |
|---|---|---|---|---|
| 4 | 11 | 10 mg/kg Compound I-14 | 10 mL/kg | 1.0 mg/mL |
| 5 | 6 | 30 mg/kg Compound I-14 | 10 mL/kg | 30 mg/mL |

Measurement of Blood Pressure

This study utilized ADInstruments LabChart (v8) to collect hemodynamic data from conscious, freely moving rats tethered to a blood pressure transducer (Harvard Apparatus cat #APT300). Following an overnight acclimation to the tether and pressure transducer, animals were dosed following a 1-hr baseline recording period. Animals were administered a single oral (P.O.) dose of the sodium salt form of Compound I-14 or vehicle at a dose volume of 10 mL/kg. Data collection was continued for 10 hours post-dose.

ADInstruments LabChart (v8) was used to monitor and export hemodynamic data. Blood pressure and heart rate were continuously monitored, and data were collected at 1000 data points per second then averaged into 10-minute bins for analysis. Change from baseline MAP (ΔBMAP) and HR (ΔBHR) were calculated using the pre-dose baseline averaged over the 1-hr period prior to dosing using Microsoft Excel for Microsoft 365. This 10-minute bin dataset was used to determine peak ΔVMAP, time peak ΔVMAP, peak ΔVHR and time of peak ΔVHR. The dataset was further consolidated into 1-hr bins for the MAP and HR figures and the analysis of ΔBMAP, ΔBMAP, and ΔBHR. The definitions of these terms/abbreviations are summarized below:

| | |
|---|---|
| $\Delta_B$MAP, dMAP | Change from baseline mean arterial pressure |
| $\Delta_B$HR, dHR | Change from baseline heart rate |
| $\Delta_V$MAP | Vehicle-adjusted mean arterial pressure |
| $\Delta_V$MAP | Vehicle-adjusted heart rate |
| AOC | Area Over the Curve |

Statistical analyses were performed in Graphpad Prism (v8). Significance, as compared to vehicle-treated rats, for ΔBMAP and ΔBHR data was determined by 2-way repeated measures ANOVA followed by a Dunnett's multiple comparisons test, if there was a missing data point, a mixed-effect analysis was utilized. Vehicle-adjusted MAP (ΔVMAP) was calculated by subtracting ΔBMAP of the vehicle group from the ΔBMAP of each dose group at each timepoint. Vehicle-adjusted HR (ΔVHR) was calculated in a similar manner to ΔVMAP.

Significance of AOC data were determined by one-way ANOVA followed by a Dunnett's multiple comparisons test as compared to vehicle.

Some study data were removed prior to analysis. Data collected 130- and 140-min post-dose were removed due to the 2-hour blood sample collection. A few timepoints for one rat at 1 mg/kg were excluded due to signal loss during the experiment starting at 470. minutes and continuing until the end of the study (600 min). The entire time courses of 5 animals were excluded from all datasets for a variety of reason, including them being outliers for particular analyses or due to signal loss leading to abnormal results.

Blood Pressure Changes

The change from baseline MAP (ΔBMAP) is shown graphically in FIG. 1. There was a greater decrease in MAP (as assessed by change from baseline MAP, ΔBMAP) in rats treated with Compound I-14 than in vehicle-treated rats. The ΔBMAP dataset was significant by 2-way ANOVA ($p<0.0001$ for treatment and time and $p=0.045$ for treatment×time interaction). Dunnett's multiple comparison test of the main treatment effect yielded p=ns for 1 mg/kg, $p=0.0034$ for 3 mg/kg, and $p<0.0001$ for the 10 and 30 mg/kg doses as compared to vehicle treated rats. A separate Dunnett's multiple comparison test of simple effects at each timepoint and each dose versus vehicle-treated rats show a greater decrease in ΔBMAP throughout the 6-hour post-dose period in rats treated with 10 and 30 mg/kg Compound I-14; at 1-, 2-, and 3-hours post-dose in rats treated with 3 mg/kg Compound I-14; but not in rats treated with 1 mg/kg Compound I-14.

Maximum effect of Compound I-14 on ΔVMAP was calculated by using the 10-minute binned dataset and is shown in Table D below:

TABLE D

Maximum Effect of Compound I-14 on Vehicle-adjusted MAP (ΔVMAP)

| Compound 14 | Peak $\Delta_V$MAP (mm Hg) | Time at Peak (min) |
|---|---|---|
| 1 mg/kg | −6.2 | 90 |
| 3 mg/kg | −10.1 | 70 |
| 10 mg/kg | −22.3 | 30 |
| 30 mg/kg | −24.4 | 30 |

The no effect dose on ΔBMAP is 1 mg/kg as assessed by main effect analysis, simple effects analysis, and by AOC.

Conclusion

Compound I-14 lowered MAP from baseline and as adjusted from vehicle at 3, 10, and 30 mg/kg.

b) Compound I-20

Analogous studies to the ones described above were carried out with Compound I-20. The conscious, freely moving rats were administered a single oral dose of Compound I-20 (dosages prepared from the sodium salt of Compound I-20) in Milli-Q water at 1, 3, 10 and 30 mg/kg. A blood sample was collected from each animal through the catheter line at pre-dose and 2 hours post-dose for compound concentration quantification. Hemodynamic measures were recorded for ten hours post-dose.

Blood Pressure Changes

Figure 2:
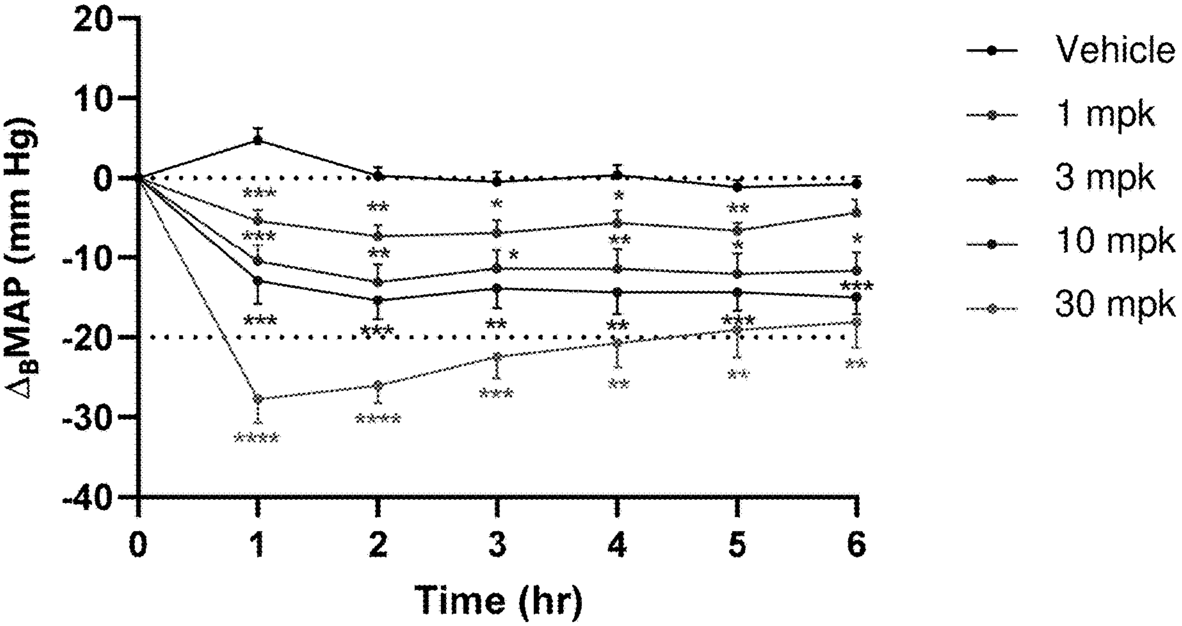
FIG. 2 shows the effect of compound I-20 on $\Delta_B$MAP in male, normotensive rats.

The change from baseline MAP ($\Delta_B$MAP) is shown graphically in FIG. 2. There was a greater decrease in MAP (as assessed by change from baseline MAP, $\Delta_B$MAP) in rats treated with Compound I-20 than in vehicle-treated rats. The $\Delta_B$MAP dataset was significant by 2-way ANOVA ($p<0.0001$ for treatment and treatment×time interaction; $p=0.022$ for time). Dunnett's multiple comparison test of the main treatment effect yielded $p=0.055$ (ns) for 1 mg/kg, $p=0.0001$ for 3 mg/kg, and $p<0.0001$ for the 10 and 30 mg/kg doses as compared to vehicle-treated rats. A separate Dunnett's multiple comparison test of simple effects at each timepoint and each dose versus vehicle-treated rats show a greater decrease in MAP throughout the 6-hour post-dose period in rats treated with 3, 10, and 30 mg/kg Compound I-20; at 1-, 2-, 3-, 4-, and 5-hours post-dose in rats treated with 1 mg/kg Compound I-20.

The maximum effect of Compound I-20 on ΔvMAP (vehicle-adjusted MAP) was calculated by using the 10-minute binned dataset and is shown Table E below.

TABLE E

| Maximum Effect of Compound I-20 on vehicle-adjusted MAP ($\Delta_V$MAP) | | |
|---|---|---|
| Compound 20 | Peak $\Delta_V$MAP (mm Hg) | Time at Peak (min) |
| 1 mg/kg | −14.3 | 20 |
| 3 mg/kg | −19.2 | 20 |
| 10 mg/kg | −20.2 | 30 |
| 30 mg/kg | −38.1 | 30 |

Conclusions

Compound I-20 lowered MAP at 1, 3, 10, and 30 mg/kg, both from baseline and as adjusted from vehicle.

Other BP Measurements

In similar studies to those described above, Compound I-4, formulated in PEG400 and dosed at 10 mg/kg displayed a maximal reduction of MAP from baseline ($\Delta_B$MAP) of 20 mm Hg at 50 min after dosing. In similar studies to those described above, Compound I-20, formulated in PEG400 and dosed at 10 mg/kg displayed a peak $\Delta_B$MAP of −26 mm Hg at 42 min after dosing. In another study in which Compound I-20 was tested at 1, 3 or 10 mg/kg and formulated in methylcellulose, the compound was able to reduce MAP from baseline at all doses tested.

The invention claimed is:

1. A compound represented by Formula I:

Formula I

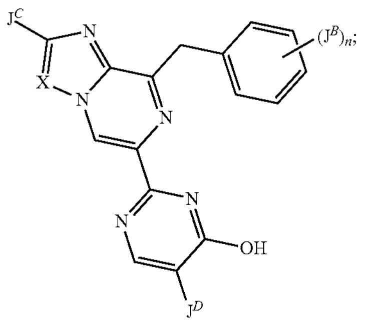

or a pharmaceutically acceptable salt thereof, wherein:

$J^C$ is selected from the group consisting of hydrogen, halogen $C_{1-6}$ alkyl and $C_{1-6}$ fluoroalkyl substituted with 1 to 3 fluoro atoms;

X is N or $C(J^{C1})$;

$J^{C1}$ is selected from the group consisting of hydrogen, halogen, $C_{1-6}$ alkyl and $C_{1-6}$ fluoroalkyl substituted with 1 to 3 fluoro atoms;

each $J^B$ is independently selected from the group consisting of hydrogen, halogen, $C_{1-6}$ alkyl and $C_{1-6}$ fluoroalkyl substituted with 1 to 3 fluoro atoms;

$J^D$ is selected from the group consisting of hydrogen, halogen, $C_{1-6}$ alkyl and $C_{1-6}$ fluoroalkyl substituted with 1 to 3 fluoro atoms; and n is an integer selected from 0, 1, 2, 3 or 4, provided that the compound is not one of the following:

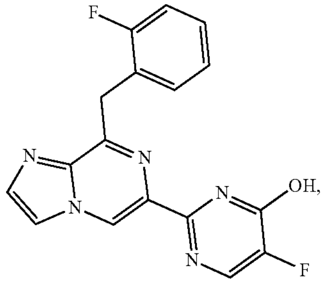

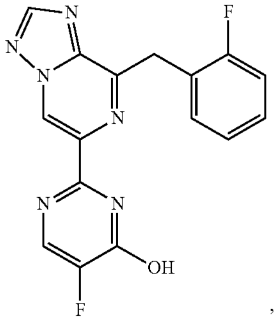

,

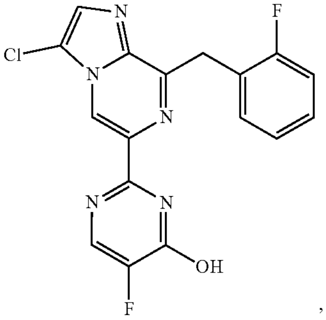

,

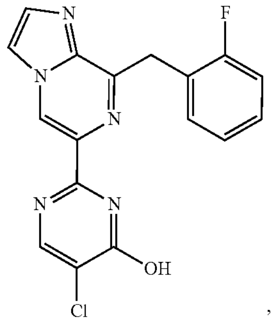

,

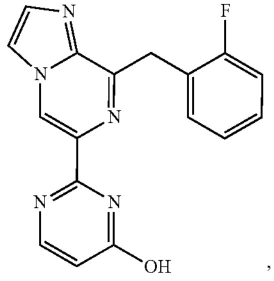

,

-continued

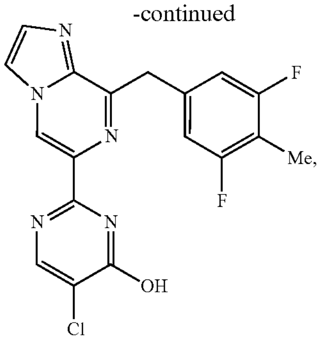

and

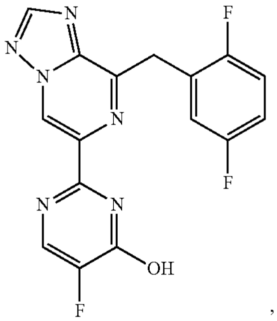

, or a pharmaceutically acceptable salt thereof.

2. The compound of claim 1, wherein the compound is represented by Formula IA:

Formula IA

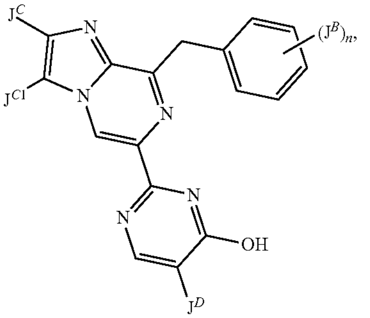

or a pharmaceutically acceptable salt thereof.

3. The compound of claim 1 or 2, or a pharmaceutically acceptable salt thereof, wherein $J^{C1}$ is H, F, Cl, $C_{1-2}$ alkyl or $C_{1-2}$ fluoroalkyl substituted with 1 to 3 fluoro atoms.

4. The compound of claim 1, wherein the compound is represented by Formula IB:

Formula IB

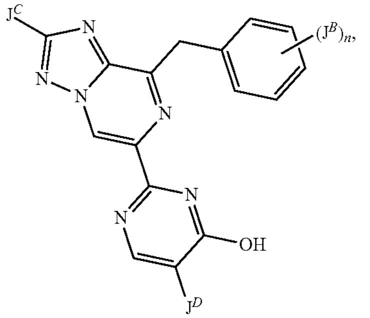

or a pharmaceutically acceptable salt thereof.

5. The compound of claim 1, or a pharmaceutically acceptable salt thereof, wherein:

n is 2 or 3

(ii) n is 0; or (iii) n is 1.

6. The compound of claim 1, or a pharmaceutically acceptable salt thereof, wherein each $J^B$ is independently H, F, or $C_{1-4}$ alkyl or $C_{1-4}$ fluoroalkyl substituted with 1 to 3 fluoro atoms.

7. The compound of claim 1, or a pharmaceutically acceptable salt thereof, wherein n is 2 or 3; and each $J^B$ is independently F, methyl or fluoromethyl substituted with 1 to 3 fluoro atoms.

8. The compound of any one of claims 1, or a pharmaceutically acceptable salt thereof, wherein:

(i) n is 2; and $J^B$ are both F or one of $J^B$ is F and the other is methyl;

(ii) n is 3; and two of $J^B$ are F and the other is methyl.

9. The compound of claim 1, or a pharmaceutically acceptable salt thereof, wherein $J^D$ is H, F, Cl, methyl, ethyl, fluoromethyl or fluoroethyl.

10. The compound of claim 1, or a pharmaceutically acceptable salt thereof, wherein $J^C$ is H, Cl, F, methyl, ethyl, fluoromethyl, or fluoroethyl.

11. The compound of claim 10, or a pharmaceutically acceptable salt thereof, wherein $J^C$ is H.

12. The compound of claim 1, wherein the compound is selected from:

I-1

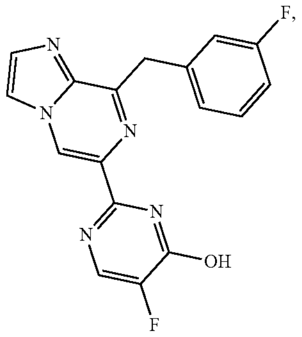

I-2

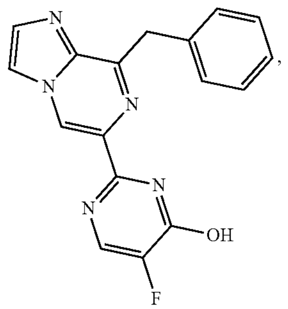

-continued
I-3
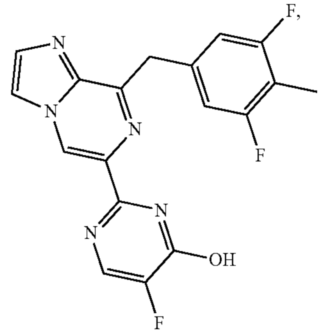
I-4
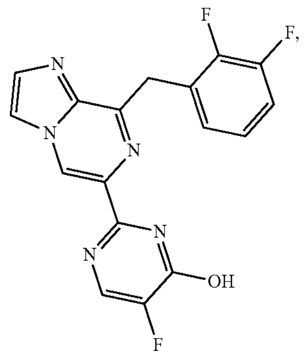
I-5
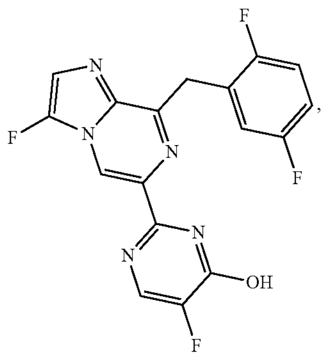
I-6
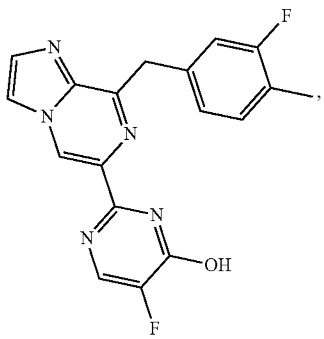
-continued
I-7
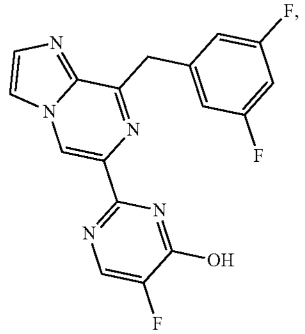
I-8
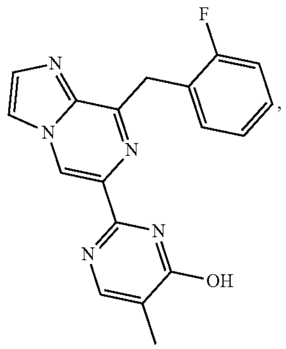
I-9
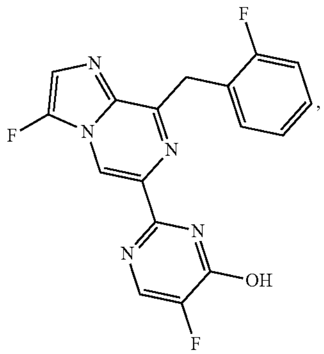
I-10
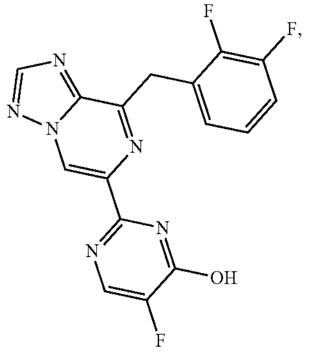

-continued
I-11
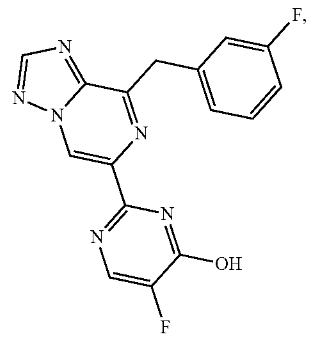
I-12
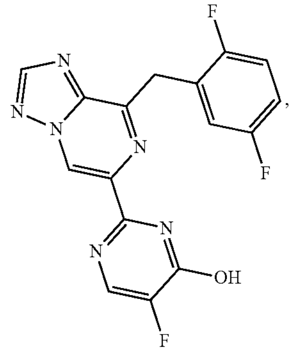
I-13
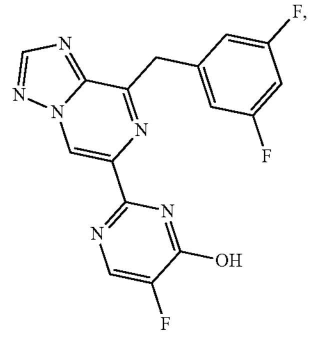
I-14
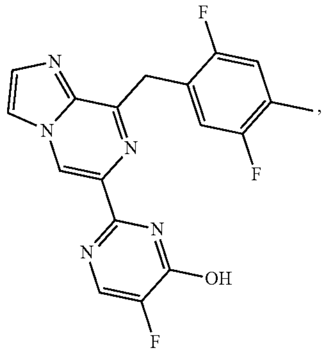
-continued
I-15
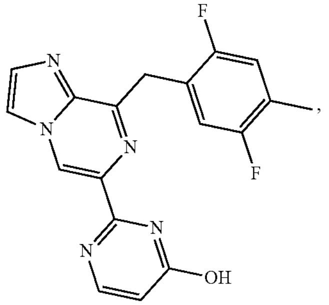
I-16
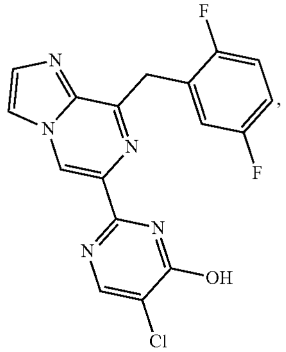
I-17
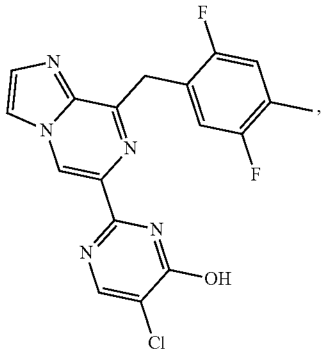
I-18
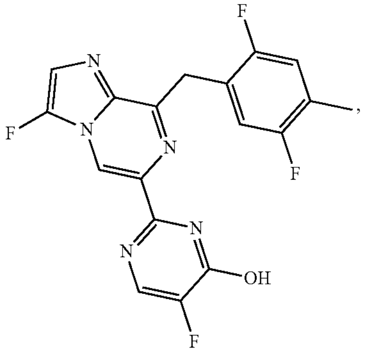
and -continued
I-19
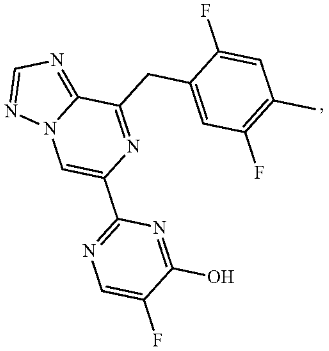
or a pharmaceutically acceptable salt thereof.
13. The compound of claim 12, wherein the compound is selected from:
I-1
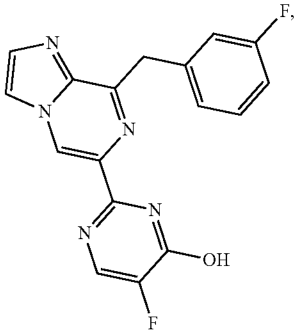
I-2
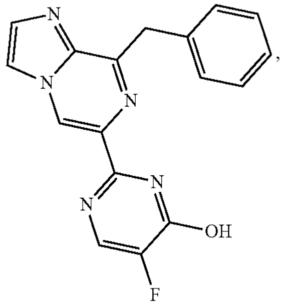
I-3
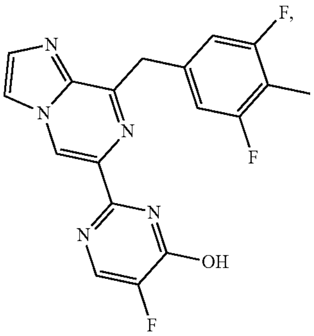
-continued
I-4
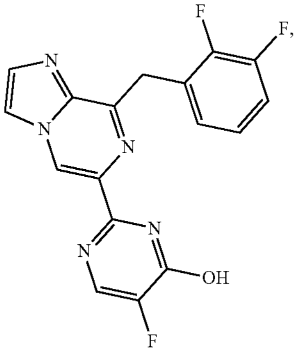
I-5
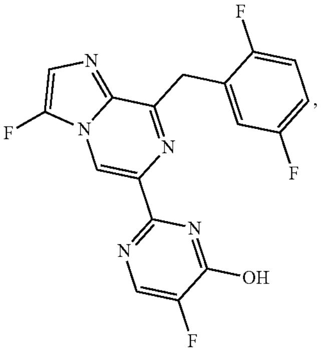
I-6
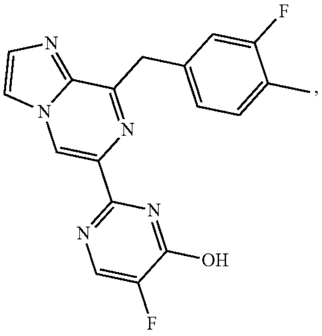
I-7
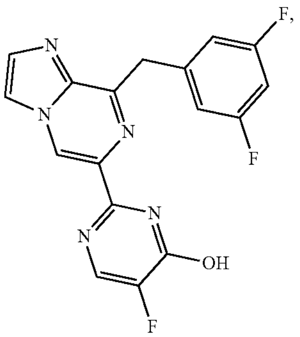

-continued
I-8
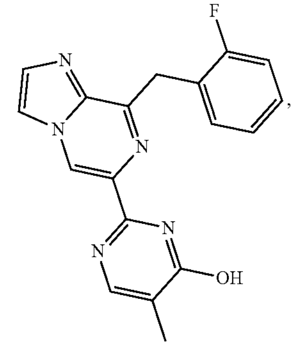
I-9
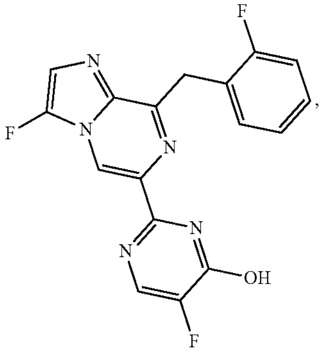
I-14
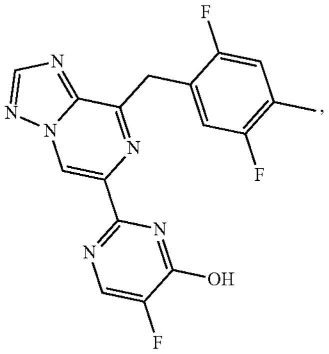
I-15
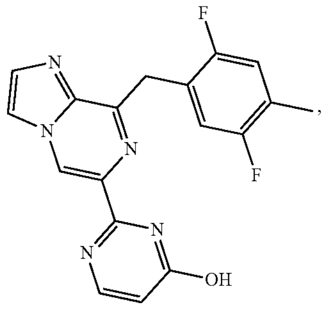
-continued
I-16
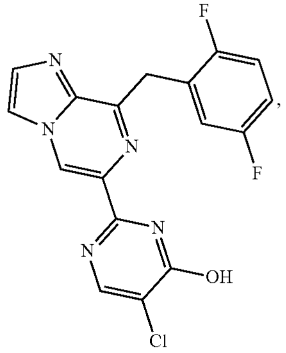
I-17
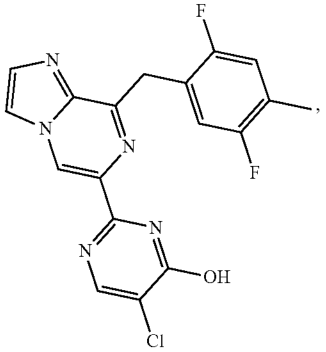
and
I-18
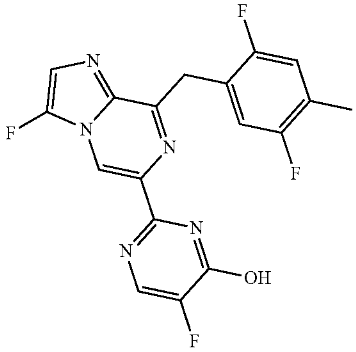
or a pharmaceutically acceptable salt thereof.
14. The compound of claim 13, wherein the compound is selected from:
I-3
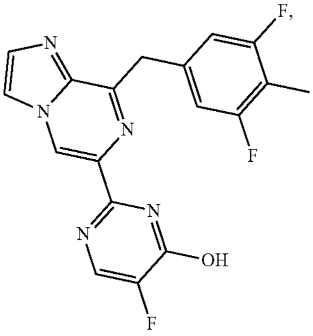

I-4
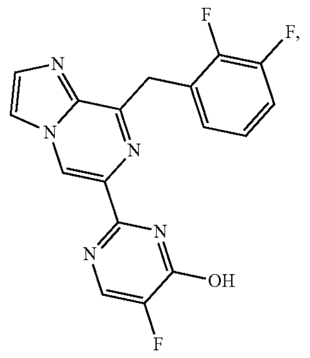
I-5
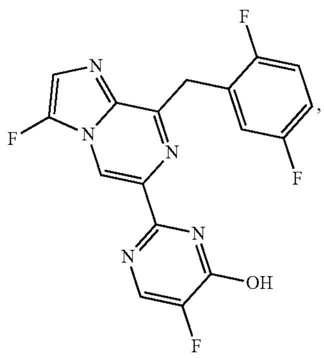
I-6
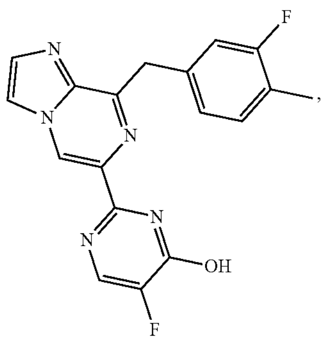
I-7
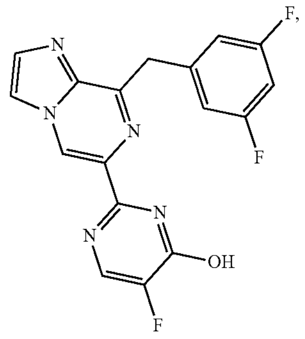
I-14
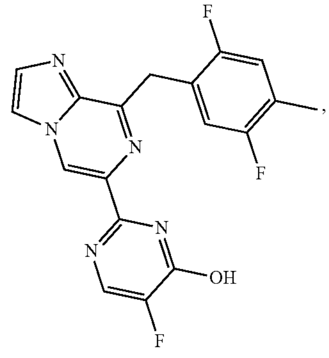
I-15
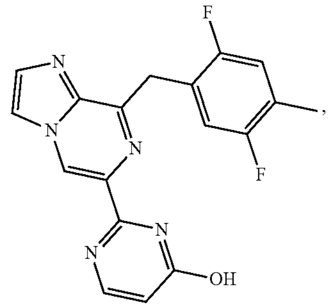
I-16
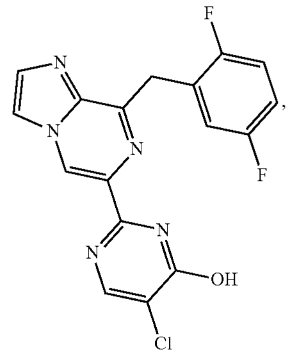
I-17
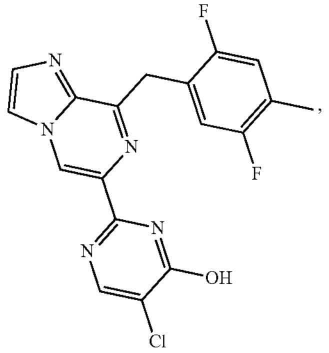
and -continued
I-18
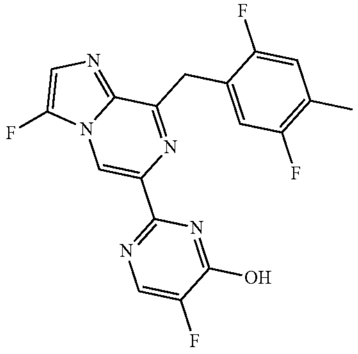
or a pharmaceutically acceptable salt thereof.
15. The compound of claim 13, wherein the compound is selected from:
I-1
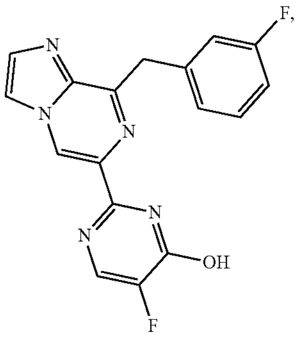
I-2
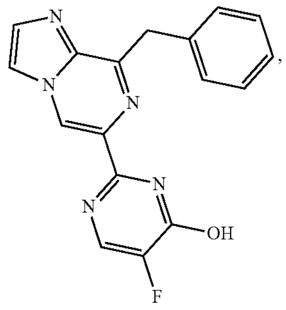
I-8
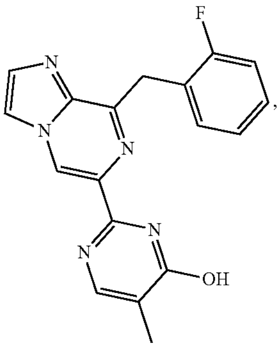
and
-continued
I-9
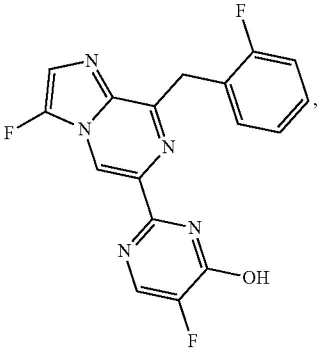
or a pharmaceutically acceptable salt thereof.
16. The compound of claim 12, wherein the compound is selected from:
I-10
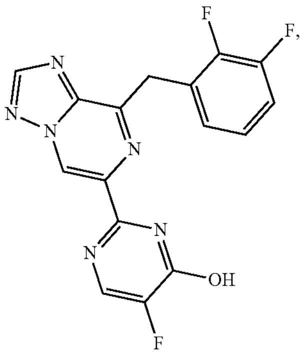
I-11
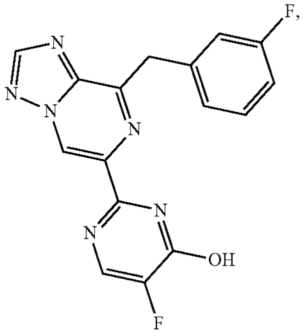

-continued
I-12
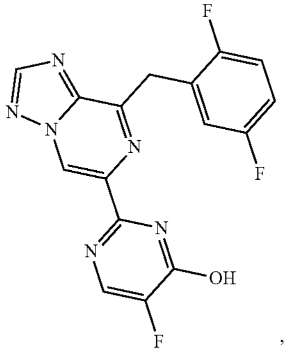
,
I-13
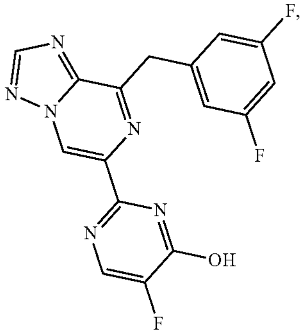
F, and
-continued
I-19
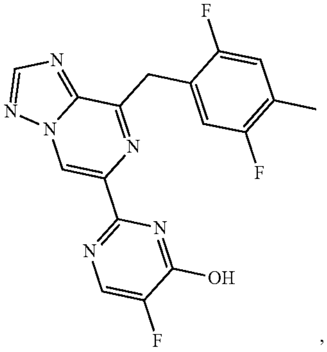
,
or a pharmaceutically acceptable salt thereof.
17. A pharmaceutical composition comprising a compound of claim 1, or a pharmaceutically acceptable salt thereof, and a pharmaceutically acceptable excipient or carrier.
* * * * *